(12) United States Patent
Weber et al.

(10) Patent No.: US 6,342,611 B1
(45) Date of Patent: Jan. 29, 2002

(54) FLUOROGENIC OR FLUORESCENT REPORTER MOLECULES AND THEIR APPLICATIONS FOR WHOLE-CELL FLUORESCENCE SCREENING ASSAYS FOR CAPSASES AND OTHER ENZYMES AND THE USE THEREOF

(75) Inventors: Eckard Weber; Sui Xiong Cai, both of San Diego, CA (US); John F. W. Keana, Eugene, OR (US); John A. Drewe, Costa Mesa; Han-Zhong Zhang, Irvine, both of CA (US)

(73) Assignee: Cytovia, Inc., San Diego, CA (US)

( * ) Notice: Subject to any disclaimer, the term of this patent is extended or adjusted under 35 U.S.C. 154(b) by 0 days.

(21) Appl. No.: 09/168,888

(22) Filed: Oct. 9, 1998

Related U.S. Application Data
(60) Provisional application No. 60/061,582, filed on Oct. 10, 1997.

(51) Int. Cl.[7] ............................................. C07D 311/88
(52) U.S. Cl. ...................................................... 549/227
(58) Field of Search ........................................ 549/227

(56) References Cited

U.S. PATENT DOCUMENTS

| | | | |
|---|---|---|---|
| 4,336,186 A | 6/1982 | Gargiulo et al. | |
| 4,557,872 A | 12/1985 | Mangel et al. | 260/112 R |
| 4,640,893 A | 2/1987 | Mangel et al. | 435/23 |
| 5,208,148 A | 5/1993 | Haugland et al. | 435/14 |
| 5,227,487 A | 7/1993 | Haugland et al. | 546/15 |
| 5,362,628 A | 11/1994 | Haugland et al. | 435/18 |
| 5,443,986 A | 8/1995 | Haughland et al. | 435/4 |
| 5,556,992 A | 9/1996 | Gaboury et al. | 549/227 |
| 5,576,424 A | 11/1996 | Mao et al. | 536/17.9 |
| 5,587,490 A | 12/1996 | Goodrich, Jr. et al. | 549/282 |
| 5,605,809 A | 2/1997 | Komoriya et al. | 435/23 |
| 5,698,411 A | 12/1997 | Lucas et al. | 435/29 |
| 5,714,342 A | 2/1998 | Komoriya et al. | 435/23 |
| 5,733,719 A | 3/1998 | Jaffe et al. | 435/4 |
| 5,773,236 A | 6/1998 | Diwu et al. | 435/15 |
| 5,776,720 A | 7/1998 | Jaffe et al. | 435/29 |
| 5,843,635 A | 12/1998 | Schlossman et al. | 435/5 |
| 5,849,513 A | 12/1998 | Jaffe et al. | 435/29 |
| 5,871,946 A | 2/1999 | Lucas et al. | 435/18 |
| 5,897,992 A | 4/1999 | Fernhead et al. | 435/29 |
| 5,908,750 A | 6/1999 | Reed et al. | 435/6 |

FOREIGN PATENT DOCUMENTS

| | | |
|---|---|---|
| CA | 2119840 | 9/1994 |
| EP | 0 285 179 B1 | 5/1988 |
| WO | WO 93/04192 | 3/1993 |
| WO | WO 93/10461 | 5/1993 |
| WO | WO 96/20721 | 7/1996 |
| WO | WO 96/36729 | 11/1996 |
| WO | WO 98/55863 | 12/1998 |
| WO | WO 98/57664 | 12/1998 |

OTHER PUBLICATIONS

A. Alder et al, Chemical Abstract No. 123: 35266 (1995).*
Handbook of Fluorescent Probes and Research Chemicals, Sixth Ed., Molecular Probes, Inc., p. 226, 1996.*
Greene et al, Protective Groups in Organic Synthesis, John Wiley & Sons, Inc., NY, pp. 309–315, 1980.
Fulda, S. et al., "Betulinic Acid Triggers CD95 (APO–1/Fas)– and p.53–independent Apoptosis via Activation of Capases in Neuroectodermal Tumors," *Cancer Research* 57:4956–4964 (Nov. 1, 1997).
Haugland, R.P., "Handbook of Fluorescent Probes and Research Chemicals," Sixth Edition, Molecular Probes, Inc., Eugene, OR, pp. 226–228 (1996).
Mohr, S. et al., "Macrophages resistant to endogenously generated nitric oxide–mediated apoptosis are hypersensitive to exogenously added nitric oxide donors: Dichotomous apoptotic response independent of caspase 3 and reversal by the mitogen–activated protein kinase kinase (MEK) inhibitor PD 098059," *Proc. Natl. Acad. Sci. USA* 95:5045–5050 (Apr. 1998).
Qi, X.–M. et al., "Baculovirus p35 and Z–VAD–fmk inhibit thapsigargin–induced apoptosis of breast cancer cells," *Oncogene* 15:1207–1212 (Sep. 4, 1997).
Stevens, J.T. et al., "In vitro proteolytic activity and active–site identification of the human cytomegalovirus protease," *Eur. J. Biochem.* 226:361–367 (1994).
Tamburini, P.P. et al., "A Fluorometric Assay for HIV–Protease Activity Using High–Performance Liquid Chromatography," *Analyt. Biochem.* 186:363–368 (1990).
Thornberry, N.A. et al., "A novel heterodimeric cysteine protease is required for interleukin–1β processing in monocytes," *Nature* 356:768–774 (1992).
Webb, N.R. and M.D. Summers, "Expression of Proteins Using Recombinant Baculoviruses," *Tech.–J. Meth. Cell Molec. Biol.* 2:173–188 (1990).

(List continued on next page.)

*Primary Examiner*—Mary E. Ceperley
(74) *Attorney, Agent, or Firm*—Sterne, Kessler, Goldstein & Fox P.L.L.C.

(57) ABSTRACT

The present invention relates to novel fluorescent dyes, novel fluorogenic and fluorescent reporter molecules and new enzyme assay processes that can be used to detect the activity of caspases and other enzymes involved in apoptosis in whole cells, cell lines and tissue samples derived from any living organism or organ. The reporter molecules and assay processes can be used in drug screening procedures to identify compounds which act as inhibitors or inducers of the caspase cascade in whole cells or tissues. The reagents and assays described herein are also useful for determining the chemosensitivity of human cancer cells to treatment with chemotherapeutic drugs. The present invention also relates to novel fluorogenic and fluorescent reporter molecules and new enzyme assay processes that can be used to detect the activity of type 2 methionine aminopeptidase, dipeptidyl peptidase IV, calpain, aminopeptidase, HIV protease, adenovirus protease, HSV-1 protease, HCMV protease and HCV protease.

41 Claims, 12 Drawing Sheets

OTHER PUBLICATIONS

Weber, J.M., "Adenovirus Endopeptidase and Its Role in Virus Infection," *Curr. Topic Microbiol. Immunol.* 199:227–235 (1995).

West, M.L. and D.P. Fairlie, "Targeting HIV–1 protease: a test of drug–design methodologies," *TiPS* 16:67–74 (1995).

Yoon, H. J. et al., "DNA topoisomerase II cleavage of telomeres in vitro and in vivo," *Biochem. et Biophys. Acta* 1395:110–120 (Jan. 1998).

Yuan, J. et al., "The *C. elegans* Cell Death Gene ced–3 Encodes a Protein Similar to Mammalian Interleukin–1β–Converting Enzyme," *Cell* 75:641–652 (1993).

Zhang, R. et al., "Probing the Substrate Specificity of Hepatitis C Virus NS3 Serine Protease by Using Synthetic Peptides," *J. Virol.* 71:6208–6213 (Aug. 1997).

Diouri, M. et al., "Cleavage Efficiency by Adenovirus Protease Is Site–dependent," *J. Biol. Chem.* 271:32511–32514 (1996).

Evans, D.B. et al., "An Ultrasensitive Human Immunodeficiency Virus Type 1 Protease Radioimmuno Rate Assay with a Potential for Monitoring Blood Levels of Protease Inhibitors in Acquired Immunodeficiency Disease Syndrome Patients," *Analyt. Biochem.* 206:288–292 (1992).

Friesen, C. et al., "Involvement of the CD95 (APO–1/Fas) receptor/ligand system in drug–induced apoptosis in leukemia cells," *Nature Med.* 2:574–577 (1996).

DiIanni, C.L. et al., "In Vitro Activity of the Herpes Simplex Virus Type 1 Protease with Peptide Substrates," *J. Biol. Chem.* 268:25449–25454 (1993).

Dinarello, C.A., "Interleukin–1 and Interleukin–1 Antagonism," *Blood* 77:1627–1652 (1991).

Ding, J. et al., "Crystal structure of the human adenovirus proteinase with its 11 amino acid cofactor," *EMBO J.* 15:1778–1783 (1996).

Haugland, R.P., "Handbook of Fluorescent Probes and Research Chemicals". Molecular Probes, Inc., Eugene, OR, pp. 28, 54 (1996).

International Search Report of International Application No. PCT/US98/21231, Feb. 1, 1999.

Assfalg–Machleidt, I., et al., "Membrane Permeable Fluorogenic Rhodamine Substrates for Selective Determination of Cathespin L," *Biol. Chem. Hoppe–Seyler* 373:433–440 (1992).

Ganesh, S., et al., "Flow Cytometric Determination of Aminopeptidase Activities in Viable Cells Using Fluorogenic Rhodamine 110 Substrates," *Cytometry* 20:334–340 (1995).

Haugland, R.P., and Johnson, I.D., "Selecting Enzymes in Living Cells Using Fluorogenic Substrates," *J. Fluorescence* 3:119–127 (1993).

Haugland, R.P., "Detecting Enzymatic Activity in Cells Using Fluorogenic Substrates," *Biotechnic & Histochem.* 70:243–251 (1995).

Johnson, A.F., et al., "Nonisotopic DNA Detection System Employing Elastase and a Fluorogenic Rhodamine Substrate," *Anal. Chem.* 65:2352–2359 (1993).

Klingel, S., et al., "Flow Cytometric Determination of Cysteine and Serine Proteinase Activities in Living Cells with Rhodamine 110 Substrates," *Meth. Cell Biol.* 41:449–459 (1994).

Leytus, S.P., et al., "Rhodamine–based compounds as fluorogenic substrates for serine proteinases," *Biochem. J.* 209:299–307 (1983).

Leytus, S.P., et al., "New class of sensitive and selective fluorogenic substrates for serine proteinases," *Biochem. J.* 215:253–260 (1983).

Molecular Probes, Inc., "Alphabetical Price List of New Products," Molecular Probes, Inc., pp. 1–4 (1994).

Morliere, P., et al., "Interaction of Tetrapyrrolic Rings with Rhodamine 110 and 123 and with Rhodamine 110 Derivatives Bearing A Peptidic Side Chain," *Biochem. Biophys. Res. Comm.* 146:107–113 (1987).

Rothe, G., et al., "Flow Cytometric Analysis of Protease Activities in Vital Cells," *Biol. Chem. Hoppe Seyler* 373:547–554 (1992).

Gamen, S. et al., "Doxorubicin–induced apoptosis in human T–cell leukemia is mediated by caspase–3 activation in a Fas–independent way," *J. Virol.* 417:360–364 (Nov. 1997).

Gao, M. et al., "The Protease of Herpes Simplex Virus Type 1 Is Essential for Functional Capsid Formation and Viral Growth," *J. Virol.* 68: 3702–3712 (1994).

Griffith, E.C. et al., "Methionine aminopeptidase (type 2) is the common target for angiogenesis inhibitors AGM–1470 and ovalicin," *Chem. Biol.* 4:461–471 (Jun. 1997).

Hickman, J.A., "Apoptosis induced by anticancer drugs," *Cancer and Metastasis Rev.* 11:121–139 (1992).

Holskin, B.P. et al., "A Continuous Fluorescence–Based Assay of Human Cytomegalovirus Protease Using a Peptide Substrate," *Analyt. Biochem.* 226:148–155 (1995).

Hyland, L.J. et al., "A Radiometric Assay for HIV–1 Protease," *Analyt. Biochem.* 188:408–415 (1990).

Joensuu, H. et al., "Bcl–2 Protein Expression and Long–Term Survival in Breast Cancer," *Am. J. Pathol.* 145:1191–1198 (1994).

Li, X. and Y.–H. Chang, "Evidence That the Human Homologue of a Rat Initiation Factor–2 Associated Protein ($p^{67}$) Is a Methonine Aminopeptidase," *Biochem. Biophys. Res. Comm.* 227:152–159 (1996).

Los, M. et al., "Requirement of an ICE/CED–3 protease for Fas/APO–1–mediated apoptsis," *Nature* 375:81–83 (1995).

Los, M. et al., "Cross–Resistance of CD95– and Drug–Induced Apoptosis as a Consequence of Deficient Activation of Caspases (ICE/Ced–3 Proteases)," *Blood* 90:3118–3129 (Oct. 1997).

Maldonado, V. et al., "Modulation of NF–κB, p53 and Bcl–2 in apoptosis induced cisplatin in HeLa cells," *Mutation Res.* 381:67–75 (Nov. 1997).

Martin, J. A. et al., "5 Inhibitors of HIV Proteinase," *Prog. Med. Chem.* 32:239–287 (1995).

Matayoshi, E.D. et al., "Novel Fluorogenic Substrates for Assaying Retroviral Proteases by Resonance Energy Transfer," *Science* 247:954–958 (1990).

McCann III, P.J. et al., "Investigation of the Specificity of the Herpes Simples Virus Type 1 Protease by Point Mutagenesis of the Autoproteolysis Sites," *J. Virol.* 68:526–529 (1994).

Miller, L.K., "Baculovirus Interaction With Host Apoptotic Pathways," *J. Cell Physiol.* 173:178–182 (Nov. 1997).

Miura, M. et al., "Induction of Apoptosis in Fibroblasts by IL–1β–Converting Enzyme, a Mammalian Homolog of the *C. elegans* Cell Death ced–3," *Cell* 75:653–660 (1993).

Mosley, B. et al., "The Interleukin–1 Receptor Binds the Human Interleukin–1α Precursor but Not the Interleukin–1β Precursor," *J. Biol. Chem.* 262:2941–2944 (1987).

O'Boyle, D. R. et al., "Identification of a Novel Peptide Substrate of HSV–1 Protease Using Substrate Phage Display," *Virology* 236:338–347 (Sep. 1997).

Oppenheim, J.J. et al., "There is more than one interleukin 1," *Immunol. Today* 7:45–56 (1986).

Richards, A.D. et al., "Sensitive, Soluble Chromogenic Substrates for HIV–1 Proteinase," *J. Biol. Chem.* 265:7733–7736 (1990).

Sin, N. et al., "The anti–angiogenic agent fumagillin covalently binds and inhibits the methionine aminopeptidase, MetAP–2," *Proc. Natl. Acad. Sci. USA* 94:6099–6103 (Jun. 1997).

Armstrong, R.C. et al., "Fas–induced Activation of the Cell Death–related Protease CPP32 Is Inhibited by Bcl–2 and by ICE Family Protease Inhibitors," *J. Biol. Chem.* 271:16850–16855 (1996).

Bonneau, P.R. et al., "Design of Fluorogenic Peptide Substrates for Human Cytomegalovirus Protease Based on Structure–Activity Relationship Studies," *Analyt. Biochem.* 255:59–65 (1998).

de Givione, F.S. and G.W. Duff, "Interleukin 1: the first interleukin," *Immunol. Today.* 11:13–19 (1990).

Adams, S.R. et al., "Biologically Useful Chelators That Take Up $Ca^{2+}$ upon Illumination," *J. Am. Chem. Soc.* 111:7957–7968 (1989).

Alnemri, E.S. et al., "Human ICE/CED–3 Protease Nomenclature," *Cell* 87:171 (1996).

An, S. and K.A. Knox, "Ligation of CD40 rescues Ramos–Burkitt lymphoma B cells from calcium ionophore– and antigen receptor–triggered apoptosis by inhibiting activation of the cysteine protease CPP32/Yama and cleavage of its substrate PARP," *FEBS Letters* 386:115–122 (1996).

Thornberry, N.A. et al., "A Combinatorial Approach Defines Specificities of Members of the Caspase Family and Granzyme B," *J. Biol. Chem.* 272:17907–17911 (Jul. 1997).

Toth, M.V. and G.R. Marshall, "A simple, continuous fluorometric assay for HIV protease," *Int. J. Peptide Protein Res.* 36:544–550 (1990).

Tyagi, S.C. and C.A. Carter, "Continuous Assay of the Hydrolytic Activity of Human Immunodeficiency Virus–1 Protease," *Analyt. Biochem.* 200:143–148 (1992).

\* cited by examiner

FLUOROGENIC OR FLUORESCENT REPORTER MOLECULES AND THEIR APPLICATIONS FOR WHOLE-CELL FLUORESCENCE SCREENING ASSAYS FOR CAPSASES AND OTHER ENZYMES AND THE USE THEREOF

This application claims benefit of provisional application Ser. No. 60/061,582 filed Oct. 10, 1997.

DESCRIPTION OF BACKGROUND ART

1. Field of the Invention

This invention is in the field of intracellular detection of enzymes using fluorogenic or fluorescent probes. The invention relates to novel fluorescent dyes and application of these dyes for the preparation of novel fluorogenic or fluorescent peptide or amino acid derivatives which are substrates of proteases and peptidases. In particular, the invention relates to novel fluorogenic or fluorescent peptide derivatives which are substrates of enzymes involved in apoptosis, such as caspases and the lymphocyte-derived serine protease Granzyme B. The invention also relates to a process for measuring the activity of caspases and other enzymes involved in apoptosis in living or dead whole cells, cell lines or tissue samples derived from any healthy, diseased, infected or cancerous organ or tissue. The invention also relates to the use of the fluorogenic or fluorescent substrates in a novel assay system for discovering or detecting inhibitors or inducers of apoptosis in compound collections or compound libraries. Furthermore, the invention relates to the use of the fluorogenic or fluorescent substrates in determining the sensitivity of cancer cells to treatment with chemotherapeutic drugs. The invention also relates to novel fluorogenic or fluorescent peptide derivatives which are substrates of exopeptidases such as arninopeptidase A and N, methionine aminopeptidase and dipeptidyl-peptidase IV, endopetidases such as calpain, proteases such as HIV proteases, HCMV protease, HSV protease, HCV protease and adenovirus protease.

2. Related Art

Organisms eliminate unwanted cells by a process variously known as regulated cell death, programmed cell death or apoptosis. Such cell death occurs as a normal aspect of animal development as well as in tissue homeostasis and aging (Glucksmann, A., *Biol. Rev. Cambridge Philos. Soc.* 26:59–86 (1951); Glucksmann, A., *Archives de Biologie* 76:419–437 (1965); Ellis et al., *Dev.* 112:591–603 (1991); Vaux et al., *Cell* 76:777–779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (PCT published application W096/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane enclosed particles containing intracellular material) (Orrenius, S., *J. Internal Medicine* 237:529–536 (1995)).

Apoptosis is achieved through an endogenous mechanism of cellular suicide (Wyllie, A. H., in *Cell Death in Biology and Pathology*, Bowen and Lockshin, eds., Chapman and Hall (1981), pp. 9–34). A cell activates its internally encoded suicide program as a result of either internal or external signals. The suicide program is executed through the activation of a carefully regulated genetic program (Wylie et al., *Int. Rev. Cyt.* 68:251 (1980); Ellis et al., *Ann. Rev. Cell Bio.* 7:663 (1991)). Apoptotic cells and bodies are usually recognized and cleared by neighboring cells or macrophages before lysis. Because of this clearance mechanism, inflammation is not induced despite the clearance of great numbers of cells (Orrenius, S., *J. Internal Medicine* 237:529–536 (1995)).

Mammalian interleukin-1β (IL-1β) plays an important role in various pathologic processes, including chronic and acute inflammation and autoimmune diseases (Oppenheim, J. H. et. al. Immunology Today, 7, 45–56 (1986)). IL-1β is synthesized as a cell associated precursor polypeptide (pro-IL-1β) that is unable to bind IL-1 receptors and is biologically inactive (Mosley et al., *J. Biol. Chem.* 262:2941–2944 (1987)). By inhibiting conversion of precursor IL-1β to mature IL-1β, the activity of interleukin-1 can be inhibited. IL-1 is also a cytokine involved in mediating a wide range of biological responses including inflammation, septic shock, wound healing, hematopoiesis and growth of certain leukemias (Dinarello, C. A., Blood 77:1627–1652 (1991); diGiovine et al., *Immunology Today* 11:13 (1990)). Interleukin-1β converting enzyme (ICE) is a protease responsible for the activation of interleukin-1β (IL-1β) (Thornberry, N. A., et al., *Nature* 356:768 (1992); Yuan, J., et al., *Cell* 75:641 (1993)). ICE is a substrate-specific cysteine protease that cleaves the inactive prointerleukin-1 to produce the mature IL-1. The genes that encode for ICE and CPP32 are members of the mammalian ICE/Ced-3 family of genes which presently includes at least twelve members: ICE, CPP32/Yama/Apopain, mICE2, ICE4, ICH1, TX/ICH-2, MCH2, MCH3, MCH4, FLICE/MACH/MCH5, ICE-LAP6 and ICEre1III. The proteolytic activity of this family of cysteine proteases, whose active site cysteine residue is essential for ICE-mediated apoptosis, appears critical in mediating cell death (Miura et al., *Cell* 75:653–660 (1993)). This gene family has recently been named caspases (Alnernri, E. S. et. al. *Cell,* 87:171 (1996)).

A death trigger, such as Tumor Necrosis Factor, FAS-ligand, oxygen or nutrient deprivation, viruses, toxins, anti-cancer drugs etc., can activate caspases within cells in a cascade-like fashion where caspases upstream in the cascade (e.g. FLICE/MACH/MCH5) can activate capsases further downstream in the cascade (e.g. CPP-32/Yama/Apopain). Activation of the caspase cascade leads to cell death.

A wealth of scientific evidence suggests that, in many diseases, the caspase cascade is activated when it shouldn't be. This leads to excessive cellular suicide and organ failure. Diseases involving inappropriate activation of the caspase cascade and subsequent cellular suicide include myocardial infarction, congestive heart failure, autoimmune diseases, AIDS, viral infections, kidney failure, liver failure, rheumatoid arthritis, ischemic stroke, neurodegenerative diseases, atherosclerosis etc. Therefore, the discovery of novel drugs that can block or inhibit the activation of the caspase cascade would have wide-ranging impact on the treatment of degenerative diseases of most, if not all, organ systems of the human body.

Caspases are also thought to be crucial in the development and treatment of cancer. There is mounting evidence that cancer cells, while containing caspases, lack parts of the molecular machinery that activate the caspase cascade (Los et al., *Blood, Vol.* 90, No 8:3118–3129 (1997)). This causes the cancer cells to lose their capacity to undergo cellular suicide and the cells become immortal—they become cancerous.

It has been shown that chemotherapeutic (anti-cancer) drugs can trigger cancer cells to undergo suicide by re-activating the dormant caspase cascade. This may be a crucial aspect of the mode of action of most, if not all, known anticancer drugs (Los et al., *Blood, Vol.* 90, No 8:3118–3129 (1997); Friesen et al., *Nat. Med* 2:574 (1996). Chemotherapeutic drugs may differ in their capacity to activate the caspase system in different classes of cancers. Moreover, it is likely that anti-cancer drugs differ in their ability to activate the caspase cascade in a given cancer (e.g. lung cancer) and in different patients. In other words, there are differences from one patient to another in the chemosensitivity of, e.g. lung cancer cells, to various anti-cancer drugs.

In summary, the excessive activation of the caspase cascade plays a crucial role in a wide variety of degenerative organ diseases, while a non-functioning caspase system is a hallmark of cancer cells. New drugs that inhibit or stimulate the caspase cascade are likely to revolutionize the treatment of numerous human diseases ranging from infectious, cardiovascular, endocrine, kidney, liver and brain diseases to diseases of the immune system and to cancer.

In order to find drugs that either inhibit or stimulate the caspase cascade, it is necessary to develop high-throughput caspase activation (HTCA) assays. These HTCA assays must be able to monitor activation or inhibition of the caspase cascade inside living or whole cells. Ideally, HTCA assays should be versatile enough to measure the caspase cascade activity inside any living or whole cell, no matter what its origin might be: Cancer cells, tumor cells, immune cells, brain cells, cells of the endocrine system, cells or cell lines from different organ systems, biopsy samples etc. Furthermore, such HTCA assays should be able to measure—within living or whole cells—the activation or inhibition of any of the caspase enzymes or any other enzymes that are involved in the caspase cascade. Developing such versatile HTCA assays represents a substantial advance in the field of drug screening.

Currently available HTCA assays do not permit inner cellular screening for compounds that can either activate or inhibit the caspase cascade. There are only cell-free, high-throughput screening assays available that can measure the activity of individually isolated caspase enzymes, or assays that can measure the activity of caspases in dead cells which have been permeabilized by osmotic shock, for example (Los et al., *Blood, Vol.* 90, No 8:3118–3129 (1997)). But these enzyme assays cannot predict the effect of a compound on the caspase cascade in living cells for the following reasons:

1.) Cell free assays, or assays using dead, permeabilized cells, cannot predict the ability of compounds to penetrate the cellular membrane. This is crucial because the caspase cascade resides in the interior of the cells. In order to be active, a compound must not only be able to modulate the caspase enzyme or enzymes, but it must also be able to penetrate the intact cell membrane. Cell-free assays or assays using dead cells are therefore unable to determine whether or not a compound will be potentially useful as a drug.

2.) Isolated caspases in cell-free assays are highly susceptible to oxidation and to compounds that can cause oxidation of the enzymes. This property of isolated caspases makes cell free caspase screening assays highly susceptible to artifacts and has precluded successful use of these assays for high-throughput screening of combinatorial (or other) chemical libraries. Previous mass screening efforts, using cell-free caspase enzyme assays, have led to discovery of numerous inhibitors which oxidize caspases, but no compound that would be useful as a potential drug. Similar difficulties have been reported by others.

3.) Numerous cellular receptors, proteins, cell constituents and cofactors—many of which are still unknown—can influence the caspase cascade in living cells. Cell-free caspase assays or assays using permeabilized, dead cells do not take into account these cellular receptors and cofactors. Because of this, it is possible that a compound identified in a cell-free or dead-cell caspase assay will not work in living cells. On the other hand, a compound that might inhibit or stimulate the caspase cascade indirectly through one of the cellular receptors or cofactors would be missed entirely in an cell-free or dead-cell caspase assay.

4.) It is highly likely that the caspase cascade functions differently in cells derived from different organs. There is growing evidence that the receptors and cofactors that influence the caspase cascade differ among cell types. Using cell-free or dead cell assays, it would be virtually impossible to identify cell-type or organ specific modulators of the caspase cascade.

A potentially important application of a HTCA assay system for measuring intracellular caspase enzymes or any other enzymes involved in apoptosis is chemosensitivity testing of human cancers. It is known that there is a genetic difference in the susceptibility of human cancers to the currently marketed anti-cancer drugs: For example, lung cancer cells in one patient might be sensitive to Drug A, while another patient's lung cancer might be insensitive to Drug A, but sensitive to Drug B. This pharmacogenetic difference in chemosensitivity of cancer cells from different individuals is a well-known phenomenon.

In the past, attempts have been made to determine the chemosensitivity of cancer cells taken from individual patients prior to designing a treatment regimen with one or more of the marketed anti-cancer drugs. However, chemosensitivity testing has not found wide-spread use, because the procedures involved have some inherent technical difficulties: The testing is very time consuming (six or more days per screen) and it requires culturing of the cells prior to screening. The cell culture leads to clonal selection of cells and the cultured cells are then no longer representative of the cancer in the patient. A HTCA assay system for quickly measuring intracellular caspase activity could be used to determine very rapidly the chemosensitivity profile of freshly excised cancer cells. If the assay has a high throughput, it would be feasible to test chemosensitivity of multiple samples taken from the same patient, e.g. from different metastases. This information could then be used to design a treatment regimen using combinations of marketed anti-cancer drugs to which the cells showed greatest sensitivity.

It is clear that the need exists for HTCA assays and reagents for such assays that can be employed in drug discovery or diagnostic procedures to quickly detect and measure the activity of compounds that activate or inhibit the caspase cascade or other enzymes involved in apoptosis in the interior of living or dead whole cells. A reagent for this type of cell assay ideally should meet the following conditions: a) there should be a big difference in fluorescence signal between peptide-reporter molecule and reporter molecule after the amide bond in peptide-reporter is cleaved by the caspases or other enzymes involved in apoptosis, preferably the peptide-reporter molecule should be non-fluorescent and most preferably the peptide-reporter molecule should be non-fluorescent and colorless; b) the peptide-reporter molecule should be cell permeable, therefore there should be minimum numbers of hydrophilic groups in the molecule and the size of the molecule should preferably be small; c) the peptide-reporter molecule should preferably not diffuse out of the cell once it permeates the cell membrane; d) the reporter molecule should preferably not diffuse out of the cell once it is liberated from the peptide.

The method of screening apoptosis inhibitors or inducers in whole cells vs cell-free enzyme assay can also be used for the screening of inhibitors of enzymes other than caspases. Traditionally, enzyme inhibitors were first identified by cell-free enzyme assays. Cell cultures were then used for secondary assay to assess activity of the active compounds in intact cells. A cell permeable fluorogenic or fluorescent substrate will enable the screening of inhibitors of proteases and peptidases and other enzymes directly in living whole cells. There are several advantages in whole cell assays vs cell-free enzyme assays. One of the advantages is that in whole cell assays, the inhibitor will have to penetrate the cell to be detected. Since many proteases in living cells are regulated by other proteins, receptors or genes, screening using living cells will allow the identification of small molecule compounds which interfere with cellular proteases by binding to the active site, as well as compounds which modulate protease function by interfering with transcription, translation, biosynthesis, sub-unit assembly, cellular cofactors or signal transduction mechanisms (or viral entry into host cells, in the case of viral proteases). Furthermore, since there is an abundance of aminopeptidases in the cells, these aminopeptidases can be used in the design of fluorogenic or fluorescent substrates for whole cell assay which otherwise will not work in cell-free enzyme assays. Therefore there is a need to develop high throughput screening (HTS) assays and reagents for such assays in whole cells which can be used for drug discovery or diagnostic procedures.

AGM-1470 (also known as TNP-470) is an angiogenesis inhibitor in clinical trials for a variety of cancers. The mechanism of action of AGM-1470 was recently discovered by two independent research groups (Sin, N., et al. *Proc. Natl. Acad. Sci. U.S.A.* 94:6099–6103 (1997); Griffith, E. C., et al., *Chem. Biol.* 4:461–471 (1997)). They found that AGM-1470 and analogs are inhibitors of methionine aminopeptidase type 2 (MetAP-2). The potency for inhibition of endothelial cell proliferation and inhibition of methionine aminopeptidase activity was determined for a series of AGM-1470 analogs and a significant correlation between the two activities was found.

Since angiogenesis inhibitors are known to be able to selectively kill cancer cells, a cellular screening assay for inhibitors of MetAP-2 may result in novel anti-cancer drugs. Therefore cell permeable fluorogenic or fluorescent substrates for MetAP-2 can be used for the screening of inhibitors of MetAP-2 in endothelial cells which could lead to novel anticancer agents.

Recently, HIV protease inhibitors such as ritonavir and viracept have been shown to be very effective in the treatment of patients infected with HIV. These inhibitors were designed based on the structure of the HIV protease substrate. The activities of these inhibitors were first determined against HIV protease. Active compounds were then tested for inhibition of HIV infection in cell cultures. A cell permeable fluorogenic or fluorescent substrate for HIV protease can be used for the screening of HIV protease inhibitors in HIV infected cells which could speed up the process for the discovery of novel HIV protease inhibitors and lead to new and better treatment for HIV infection. Since HIV protease processes viral precursor proteins at a late stage in viral replication, a cell permeable fluorogenic or fluorescent substrate for HIV protease also can be used to screen compounds which inhibit gene transcription or translation, viral entry, or other key proteins in the early stage of HIV infection. The fluorogenic or fluorescent substrates also could be used for diagnosis of HIV infection, which might be more sensitive than the currently available methods.

Applying the same principle, cell permeable fluorogenic or fluorescent substrates for cathepsin B can be used for the screening of cathepsin B inhibitors. Cell permeable fluorogenic or fluorescent substrates for dipeptidyl-peptidase IV can be used for the screening of dipeptidyl-peptidase IV inhibitors. Cell permeable fluorogenic or fluorescent substrates for renin can be used for the screening of renin inhibitors and cell permeable fluorogenic or fluorescent substrates for adenovirus protease or other viral proteases can be used for the screening of adenovirus protease or other viral protease inhibitors.

U.S. Pat. Nos. 4,557,862 and 4,640,893 disclose Rhodamine 110 derivatives as fluorogenic substrates for proteinases of the formula:

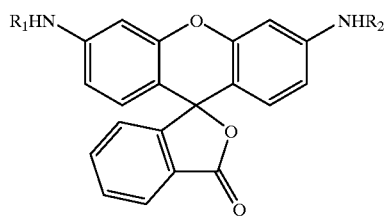

wherein $R_1$ and $R_2$, which are the same or different, are selected from the group consisting of amino acids, amino acid derivatives, blocked amino acids, blocked amino acid derivatives, and peptides. Exemplary $(AA)_2$-Rhodamines and (peptide)$_2$-Rhodamines are (Z-Arg)$_2$-Rhodamine 110, (Arg)$_2$-Rhodamine 110, (Z-Ala-Arg)$_2$-Rhodamine 110, (Z-GlN-Arg)$_2$-Rhodamine 110, (Z-Glu-Arg)$_2$-Rhodamine 110, (Z-Gly-Arg)$_2$-Rhodamine 110, (Z-Leu-Arg)$_2$-Rhodamine 110, (Z-Met-Arg)$_2$-Rhodamine 110, (Z-Phe-Arg)$_2$-Rhodamine 110, (Z-Pro-Arg)$_2$-Rhodamine 110, (Z-Trp-Arg)$_2$-Rhodamine 110, (Z-Val-Arg)$_2$-Rhodamine 110, and (Z-Ile-Pro-Arg)$_2$-Rhodamine 110.

WO 96/36729 discloses compounds or their salts for assaying the activity of an enzyme inside a metabolically active whole cell. The assay compound is said to include a leaving group and an indicator group. The leaving group is selected from the group comprising amino acids, peptides, saccharides, sulfates, phosphates, esters, phosphate esters, nucleotides, polynucleotides, nucleic acids, pyrimidines, purines, nucleosides, lipids and mixtures. The indicator group is selected from compounds which have a first state when joined to the leaving group, and a second state when the leaving group is cleaved from the indicator group by the enzyme. Preferred indicator compounds are said to be Rhodamine 110, rhodol, and fluorescein and analogs of these compounds. The patent application listed many enzymes and substrates of enzymes.

U.S. Pat. No. 5,576,424 disclosed haloalkyl derivatives of reporter molecules used to analyze metabolic activity in cells of the formula:

XR-SPACER-REPORTER-BLOCK

Wherein—BLOCK is a group selected to be removable by action of a specific analyte, to give reporter spectral properties different from those of the substrate;—REPORTER— is a molecule that, when no longer bound to BLOCK by a BLOCK—REPORTER bond, has spectral properties different from those of the substrate;—SPACER—is a covalent linkage; and XR—is a haloalkyl moiety that can covalently react with an intracellular thiol to form a thioether conjugate. Preferred reporter compounds are said to include Rhodamine-110, rhodol, fluorescein and others.

SUMMARY OF THE INVENTION

The invention relates to fluorogenic or fluorescent reporter compounds of Formula I:

$$x\text{-}y\text{-}z \qquad \qquad I$$

or biologically acceptable salts or pro-reporter molecules (such as methyl ester form of carboxyl-containing amino acid residues) thereof, wherein x and z is the same or different and is a peptide or amino acid or acyl group or other structure such that compounds of Formula I is a substrate for caspases, or a substrate for other proteases or peptidases or other enzymes; and wherein the scissile bond is only one or both of the x-y and y-z bonds in Formula I when x is the same as z, or wherein the scissile bond is only one of the x-y or y-z bond in Formula I when x is not the same as z. y is a fluorogenic or fluorescent moiety.

Preferred compounds are represented by Formula II:

$$R_1\text{-}(AA)_n\text{-}Asp\text{-}y\text{-}Asp\text{-}(AA)_n\text{-}R_1 \qquad \qquad II$$

or biologically acceptable salts or pro-reporter molecules (such as methyl ester form of carboxyl-containing amino acid residues) thereof, wherein $R_1$ is an N-terminal protecting group such as t-butyloxycarbonyl, acyl, and benzyloxycarbonyl; each AA independently is a residue of any natural or non-natural natural α-amino acid or β-amino acid, or derivatives of an α-amino acid or β-amino acid; each n is independently 0–5; and y is a fluorogenic or fluorescent moiety. Preferred y is a Rhodamine including Rhodamine 110, Rhodamine 116 and Rhodamine 19. Most preferred y is Rhodamine 110.

Especially preferred compounds are represented by Formula III:

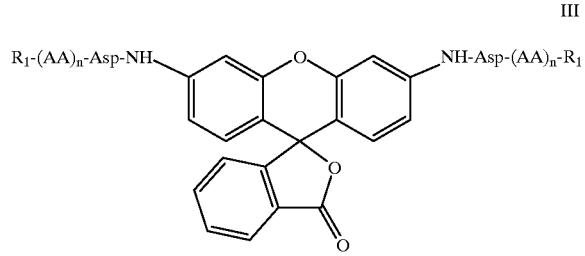

III or biologically acceptable salts or pro-reporter molecules (such as methyl ester form of carboxyl-containing amino acid residues) thereof, wherein $R_1$, AA, n are as defined previously in formula II. Preferred $R_1$ is t-butyloxycarbonyl, acyl and benzyloxycarbonyl. Preferred values of n are 1–3.

The invention also relates to a method for the preparation of a compound of Formula III, comprising (a) condensing Rhodamine together with N-fmoc-L-aspartic acid β-t-butyl ester to give (Fmoc-Asp(OBu-t))$_2$-Rhodamine;

(b) removing the Fmoc group to give (Asp(OBu-t))$_2$-Rhodamine;

(c) condensing (Asp(OBu-t))$_2$-Rhodamine with Z-(AA)$_n$ to give (Z-(AA)$_n$-Asp(OBu-t))$_2$-Rhodamine; and (d) removing the OBu-t protecting group.

In a preferred embodiment, -(AA)$_n$ is WEH SEQ ID NO:1, YVA SEQ ID NO:2, LEH SEQ ID NO:3, DET SEQ ID NO:4, DEV SEQ ID NO:5, DEH SEQ ID NO:6, VEH SEQ ID NO:7, LET SEQ ID NO:8, LEV SEQ ID NO:9, SHV SEQ ID NO: 10, DEL SEQ ID NO:11, DGP SEQ ID NO:12, DEP SEQ ID NO:13, DGT SEQ ID NO:14, DLN SEQ ID NO:15, DEE SEQ ID NO:16, DSL SEQ ID NO:17, DVP SEQ ID NO:18, DEA SEQ ID NO:19, DSY SEQ ID NO:20, ELP SEQ ID NO:21, VED SEQ ID NO:22, IEP SEQ ID NO:23 or IET SEQ ID NO:24, and the carboxy containing amino acids are protected with an OBu-t group which is removed in the final step.

Another group of preferred compounds falling within the scope of Formula I include compounds wherein x is not the same as z. Preferred compounds of this group include those wherein x is a peptide or other structure which makes the compound a substrate for caspases, or a substrate for other proteases or peptidases or other enzymes; and the x-y bond in Formula I is the scissile bond under biological conditions. z is a blocking group and the y-z bond in Formula I is not a scissile bond under biological conditions.

Specifically, the novel fluorogenic or fluorescent reporter compounds of this invention are of Formula V:

$$R_1\text{-} (AA)_n\text{-}Asp\text{-}y\text{-}R_6 \qquad \qquad V$$

or biologically acceptable salts or pro-reporter molecules (such as methyl ester form of carboxyl-containing amino acid residues) thereof, wherein: $R_1$, AA, n and y are as defined previously in formula II; and $R_6$ is a blocking group which is not an amino acid or a derivative of an amino acid.

In particular, preferred embodiments of the compounds of Formula V are represented by Formula VII:

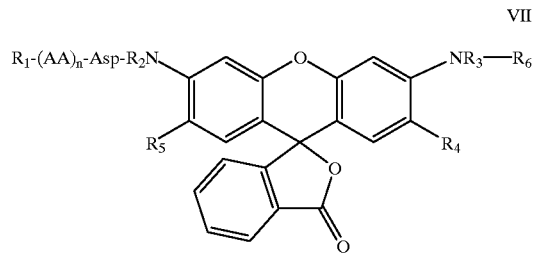

VII or biologically acceptable salts or pro-reporter molecules (such as methyl ester form of carboxyl-containing amino acid residues) thereof, wherein $R_1$, $R_6$, AA and n are as defined previously in Formulae II and V;

$R_2$ and $R_3$ are the same or different and are independently hydrogen, alkyl or aryl; and $R_4$ and $R_5$ are the same or different and are independently hydrogen or alkyl.

Another group of preferred embodiments of the compounds of Formula I are represented by Formula VIII:

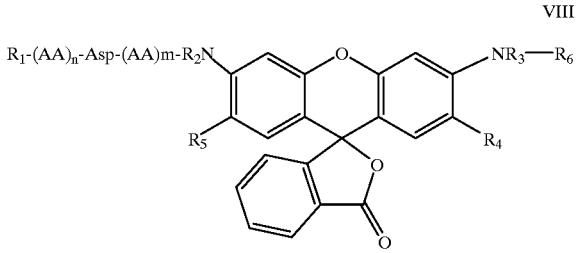

VIII or biologically acceptable salts or pro-reporter molecules (such as methyl ester form of carboxyl-containing amino acid residues) thereof, wherein $R_1$, $R_6$, AA and n are as defined previously in Formulae II and V; m is an integer from 0–3.

$R_2$ and $R_3$ are the same or different and are independently hydrogen, alkyl or aryl; and $R_4$ and $R_5$ are the same or different and are independently hydrogen or alkyl.

Yet another group of preferred embodiments of the compounds of Formula I are represented by Formula IX:

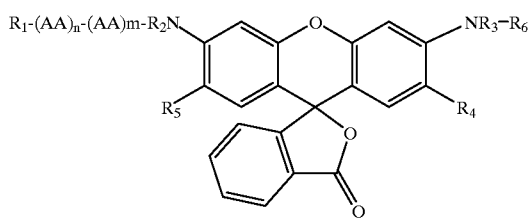

IX or biologically acceptable salts or pro-reporter molecules (such as methyl ester form of carboxyl-containing amino acid residues) thereof, wherein $R_1$, $R_6$, AA and n are as defined previously in Formulae II and V; m is an integer from 0–3.

$R_2$ and $R_3$ are the same or different and are independently hydrogen, alkyl or aryl; and $R_4$ and $R_5$ are the same or different and are independently hydrogen or alkyl.

The invention also relates to a method for the preparation of a compound of Formula VII, comprising (a) reacting Rhodamine with acetic anhydride to give N-acetyl-Rhodamine of Formula VI;

(b) condensing N-acetyl-Rhodamine of Formula VI together with N-fmoc-L-aspartic acid β-t-butyl ester to give N-(Fmoc-Asp(OBu-t))-N'-acetyl-Rhodamine;

(c) removing the Fmoc group to give N-(Asp(OBu-t))-N'-acetyl-Rhodamine;

(d) condensing N-(Asp(OBu-t))-N'-acetyl-Rhodamine with Z-(AA)$_n$ to give N-(Z-(AA)$_n$-Asp(OBu-t))-N'-acetyl-Rhodamine; and (e) removing the OBu-t protecting group to give N-(Z-(AA)$_n$-Asp)-N'-acetyl-Rhodamine; or alternatively (a) reacting Rhodamine with acetic anhydride to give N-acetyl-Rhodamine of Formula VI;

(b) condensing N-acetyl-Rhodamine of Formula VI with Z-(AA)$_n$-Asp(β-OBu-t) to give N-(Z-(AA)$_n$-Asp(OBu-t))-N'-acetyl-Rhodamine; and (c) removing the OBu-t protecting group to give N-(Z-(AA)$_n$-Asp)-N'-acetyl-Rhodamine.

In this embodiment, where (AA)$_n$ includes amino acids such as glutamic acid or aspartic acid, the carboxy group is protected as an OBu-t group which is cleaved in the last step.

Thus, the invention also relates to the novel fluorescent dyes of Formula VI which are derivatives of Rhodamines. These compounds are prepared by introducing a blocking group $R_6$ into one of the two amino groups of Rhodamine. The $R_2$HN group in Formula VI provides the point of attachment for reaction with a potential enzyme substrate, such as the carboxylic group of a N-blocked peptide, to form a peptide amide bond. The reaction will convert the fluorescent molecule of Formula VI into a non-fluorescent peptide-reporter molecule of Formulae VII–IX which is a substrate for a protease or peptidase. Cleavage of the scissile peptide-reporter amide bond in peptide-reporter by proteases or peptidases produces compound of Formula VI or VI' which is fluorescent.

Specifically, the novel fluorescent dyes of this invention are of Formula VI:

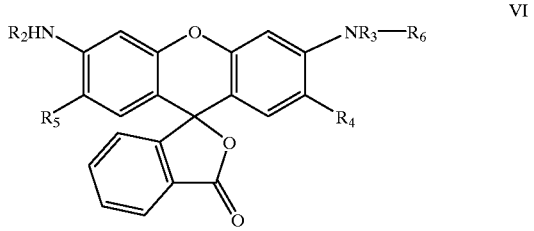

VI or biologically acceptable salts wherein:

$R_2$ and $R_3$ are the same or different and are independently hydrogen, alkyl or aryl;

$R_6$ is a blocking group which is not an amino acid or a derivative of an amino acid;

$R_4$ and $R_5$ are the same or different and are independently hydrogen or alkyl.

Preferred $R_2$ and $R_3$ are hydrogen, methyl or ethyl; Preferred $R_4$ and $R_5$ are hydrogen or methyl.

The invention also relates to a process of using the reporter compounds represented by Formula I to measure the activity of intracellular caspases or other enzymes involved in apoptosis in living or dead whole cells or tissues. The invention also relates to methods of using the compounds represented by Formula I and the assay processes described herein to measure the activation or inhibition of any of the caspase enzymes inside any living or dead whole cell or tissue (normal or cancerous) by a test substance or substances. The compounds represented by Formula I are cell-permeable, that is, they can be introduced into whole cells or tissue samples. The compounds are fluorogenic or fluorescent and can be designed to be specific for any of the known caspases or for any other intracellular enzymes involved in apoptosis.

Thornberry, N. A., et al., *J. Biol Chem.* 272:17907 (1997), describe the optimal sequences for various caspase substrates and for the Granzyme B substrate. The optimal substrate sequences are shown in Table 1.

TABLE 1

| Enzyme* | Optimal Sequence** |
|---|---|
| caspase-1 (ICE) | WEHD (SEQ ID NO: 1) |
| caspase-2 (ICH-1, mNEDD2) | DEHD (SEQ ID NO: 6) |
| caspase-3 (apopain, CPP-32, YAMA) | DEVD (SEQ ID NO: 5) |

TABLE 1-continued

| Enzyme* | Optimal Sequence** |
|---|---|
| caspase-4 (ICE$_{rel}$-II, TX, ICH-2) | (W/L) EHD (SEQ ID NO: 25) |
| caspase-5 (ICE$_{rel}$-III, TY) | (W/L) EHD (SEQ ID NO: 25) |
| caspase-6 (Mch2) | VEHD (SEQ ID NO: 7) |
| caspase-7 (Mch-3, ICE-LAP3, CMH-1) | DEVD (SEQ ID NO: 5) |
| caspase-8 (MACH, FLICE, Mch5) | LETD (SEQ ID NO: 8) |
| caspase-9 (ICE-LAP6, Mch6) | LEHD (SEQ ID NO: 3) |
| granzyme B | IEPD (SEQ ID NO: 23) |

*Enzymes are identified by both new and old (in parentheses) nomenclature.
**Standard one-letter abbreviations for amino acids are used to indicate the optimal amino acid sequences.

Using the optimal sequences described by Thornberry et al., fluorogenic or fluorescent substrates for specific caspases can be synthesized by the procedures described herein.

It is also possible to design other fluorogenic or fluorescent substrates for known or unknown caspases by utilizing known or potential cleavage site peptide sequences from known or potential natural substrates of caspase enzymes. Table 2 depicts peptide sequences corresponding to known or potential cleavage sites in proteins that may be natural substrates for caspases.

TABLE 2

| Enzyme | Substrate | Cleavage Sequence* |
|---|---|---|
| Caspase-3 | PARP | DEVD (SEQ ID NO: 5) |
| | PAK2 | SHVD (SEQ ID NO: 10) |
| | D4-GDI | DELD (SEQ ID NO: 11) |
| | U1-70kDa | DGPD (SEQ ID NO: 12) |
| | SREBP | DEPD (SEQ ID NO: 13) |
| | DNA-PK | DEVD (SEQ ID NO: 5) |
| | Huntingtin | DGTD (SEQ ID NO: 14) |
| | | DLND (SEQ ID NO: 15) |
| | | DEED (SEQ ID NO: 16) |
| | | DSLD (SEQ ID NO: 17) |
| | mdm2 | DVPD (SEQ ID NO: 18) |
| caspase-3 + other unknown caspases | fodrin | DETD (SEQ ID NO: 4) |
| Possibly caspase-3 | Rb | DEAD (SEQ ID NO: 19) |
| Possibly caspase-3 | Presenilins | DSYD (SEQ ID NO: 20) |
| ? | actin | ELPD (SEQ ID NO: 21) |
| Caspase-6 | Lamin A | VEID (SEQ ID NO: 26) |
| Caspase-8 | CPP32 | IETD (SEQ ID NO: 24) |

*Standard one-letter abbreviations for amino acids are used to indicate the amino acid sequences.

The fluorogenic or fluorescent substrates can also be designed to measure more than one enzyme at a time, by designing substrates that are recognized and cleaved by more than one of the enzymes involved in the caspase cascade. Fluorogenic or fluorescent substrates which are "promiscuous" for more than one caspase may be utilized using the assay process described herein to measure the activity of as yet unknown caspases.

When the caspase cascade is activated by a cell-death inducing stimulus, the fluorogenic or fluorescent reporter molecules described herein are cleaved and respond with a large increase in fluorescence emission. The change in fluorescence can be measured spectrofluorometrically. The reporter molecules can also be used to measure baseline caspase activity in cells that are not undergoing apoptosis. The method is easily adaptable to high throughput or ultra-high throughput screening assays.

The assay system is very versatile. Examples of the extreme versatility of the assay system are given below:

1. The assay can be used to screen a cell or tissue for baseline activity of any caspase enzyme or any other enzyme involved in apoptosis.
2. The assay can be used with equal ease to screen for compounds that can either activate or inhibit the caspase cascade. That means the assay can be used to screen for drugs against degenerative diseases or for drugs against cancer.
3. The assay can be used to screen for caspase cascade activation or inhibition in any living or dead cells or cell lines derived from any organ system in the body including, but not limited to, hair, brain, peripheral nervous system, eye, ear, nose, mouth, tonsils, teeth, esophagus, lung, heart, blood, blood vessels, bone marrow, lymph nodes, thymus, spleen, immune system, liver, stomach, intestinal tract, pancreas, endocrine glands and tissues, kidney, bladder, reproductive organs and glands, joints, bones and skin. The assay can be used to screen for drugs with potential use in any disease of any organ system in the body that involves malfinction of the caspase cascade.
4. The assay can be used to screen for drugs that might modulate the caspase cascade directly or indirectly, i.e. by modulating the caspases itself or by modulating cellular receptors and co-factors that influence the caspase cascade.
5. The assay can be used to determine the site of action at which a caspase cascade modulator interferes. That is, the assay can help to pin down the molecular mechanism of action of a novel caspase cascade modulator drug.

The invention also relates to the use of the fluorogenic or fluorescent substrates represented by Formula I for finding new compounds or new uses for known compounds in reducing, preventing or treating maladies in which apoptotic cell death is either a causative factor or a result. Examples of uses for the present invention include screening for compounds that can protect the nervous system following focal ischemia and global ischemia; screening for compounds that can treat neurodegenerative disorders such as Alzheimer's disease, Huntington's Disease, prion diseases, Parkinson's Disease, multiple sclerosis, amyotrophic lateral sclerosis, ataxia, telangiectasia, and spinobulbar atrophy; screening for compounds that can treat heart disease including myocardial infarction, congestive heart failure and cardiomyopathy; screening for compounds that can treat retinal disorders; screening for compounds that treat autoimmune disorders including lupus erythematosus, rheumatoid arthritis, type I diabetes, Sjögren's syndrome and glomerulonephritis; screening for compounds that treat polycystic kidney disease and anemia/erythropoiesis; screening for compounds that treat immune system disorders, including AIDS and SCIDS; screening for compounds that reduce or prevent cell, tissue and organ damage during transplantation (e.g. graft versus host disease in bone marrow transplantation procedures); screening for compounds that reduce or prevent cell line death in industrial biotechnology; screening for compounds that reduce or prevent alopecia (hair loss); and screening for compounds that reduce the premature death of skin cells.

The present invention also relates to the use of the fluorogenic or fluorescent substrates represented by Formula I in screening procedures where libraries of known drugs or combinatorial or other compound libraries are screened for compounds with anti-tumor or anti-cancer activity. The cancer cells or cell lines can be derived from any cancer of any internal or external organ system in the body including, but not limited to brain, peripheral nervous system, eye, ear, nose, mouth, tonsils, teeth, esophagus, lung, heart, blood, blood vessels, bone marrow, lymph nodes, thymus, spleen, immune system, liver, stomach, intestinal tract, pancreas, endocrine glands and tissues, kidney, bladder, reproductive organs and glands (e.g. prostate gland), joints, bones and skin.

The present invention also relates to the use of the fluorogenic or fluorescent substrates represented by Formula I in diagnostic procedures to determine the chemosensitivity or resistance of cancer cells taken from an animal or a human being to treatment with chemotherapeutic drugs. The cancer cells or cell lines can be derived from any cancer of any internal or external organ system in the body including, but not limited to brain, peripheral nervous system, eye, ear, nose, mouth, tonsils, teeth, esophagus, lung, heart, blood, blood vessels, bone marrow, lymph nodes, thymus, spleen, immune system, liver, stomach, intestinal tract, pancreas, endocrine glands and tissues, kidney, bladder, reproductive organs and glands (e.g. prostate gland), joints, bones and skin.

In particular, the invention relates to a method for detecting an enzyme involved in the apoptosis cascade in one or more cells, comprising (a) contacting the one or more cells with a reporter compound according to the invention under conditions whereby the reporter compound is taken into said one or more cells, and (b) recording the fluorescence of said one or more cells, wherein a change in fluorescence, either of magnitude (i.e. increase) or of wave length, within the one or more cells compared to control cells which have not been so contacted or one that has been contacted with the reporter compound and a known competitive inhibitor of the enzyme, is an indication of the presence of the enzyme.

The invention also relates to a method for measuring the activity of an enzyme involved in the apoptosis cascade in one or more cells, comprising (a) contacting the one or more cells with the reporter compound according to the invention under conditions whereby said reporter compound is taken into the one or more cells, and (b) recording the fluorescence of the one or more cells, wherein the relative change in fluorescence, either of magnitude or of wave length within the one or more cells, compared to control cells which have not been so contacted or one that has been contacted with the reporter compound and a known competitive inhibitor of the enzyme, is a measure of the activity of the enzyme.

The invention also relates to a method for determining whether a test substance has an effect on an enzyme involved in the apoptosis cascade in one or more test cells, comprising (a) contacting the one or more test cells with the test substance and the reporter compound according to the invention under conditions whereby the reporter compound is taken into the one or more cells and the test substance either interacts with an external membrane receptor or is taken into said cells, and (b) recording the fluorescence of the test cells, wherein a change in fluorescence, either of magnitude or of wavelength, within the cells compared to the control cells which have only been contacted with the reporter compound and not with the test substance, is an indication that the test substance has an effect either directly or indirectly on the apoptosis enzyme being tested.

In the practice of this aspect of the invention, the test cells may be contacted with said test substance prior to, after, or substantially simultaneously with the reporter compound according to the invention. The method may be used to detect whether the test substance stimulates or inhibits the activity of the enzyme.

The invention also relates to further contacting the test cells with a second test substance or mixture of test substances in the presence of the first test substance.

In a preferred embodiment, the test cell is a cancer cell or cell line derived from a human in need of treatment with a chemotherapeutic drug and the test substance is a chemotherapeutic agent or a mixture of chemotherapeutic agents.

The invention also relates to a method to determine the sensitivity of an animal with cancer to treatment with one or more chemotherapeutic agents, comprising (a) contacting cancer cells taken from said animal with one or more chemotherapeutic agents and the reporter compound according to the invention under conditions whereby the reporter compound is taken into the cancer cells and the one or more drugs either interact with an external membrane receptor or are taken into the said cell, and (b) recording the fluorescence of the cancer cells, wherein a change in fluorescence, either of magnitude or of wavelength, within the cancer cells compared to control cells which have only been contacted with the reporter compound, is an indication that the cancer cells are chemosensitive to the one or more agents and that the animal is sensitive to the treatment.

The invention also relates to a method to monitor the treatment of an animal with one or more chemotherapeutic drugs, comprising (a) administering one or more chemotherapeutic drugs to the animal, (b) contacting cells taken from the animal after administering the reporter compound according to the invention under conditions whereby the reporter compound is taken into the cells, and (c) recording the fluorescence of the cells contacted with the reporter compound, wherein a change in fluorescence, either of magnitude or of wavelength, within the cells taken from the animal after administering compared to the control cells which have been taken from the animal before the administration is an indication that the animal is sensitive to the chemotherapeutic agent. In this embodiment, the animal may suffer from a malady in which apoptotic cell death is either a causative factor or a result.

The invention also relates to a method for determining whether a test substance inhibits or prevents cell death in one or more test cells, comprising (a) contacting the test cell with the test substance and the reporter compound according to the invention under conditions whereby the test substance either interacts with an external membrane receptor or is taken into the cell and the reporter compound is taken into the cell, and (b) recording the fluorescence of the test cells, wherein a change in fluorescence, either of magnitude or of wavelength, within the test cells compared to control cells that have only been contacted with the reporter compound, is an indication that the test substance inhibits or prevents cell death.

The invention also relates to a method for determining whether a test substance causes or enhances cell death in one or more test cells, comprising (a) contacting the test cells with the test substance and the reporter compound according to the invention under conditions whereby the test substance either interacts with an external membrane receptor or is taken into the cells and the reporter compound is taken into the cells, (b) recording the fluorescence of the test cells, wherein a change in fluorescence, either of magnitude or of wavelength, within the test cells compared to control cells which have only been contacted with the reporter compound, is an indication that the test substance causes or enhances cell death.

The invention also relates to a process of using the reporter compounds represented by Formula IX to measure the activity of intracellular peptidases and proteases in living whole cells, including, but not limited to, type-2 methionine aminopeptidase in endothelial cells and HIV protease in HIV infected cells. The invention also relates to methods of using the compounds represented by Formula IX and the assay processes described herein to measure the inhibition or activation of enzymes inside living whole cell by a test compound or compounds. The reporter compounds represented by Formula IX are cell-permeable, that is they can be introduced into whole cells. The compounds are fluorogenic or fluorescent and can be designed to be specific for the known enzymes of interest, such as methionine aminopeptidase or HIV protease.

The invention also relates to a method for detecting a viral protease in one or more cells, comprising (a) contacting the cells with the reporter compound according to the invention under conditions whereby the reporter compound is taken into the cells, and (b) recording the fluorescence of said cells, wherein a change or increase in fluorescence within the cells compared to control cells which have not been so contacted is an indication of the presence of the viral protease.

The invention also relates to a method for measuring the activity of a viral protease in one or more viral infected cells, comprising (a) contacting the one or more viral infected cells with the reporter compound according to the invention under conditions whereby the reporter compound is taken into the one or more viral infected cells, and (b) recording the fluorescence of said one or more cells, wherein a change or increase in fluorescence within the one or more viral infected cells compared to control cells which have not been so contacted is a measure of the activity of the viral protease.

The invention also relates to a method for determining whether a test substance has an effect on the activity of viral protease in one or more viral infected cells, comprising (a) contacting the viral infected test cells with the test substance and the reporter compound according to the invention under conditions whereby said reporter compound is taken into the infected test cells, and (b) recording the fluorescence of the infected test cells compared to infected control cells which have only been contacted with the reporter compound, wherein a change or increase in fluorescence within the infected test cells compared to the infected control cells is an indication that the test substance has an effect, on the viral protease.

In a preferred embodiment, the cells are HIV infected cells and the viral protease is HIV protease. In another preferred embodiment, the cells are adenovirus infected cells and the viral protease is adenovirus protease. In another preferred embodiment, the cells are HSV infected cells and the viral protease is HSV protease. In another preferred embodiment, the cells are HCMV infected cells and the viral protease is HCMV protease. In another preferred embodiment, the cells are HCV infected cells and the viral protease is HCV protease.

The invention also relates to a method for measuring the activity of protease or peptidase in cells, comprising (a) contacting the test cells with the reporter compound according to the invention under conditions whereby the reporter compound is taken into the test cells, or the reporter compound is interacting with an external membrane protease or peptidase of said cells, and (b) recording the fluorescence of the cells, wherein a change or increase in fluorescence within the test cell compared to control cells which have not been so contacted is a measure of the activity of the the protease or peptidase.

The invention also relates to a method for determining whether a test substance has an effect on the activity of protease or peptidase in the test cells, comprising (a) contacting the test cells with the test substance and the reporter compound according to the invention under conditions whereby the reporter compound is taken into the test cells, or the reporter compound is interacting with an external membrane protease or peptidase of the cells, and (b) recording the fluorescence of the test cells compared to control cells which have only been contacted with the reporter compound, wherein a change or increase in fluorescence within the test cells compared to the control cells is an indication that the test substance has an effect on the protease or peptidase.

In a preferred embodiment, the cells are endothelial cells and the peptidase is type 2 methionine aminopeptidase. In anther preferred embodiment, cells are T cells and the peptidase is dipeptidyl peptidase-IV. In another preferred embodiment, the cells are neuron cells and the protease is calpain.

DETAILED DESCRIPTION OF THE INVENTION

Figure 1A:
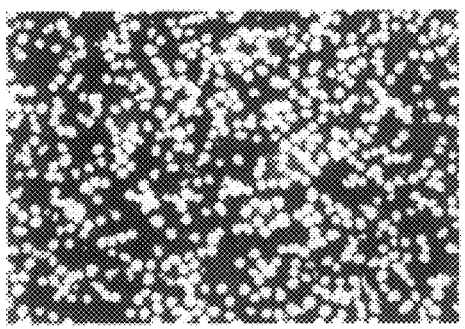
FIGS. 1A–1F depict photographs of HL-60 cells stained by N-octyloxycarbonyl-Rhodamine 110 (FIG. 1A), N-decyloxycarbonyl-Rhodamine-110 (FIG. 1B), N-dodecyloxycarbonyl-Rhodamine-110 (FIG. 1C), N-hexyloxycarbonyl-Rhodamine-110 (FIG. 1D), N-(ethylthio)carbonyl-Rhodamine 110 (FIG. 1E) and Rhodamine 110 (FIG. 1F).
Figure 1B:
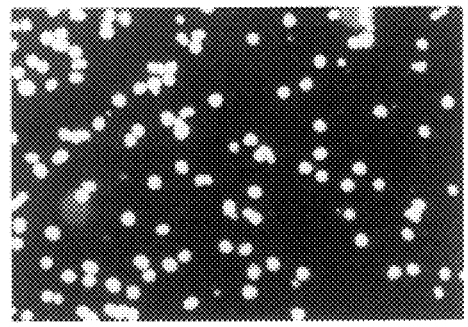
Figure 1C:
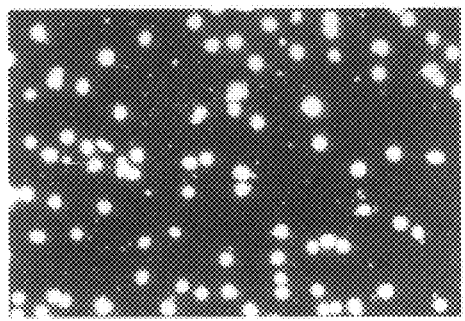
Figure 1D:
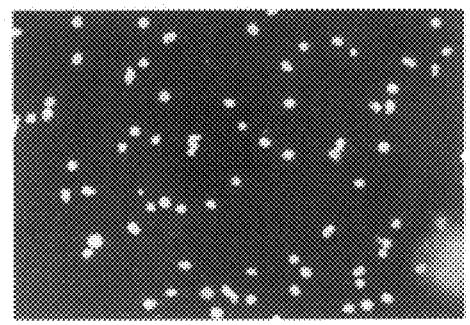
Figure 1E:
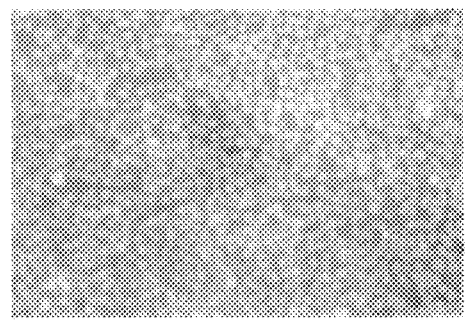
Figure 1F:
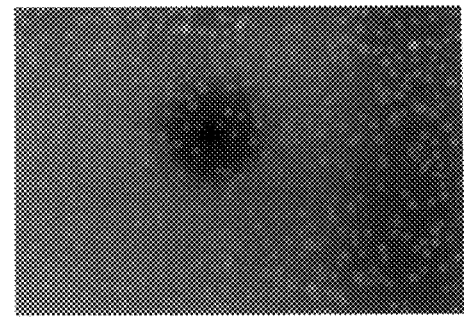

The fluorogenic or fluorescent substrates of the present invention are compounds having the general Formula I:

x-y-z  I or biologically acceptable salts or pro-reporter molecules (such as methyl ester form of carboxyl-containing amino acid residues) thereof, wherein x and z is the same or different and is a peptide or amino acid or acyl group or other structure such that Formula I is a substrate for caspases, or other proteases or peptidases or other enzymes; and wherein the scissile bond is only one or both of the x-y and y-z bonds in Formula I when x is the same as z, or wherein the scissile bond is only one of the x-y or y-z bonds in Formula I when x is not the same as z. y is a fluorogenic or fluorescent moiety.

Preferred compounds falling within the scope of Formula I include compounds wherein x is the same as z, and the first amino acid attached to y is an Asp. Most preferably, x is the same as z and is a N-blocked tetrapeptide substrate of a caspase including WEHD SEQ ID NO:1, YVAD SEQ ID NO:2, LEHD SEQ ID NO:3, DETD SEQ ID NO:4, DEVD SEQ ID NO:5, DEHD SEQ ID NO6:, VEHD SEQ ID NO:7, LETD SEQ ID NO:8, LEHD SEQ ID NO:3, SHVD SEQ ID NO:10, DELD SEQ ID NO:11, DGPD SEQ ID NO:12, DEPD SEQ ID NO:13, DGTD SEQ ID NO:14, DLND SEQ ID NO:15, DEED SEQ ID NO:16, DSLD SEQ ID NO:17, DVPD SEQ ID NO:18, DEAD SEQ ID NO:19, DSYD SEQ ID NO:20, ELPD SEQ ID NO:21, VEID SEQ ID NO:26, IETD SEQ ID NO:24 or a N-blocked tetrapeptide substrate of granzyme B including IEPD SEQ ID NO: 23 and VEPD SEQ ID NO:27; or x is the same as z and is a N-blocked peptide which corresponds to a carboxyterminal or aminoterminal fragment consisting of 1, 2 or 3 amino acids of the tetrapeptide substrate of a caspase including WEHD SEQ ID NO:1, YVAD SEQ ID NO:2, LEHD SEQ ID NO:3, DETD SEQ ID NO:4, DEVD SEQ ID NO:5, DEHD SEQ ID NO:6, VEHD SEQ ID NO:7, LETD SEQ ID NO:8, LEHD SEQ ID NO:3, SHVD SEQ ID NO:10, DELD SEQ ID NO:11, DGPD SEQ ID NO:12, DEPD SEQ ID NO:13, DGTD SEQ ID NO:14, DLND SEQ ID NO:15, DEED SEQ ID NO:16, DSLD SEQ ID NO:17, DVPD SEQ ID NO:18, DEAD SEQ ID NO:19, DSYD SEQ ID NO:20, ELPD SEQ ID NO:21, VEID SEQ ID NO:26, IETD SEQ ID NO:24 and granzyme B including IEPD SEQ ID NO:23 and VEPD SEQ ID NO:27.

Preferred compounds falling within the scope of Formula I include compounds wherein y is Rhodamine 110.

In particular, preferred embodiments of the compounds of Formula I are represented by Formula II:

$R_1$-(AA)$_n$-Asp-y-Asp-(AA)$_n$-$R_1$  II or biologically acceptable salts or pro-reporter molecules (such as methyl ester form of carboxyl-containing amino acid residues) thereof, wherein $R_1$ is an N-terminal protecting group including t-butyloxycarbonyl, acetyl, benzyloxycarbonyl; each AA independently is a residue of any natural or non-natural α-amino acid or β-amino acid, or derivatives of an α-amino acid or β-amino acid; each n independently is 0–5; and y is a fluorogenic or fluorescent moiety. An example of a pro-reporter molecule is the methyl ester form of carboxyl-containing amino acid residues comprising compounds of Formula II. Another example of a pro-reporter molecule is the acetoxymethyl (AM) ester form of carboxyl-containing amino acid residues of compounds of Formula II. AM esters of carboxyl-containing compounds are known to be cell permeable and can be hydrolyzed by esterases inside the cells. Once hydrolyzed, the carboxyl-containing compounds become cell impermeable and are trapped inside the cells (Adams et. al., *J Am. Chem. Soc.* 111: 7957–7968 (1989)). AM esters can be prepared by reacting the corresponding carboxy-containing compounds with bromomethyl acetate.

Especially preferred embodiments of the compounds of Formula I are represented by Formula III:

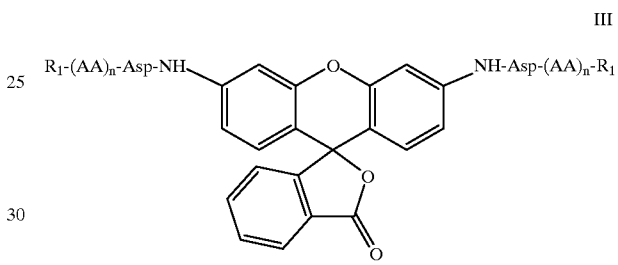

III or biologically acceptable salts or pro-reporter molecules (such as methyl ester form of carboxyl-containing amino acid residues) thereof, wherein $R_1$, AA, n are as defined previously in Formula II. Preferred $R_1$ is t-butyloxycarbonyl, acetyl and benzyloxycarbonyl. Also preferred values for n are 1–3.

Another group of preferred compounds falling within the scope of Formula I include compounds wherein x is not the same as z. Preferred compounds of this group include those wherein x is a peptide or other structure which makes the compound a substrate for caspases, or other proteases or peptidases or other enzymes; and the x-y bond in Formula I is the scissile bond under biological conditions; z is a blocking group and the y-z bond in Formula I is not a scissile bond under biological conditions. Most preferably, x is a N-blocked tetrapeptide substrate of a caspase including WEHD SEQ ID NO: 1, YVAD SEQ ID NO:2, LEHD SEQ ID NO:3, DETD SEQ ID NO:4, DEVD SEQ ID NO:5, DEHD SEQ ID NO:6, VEHD SEQ ID NO:7, LETD SEQ ID NO:8, LEHD SEQ ID NO:3, SHVD SEQ ID NO:10, DELD SEQ ID NO:11, DGPD SEQ ID NO:12, DEPD SEQ ID NO:13, DGTD SEQ ID NO:14, DLND SEQ ID NO:15, DEED SEQ ID NO:16, DSLD SEQ ID NO:17, DVPD SEQ ID NO:18, DEAD SEQ ID NO:19, DSYD SEQ ID NO:20, ELPD SEQ ID NO:21, VEID SEQ ID NO:26, IETD SEQ ID NO:24 or a N-blocked tetrapeptide substrate of granzyme B including IEPD SEQ ID NO:23 and VEPD SEQ ID NO:27; or x is a N-blocked peptide which corresponds to a carboxyterminal or aminoterminal fragment consisting of 1, 2 or 3 amino acids of the tetrapeptide substrates of a caspase including WEHD SEQ ID NO:1, YVAD SEQ ID NO:2, LEHD SEQ ID NO:3, DETD SEQ ID NO:4, DEVD SEQ ID NO:5, DEHD SEQ ID NO:6, VEHD SEQ ID NO:7, LETD SEQ ID NO:8, LEHD SEQ ID NO:3, SHVD SEQ ID NO:10, DELD SEQ ID NO:11, DGPD SEQ ID NO:12, DEPD SEQ ID NO:13, DGTD SEQ ID NO:14, DLND SEQ ID NO:15, DEED SEQ ID NO:16, DSLD SEQ ID NO:17, DVPD SEQ ID NO:18, DEAD SEQ ID NO:19, DSYD SEQ ID NO:20, ELPD SEQ ID NO:21, VEID SEQ ID NO:26, IETD SEQ ID NO:24 or granzyme B including IEPD SEQ ID NO:23 and VEPD SEQ ID NO:27; or x is a N-blocked peptide which corresponds to a carboxyterminal or aminoterminal fragment consisting of 1, 2, 3 or 4 amino acids of the tetrapeptide substrate of a caspase including WEHD SEQ ID NO:1, YVAD SEQ ID NO:2, LEHD SEQ ID NO:3, DETD SEQ ID NO:4, DEVD SEQ ID NO:5, DEHD SEQ ID NO:6, VEHD SEQ ID NO:7, LETD SEQ ID NO:8, LEHD SEQ ID NO:3, SHVD SEQ ID NO:10, DELD SEQ ID NO:11, DGPD SEQ ID NO:12, DEPD SEQ ID NO:13, DGTD SEQ ID NO:14, DLND SEQ ID NO:15, DEED SEQ ID NO:16, DSLD SEQ ID NO:17, DVPD SEQ ID NO:18, DEAD SEQ ID NO:19, DSYD SEQ ID NO:20, ELPD SEQ ID NO:21, VEID SEQ ID NO:26, IETD SEQ ID NO:24 and granzyme B including IEPD SEQ ID NO:23 and VEPD SEQ ID NO:27, plus 1–2 amino acids corresponds to the $P_1'-P_2'$ portion of the substrate of a caspase including G, A, GA, GG and AG.

Specifically, the novel fluorogenic or fluorescent reporter compounds of this invention are of Formula V:

$$R_1\text{-}(AA)_n\text{-Asp-y-}R_6 \qquad\qquad V$$

or biologically acceptable salts or pro-reporter molecules (such as methyl ester form of carboxyl-containing amino acid residues) thereof, wherein:

$R_1$ is an N-terminal protecting group including t-butyloxycarbonyl, acetyl, octanoyl and benzyloxycarbonyl;

each AA independently is a residue of any natural or non-natural α-amino acid or β-amino acid, or a derivative of an α-amino acid or β-amino acid;

n is 0–5;

y is a fluorogenic or fluorescent moiety; and $R_6$ is a blocking group which is not an amino acid or a derivative of an amino acid.

In particular, the novel fluorogenic or fluorescent reporter molecules of this invention of Formula VII–IX are derivatives of Rhodamines including Rhodamine 110, Rhodamine 116 and Rhodamine 19. These novel fluorogenic or fluorescent reporter molecules are prepared by first introducing a blocking group $R_6$ into one of the two amino groups of a Rhodamine to give novel fluorescent dyes of the Formula VI. The remaining $HNR_2$ group is used for reaction with a potential enzyme substrate to give a fluorogenic substrate of Formula VII–IX. By blocking one of the two amino groups in a Rhodamine, the overall size of the substrate is reduced compared to a bis-substituted Rhodamine, such as a bis-peptide-Rhodamine. More importantly, the blocking group is selected such that a) it is stable and will not hydrolyze under biological conditions, thus amino acids are excluded because the peptide bond formed can potentially be cleaved by peptidases which are present in the cells; b) it is preferably not too bulky (e.g. is small) in order to reduce the overall size of the peptide-reporter molecule so that it will be a better enzyme substrate; c) it is preferrably hydrophobic in nature so as to increase the cellular permeability of the fluorogenic or fluorescent reporter molecule.

Preferred $R_6$ blocking groups include, but are not limited to, an $C_{2-12}$ alkyloxycarbonyl group such as methoxycarbonyl, ethoxycarbonyl, hexyloxycarbonyl, octyloxycarbonyl, decyloxycarbonyl and dodecyloxycarbonyl; a $C_{2-12}$ (alkylthio)carbonyl group such as (ethylthio)carbonyl, (hexylthio)carbonyl, (octylthio)carbonyl; an arylalkyloxycarbonyl group such as benzyloxycarbonyl, a $C_{2-12}$ acyl (alkanoyl) group such as acetyl and octanoyl, a carbamyl group such as dimethylcarbamyl, N-methyl-N-hexylcarbamyl, and an alkyl, haloalkyl or aralkyl sulfonyl group such as methanesulfonyl.

Particularly preferred $R_6$ blocking groups are $CH_3OCO$—, $CH_3(CH_2)_pOCO$—(p=1–11), Cbz, $Cl_3CCH_2OCO$— and $PhCH_2CH_2OCO$— (carbamate series); $Me(OCH_2CH_2)_qOCO$— (q=1–4), and $CH_3(CH_2)_r(OCH_2CH_2)_sOCO$— (r=0–5, s=1–4), (alkyloxyalkylcarbamate series); EtSCO—, $CH_3(CH_2)_5SCO$—, $CH_3(CH_2)_7SCO$—, $CH_3(CH_2)_9SCO$— and $CH_3(CH_2)_tSCO$— (t=0–11) (thiocarbamate series); Ts-, $PhSO_2$—, $MeSO_2$—, $CH_3(CH_2)_uSO_2$—(u=0–11), $PhCH_2SO_2$— and $CF_3SO_2$— (sulfonamide series); $Me_2NCO$—, $Et_2NCO$—, and N-Me-N-$CH_3(CH_2)_vNCO$ (v=0–9) (urea series); and HCO—, $CH_3CO$—, $CH_3(CH_2)_wCO$ (w=0–9), $PhCH_2CO$— and $PhCO$— (amide series). Most preferred $R_6$ blocking groups are the ones that contain a hydrophobic group similar to membrane lipid, thus increasing the cellular permeability of the fluorogenic or fluorescent reporter molecules, as well as retention of the fluorescent moiety in the cells after the cleavage of substrate by targeted protease or peptidase. These preferred $R_6$ blocking groups including, but are not limited to $CH_3(CH_2)_p$ $OCO$— (p=1–11) (carbamate series); $Me(OCH_2CH_2)_q$ $OCO$— (q=1–4), and $CH_3(CH_2)_r(OCH_2CH_2)_sOCO$— (r=0–5, s=1–4), (alkyloxyalkylcarbamate series); EtSCO—, $CH_3(CH_2)_5SCO$—, $CH_3(CH_2)_7SCO$—, and $CH_3(CH_2)_9$ SCO— (thiocarbamate series); $CH_3(CH_2)_tSO_2$— (t=0–11), (sulfonamide series); N-Me-N-$CH_3(CH_2)_uNCO$ (u=0–9) (urea series); and $CH_3(CH_2)_wCO$ (w=0–9) (amide series).

The novel fluorogenic or fluorescent reporter molecules of Formula VII–IX are prepared by reacting the amino group $NHR_2$ of the novel fluorescent dyes of Formula VI with a potential enzyme substrate, such as the carboxylic group of a N-blocked peptide, to form an peptide amide bond. The reaction converts the fluorescent molecule of Formula VI into a non-fluorescent peptide-repoter molecule of Formulae VII–IX which is a substrate for a protease or peptidase. It is therefore very important that the blocking group $R_6$—N bond of Formula VII should not be cleaved and that the peptide-reporter amide bond should be the scissile bond under biological conditions. Cleavage of the scissile peptide-reporter amide bond of Formulae VII–IX by proteases or peptidases produces a compound of Formula VI or VI' which is fluorescent.

Specifically preferred embodiments of the compounds of Formula V are represented by Formula VII:

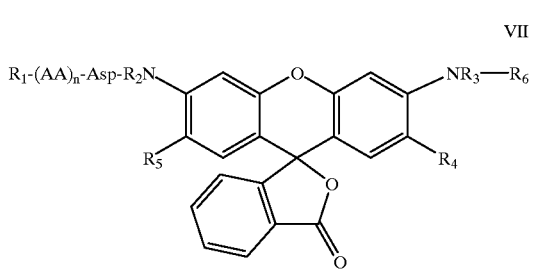

VII or biologically acceptable salts or pro-reporter molecules (such as methyl ester form of carboxyl-containing amino acid residues) thereof, wherein:

$R_2$ and $R_3$ are the same or different and are independently hydrogen, alkyl or aryl;

$R_6$ is a blocking group which is not an amino acid or a derivative of an amino acid;

$R_4$ and $R_5$ are the same or different and are independently hydrogen or alkyl.

$R_1$ is an N-terminal protecting group;

each AA independently is a residue of any natural or non-natural α-amino acid or β-amino acid, or a derivative of an α-amino acid or β-amino acid;

n is 0–5; and the scissile bond is the Asp-N bond in Formula VII.

Preferred $R_2$ and $R_3$ are hydrogen, methyl or ethyl;

Preferred $R_4$ and $R_5$ are hydrogen or methyl.

Preferred amino acids include the natural amino acids including tyrosine, glycine, phenylalanine, methionine, alanine, serine, isoleucine, leucine, threonine, valine, proline, lysine, histidine, glutamine, glutamic acid, tryptophan, arginine, aspartic acid, asparagine, and cysteine. Non-natural amino acids include t-butylglycine and N,N-dimethylglutamine.

An example of a pro-reporter molecule is the methyl ester form of carboxyl-containing amino acid residues comprising compounds of Formula VII. Another example of a pro-reporter molecule is the acetoxymethyl (AM) ester form of carboxyl-containing amino acid residues of compounds of Formula VII.

Another group of preferred embodiments of the compounds of Formula I are represented by Formula VIII:

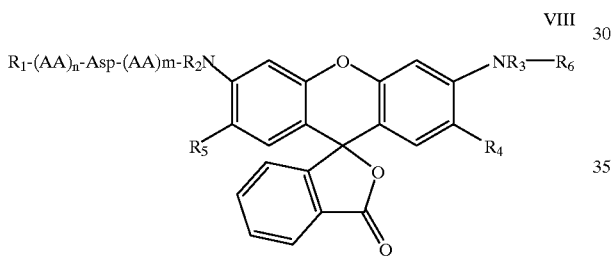

VIII or biologically acceptable salts or pro-reporter molecules (such as methyl ester form of carboxyl-containing amino acid residues) thereof, wherein $R_1$, $R_6$, AA and n are as defined previously in Formulae II and V;

m is an integer from 0–3.

$R_2$ and $R_3$ are the same or different and are independently hydrogen, alkyl or aryl; and $R_4$ and $R_5$ are the same or different and are independently hydrogen or alkyl.

Compounds of Formula VIII are novel fluorogenic or fluorescent substrates for caspases or other enzymes related with apoptosis. When m is 0, cleavage of the amide bond between Asp and Rhodamine will convert the fluorogenic substrate into the fluorescent dye of Formula VI. When m is not 0, cleavage of the amide bond between Asp and $(AA)_m$ will leave the Rhodamine attached to $NH_2-(AA)_m$. The remaining amino acids $(AA)_m$ will then be removed by aminopeptidases present in the cells to give the fluorescent dye of Formula VI. $(AA)_m$ may be designed to correspond with the P' sequence of the cleavage site of substrates of caspases or apoptosis related enzymes. The incorporation of the P' sequence of known substrates of caspases or apoptosis related enzymes are expected to increase specificity and affinity of the fluorogenic substrates. Since aminopeptidases are widely present in cells, one can insert a $(AA)_m$ sequence in the design of substrates of Formula VIII for whole cell assays. This is another advantage of whole cell assays over cell-free enzyme assays. For instance, when $(AA)_m$ is Gly, a substrate of Formula VIII will work in whole cell assays but otherwise will not work in cell-free caspase assay because cleavage of Asp-Gly amide bond will leave the Gly attached to the Rhodamine, which is not fluorescent.

An example of a pro-reporter molecule is the methyl or ethyl ester forms of carboxyl-containing amino acid residues comprising compounds of Formula VIII. Another example of a pro-reporter molecule is the acetoxymethyl (AM) or pivaloyloxymethyl (PM) ester form of carboxyl-containing amino acid residues of compounds of Formula VIII. AM esters of carboxyl-containing compounds are known to be cell permeable and can be hydrolyzed by esterases inside the cells. Once hydrolyzed, the carboxyl-containing compounds become cell impermeable and are trapped inside the cells (Adams et al., *J Am. Chem. Soc.* 111:7957–7968 (1989)). AM esters can be prepared by reacting the corresponding carboxy-containing compounds with bromomethyl acetate.

Yet another group of preferred embodiments of the compounds of Formula I are represented by Formula IX:

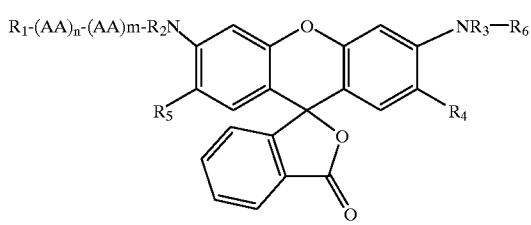

IX or biologically acceptable salts or pro-reporter molecules (such as methyl ester form of carboxyl-containing amino acid residues) thereof, wherein $R_1$, $R_6$, AA and n are as defined previously in Formulae II and V;

m is an integer from 0–3.

$R_2$ and $R_3$ are the same or different and are independently hydrogen, alkyl or aryl; and $R_4$ and $R_5$ are the same or different and are independently hydrogen or alkyl.

Preferred $R_1$ is t-butyloxycarbonyl, acetyl, octanoyl, dodecanoyl and benzyloxycarbonyl. Preferred n is 1–4. Preferred $R_2$ and $R_3$ are hydrogen, methyl or ethyl. Preferred $R_4$ and $R_5$ are hydrogen or methyl. Preferred $R_6$ blocking groups include, but are not limited to, an $C_{2-12}$ alkyloxycarbonyl group such as methoxycarbonyl, ethoxycarbonyl, hexyloxycarbonyl, octyloxycarbonyl, decyloxycarbonyl and dodecyloxycarbonyl; a $C_{2-12}$ (alkylthio)carbonyl group such as (ethylthio)carbonyl, (hexylthio)carbonyl, (octylthio)carbonyl; an arylalkyloxycarbonyl group such as benzyloxycarbonyl; a $C_{2-12}$ acyl (alkanoyl) group such as acetyl and octanoyl; a carbamyl group such as dimethylcarbamyl, N-methyl-N-hexylcarbamyl; and an alkyl, haloalkyl or aralkyl sulfonyl group such as methanesulfonyl.

In Formula IX, $(AA)_n$ is designed to be an amino acid or a peptide which is recognized by a specific peptidase or protease as the sequence in the p side and will be cleaved by the targeted peptidase or protease. $(AA)_m$ is designed to be an amino acid or peptide which is recognized by a specific peptidase or protease as the sequence in the P' side, and which can be removed by aminopeptidases presented in the cells. When $R_1$ is a N-terminal protecting group such as a t-butyloxycarbonyl, Cbz or acetyl, compounds of Formula IX are substrates for endopeptidases such as cathepsin D or protease such as HIV protease; when $R_1$ is H, compounds of Formula IX are substrates for exopeptidases such as methionine aminopeptidase.

Specifically, compounds of Formula IX are designed to be substrates of type 2 methionine aminopeptidase (MetAP-2). MetAP-2 was identified recently by two research groups (Griffith, E. C., et al., *Chem. Biol* 4:461–471 (1997) and Sin, N., et al., *Proc. Natl. Acad. Sci. USA* 94:6099–6103 (1997)) to be the commom target of angiogenesis inhibitor AGM-1470, an anti-cancer drug currently undergoing clinical trials. MetAP-2 is a bifunctional enzyme which also regulate protein synthesis by affecting the phosphorylaton state of eIF-2. AGM-1470 is reported to only inhibit the aminopeptidase activity of MetAP-2 and have no effect on the regulatory activity of MetAP-2 (Griffith, E. C., et al., *Chem. Biol.* 4:461–471 (1997)). Since angiogenesis inhibitor such as AGM-1470 is known to be able to selectively kill cancer cells, inhibitors of MetAP-2 are expected to have anti-angiogenic properties and to be potential novel anticancer agents.

MetAP-2 is a cobalt-dependent enzyme that hydrolyzes the amino-terminal methionine from certain proteins. Its preferred substrates are Met-X-Y. X is an amino acid with small and uncharged side groups, such as Gly, Ala, Ser, whereas Leu, Met, Arg and Tyr are known to result in inactive substrates. Y can be Ser, Met, Gly or other amino acids (Li, X. & Chang Y.-H., *Biochem. Biophy. Res. Com.* 227:152–159 (1996)). Since Rhodamine is much larger than an amino acid, a compound with methionine directly attached to Rhodamine most probably will not be a substrate for MetAP-2. Taking advantage of the presence of aminopeptidase in whole cells, the insertion of a $(AA)_m$ sequence between methionine and Rhodamine will make a good substrate for MetAP-2. This type of substrate is expected to work well in a whole cell assay but otherwise will not work in a cell-free MetAP-2 enzyme assay.

For compounds of Formula IX designed to be substrates of MetAP-2, preferred $R_1$ is H, preferred $(AA)_n$ is Met, and preferred $(AA)_m$ is Gly, Ala, Gly-Gly, Ala-Gly or Gly-Ala. The methionine will be cleaved by type 2 methionine aminopeptidase in endothelial cells to give the Rhodamine attached to $(AA)_m$. Aminopeptidases present inside the cells will then remove the $(AA)_m$ to give the fluorescent dye of Formula VI. Compounds of Formula IX will be used for the screening of inhibitors of MetAP-2 in endothelial cells, which is expected to lead to the identification of novel anti-cancer drugs.

Compounds of Formula IX also can be designed to be substrates of HIV protease. HIV protease is an aspartic protease which processes polypeptides transcribed from the gag and pol genes and is essential for the maturation of infectious virus. Therefore HIV protease has been one of the major targets for chemotherapeutic intervention of HIV. Recently, several HIV protease inhibitors have shown great potential in the treatment of HIV and have been approved for marketing. Most of these HIV protease inhibitors were designed based on the structure of the substrates of the protease. Therefore these compounds are either peptides or peptidomimetics. The search for new and novel HIV protease inhibitors is expected to provide more efficacious drugs for the fight against this deadly disease.

The preferred substrates of HIV protease are peptides with a scissile hydrophobic-hydrophobic or aromatic-proline peptide bond between the $P_1$–$P_1'$ (West, M. L., and Fairlie, D. P., *Trand. Pharm. Sci.* 16:67–74 (1995)). Nine distinct sites in the viral gag and gag-pol proteins have been found to be cleaved by the protease (Martin, J. A., et al., *Prog. Med. Chem.* 32:239–287 (1995)). The $P_4$–$P_3'$ sequences of these nine sites are Ser-Gln-Asn-Tyr-Pro-Ile-Val SEQ ID NO:28, Ala-Arg-Val-Leu-Ala-Glu-Ala SEQ ID NO:29, Ala-Thr-Ile-Met-Met-Gln-Arg SEQ ID NO:30, Arg-Gln-Ala-Asn-Phe-Leu-Gly SEQ ID NO:31, Pro-Gly-Asn-Phe-Leu-Gln-Ser SEQ ID NO:32, Ser-Phe-Ser-Phe-Pro-Gln-Ile SEQ ID NO:33, Thr-Leu-Asn-Phe-Pro-Ile-Ser SEQ ID NO:34, Ala-Glu-Thr-Phe-Tyr-Val-Asp SEQ ID NO:35 and Arg-Lys-Val-Leu-Phe-Leu-Asp SEQ ID NO:36. Many fluorogenic, radioactive, or chromogenic substrates of HIV protease have been prepared based on these natural substrates for HIV protease activity assays. An intramolecularly quenched fluorogenic substrate, 2-aminobenzoyl-Thr-Ile-Nle-(4-$NO_2$-Phe)-Gln-Arg-$NH_2$ SEQ ID NO:141, wherein the scissile bond is the Nle-(4-$NO_2$-Phe), was prepared based on the p24/p15 cleavage site-derived hexapeptide substrate (Toth, M. V., and Marshall, G. R., *Int. J. Pept. Protein Res.* 36:544–550 (1990)). A fluorometric assay for HIV-protease activity using HPLC with the substrate N-Dns-Ser-Gln-Asn-Tyr-Pro-Ile-Val SEQ ID NO:28 was reported by Tamburini et al. (Tamburini, P. P., et al., *Anal. Biochem.* 186:363–368 (1990)), wherein the Tyr-Pro is the scissile bond. Many other HIV protease substrates incorporating sequences from both the P side and P' side of the cleavage sites of HIV protease substrates have been developed, and these include the fluorogenic N-alpha-benzoyl-Arg-Gly-Phe-Pro-MeO-beta-naphthylamide SEQ ID NO:37, which contains the Phe-Pro dipeptide bond recognized by HIV-1 protease (Tyagi, S. C., and Carter, C. A., *Anal Biochem.* 200:143–148 (1992)); the radiolabeled heptapeptide substrate, [tyrosyl-3,5-$^3$H]Ac-Ser-Gln-Asn-Tyr-Pro-Val-Val-$NH_2$ SEQ ID NO:38, which is based on the p17-p24 cleavage site Tyr-Pro found in the viral polyprotein substrate Pr55gag (Hyland, L. J., et al., *Anal. Biochem.* 188:408–415 (1990)); the angiotensin I-based peptide Asp-Arg-Val-Tyr-Ile-His-Pro-Phe-His-Leu-Leu-Glu-Glu-Ser SEQ ID NO:39, which yields angiotensin I (Ang I) and Leu-Glu-Glu-Ser SEQ ID NO:40 (Evans, D. B., et al., *Anal. Biochem.* 206:288–292 (1992)); the intramolecular fluorescence resonance energy transfer (FRET) substrate 4-(4-dimethylaminophenylazo)benzoic acid (DABCYL)-Ser-Gln-Asn-Tyr-Pro-Ile-Val-Gln-5-[(2-aminoethyl)amino]naphthalene-1 SEQ ID NO:41 sulfonic acid (EDANS), wherein Tyr-Pro is the cleavage site (Matayoshi, E. D., et al., *Science* 247:954–958 (1990)); and the chromophoric peptide substrates H-Ser-Gln-Asn-Leu-Phe($NO_2$)-Leu-Asp-Gly-$NH_2$ SEQ ID NO:42 and acetyl-Arg-Lys-Ile-Leu-Phe($NO_2$)-Leu-Asp-Gly-$NH_2$ SEQ ID NO:43, wherein the amide bond between the p-nitrophenylalanyl and leucyl residues is the scissile bond. In addition, the chromogenic substrate, Lys-Ala-Arg-Val-Leu-Phe($NO_2$)-Glu-Ala-Met SEQ ID NO:44, wherein the Leu-Phe($NO_2$) is the cleavage site, was reported (Richards, A. D., et al., *J Biol. Chem.* 265:7733–7736 (1990)). SAR studies found that substitution of the Leu residue in $P_1$ with norleucine, Met, Phe, or Tyr had minimal effects on the kinetic parameters ($K_{cat}$ and $K_{cat}/K_m$), as determined at different pH values, whereas peptides containing Ile or Val in $P_1$ were found to hydrolyze extremely slowly. Taking advantage of the presence of non-specific aminopeptidases in whole cells, fluorogenic or fluorescent substrates of HIV protease of Formula IX can be designed to incorporate amino acids from both the P side and P' side of HIV substrate for application in whole cell assays. It is expected that after the peptide sequence in the P side was cleaved by the HIV protease, the peptide sequence in the P' side will be removed by aminopeptidases presented in the cells.

For compounds of Formula IX designed to be substrates of HIV protease, preferred $R_1$ is acetyl or Cbz, preferred $(AA)_n$ is Thr-Ile-Nle, and preferred $(AA)_m$ is Phe-Gln-Arg, Phe-Gln, or Phe; or preferred $(AA)_n$ is Ser-Leu-Asn-Phe SEQ ID NO:54, or Leu-Asn-Phe, and preferred $(AA)_m$ is Pro-Ile-Val, Pro-Ile, or Pro; or preferred $(AA)_n$ is Ser-Gln-Asn-Tyr SEQ ID NO:45, or Gln-Asn-Tyr, and preferred $(AA)_m$ is Pro-Ile-Val-Gln SEQ ID NO:46, Pro-Ile-Val, Pro-Val-Val-$NH_2$, Pro-Val-$NH_2$, Pro-Ile, or Pro; or preferred $(AA)_n$ is Arg-Gly-Phe, and preferred $(AA)_m$ is Pro; or preferred $(AA)_n$ is Lys-Ala-Arg-Val-Leu SEQ ID NO:47, Ala-Arg-Val-Leu SEQ ID NO:48, or Arg-Val-Leu, and preferred $(AA)_m$ is Phe-Glu-Ala-Met SEQ ID NO:49, Phe-Glu-Ala, Phe-Glu, or Phe; or preferred $(AA)_n$ is Pro-Phe-His-Leu SEQ ID NO:50, or Phe-His-Leu, and preferred $(AA)_m$ is Leu-Glu-Glu-Ser SEQ ID NO:40, Leu-Glu-Glu, Leu-Glu, or Leu; or preferred $(AA)_n$ is Ser-Gln-Asn-Leu-Phe SEQ ID NO:140, Gln-Asn-Leu-Phe SEQ ID NO:51, Asn-Leu-Phe, Arg-Lys-Ile-Leu-Phe SEQ ID NO:52, Lys-Ile-Leu-Phe SEQ ID NO:53, or Ile-Leu-Phe, and preferred $(AA)_m$ is Leu-Asp-Gly-$NH_2$, Leu-Asp-$NH_2$, or Leu-$NH_2$. More preferred $(AA)_n$ is Ser-Leu-Asn-Phe SEQ ID NO:54, or Leu-Asn-Phe, and more preferred $(AA)_m$ is Pro-Ile-Val, Pro-Ile, or Pro; or more preferred $(AA)_n$ is Arg-Gly-Phe, and more preferred $(AA)_m$ is Pro.

Substrates of HIV protease of Formula IX are expected to work in whole cell assays but otherwise will not work in cell-free enzyme assays. Cleavage of the $(AA)_n$-$(AA)_m$ amide bond by HIV protease in HIV infected cells will give the Rhodamine attached to $(AA)_m$. Aminopeptidases present inside the cells will then remove the $(AA)_m$ to give the fluorescent dye of Formula VI. Compounds of Formula IX will be used for the screening of inhibitors of HIV protease in HIV infected cells. This should speed up the process for the discovery of novel HIV protease inhibitors, especially the discovery of non-peptide or non-peptidomimetic HIV protease inhibitors, which might lead to better anti-HIV agents than currently available drugs. Since HIV protease processes viral precursor proteins at a late stage in viral replication, a cell permeable fluorogenic or fluorescent substrate for an HIV protease also can be used to screen compounds which inhibit gene transcription or translation, viral entry, or other key proteins in the early stage of HIV infection. Therefore this method can lead to the identification of inhibitors of HIV infections with a novel mechanism, which could not be identified in a cell-free enzyme assay. In addition, since HIV protease in HIV infected cells will cleave the cell permeable substrates of Formula IX to produce the fluorescent dye of Formula VI inside the cells, substrates of Formula V also can be used for the diagnosis of HIV infection.

Compounds of Formula IX also can be designed to be substrates of adenovirus protease. Adenovirus are the cause of several diseases including sporatic respiratory disease and epidemic acute respiratory disease which can lead to preumonia. Adenovirus protease is a cysteine protease which cleaves several viral proteins and is required for virus maturation and infectivity (Weber, J. M., *Curr. Top. Microbiol. Immunol.* 199/I:227–235 (1995)). The preferred substrates of adenovirus protease includes (M,L,I)XGX-G and (M,L,I)XGG-X. The specificity of the substrates are mainly determined by $P_2$ and $P_4$ amino acids (Diouri, M., et al., *J Biol. Chem.* 271:32511–32514 (1996)). Hydrophobic amino acids such as Met, Leu and Ile are preferred in $P_4$. Small amino acid such as Gly is preferred in $P_2$. A small and hydrophobic amino acid is also preferred for $P_1$ and $P_1'$, such as Ala and Gly; while $P_3$ can accommodate almost any amino acid. These observations were supported by the recently determined crystal structure of human adenorivus proteinase with its 11 aminoacid cofactor and substrate modeling based on the crystal structure (Ding, J., et al., *EMBO J.* 15:1778–1783 (1996)). Taking advantage of the presence of aminopeptidase in whole cells, fluorogenic or fluorescent substrates of adenovirus protease can be designed to incorporate amino acids either from the P side only, or from both the P side and P' side of adenovirus protease substrate for application in whole cell assays.

For compounds of Formula IX designed to be substrates of adenovirus protease, preferred $R_1$ is acetyl or Cbz, preferred $(AA)_n$ is Leu-Arg-Gly-Gly SEQ ID NO:55, Met-Arg-Gly-Gly SEQ ID NO:56, Ile-Arg-Gly-Gly SEQ ID NO:57, Leu-Val-Gly-Gly SEQ ID NO:58, Met-Val-Gly-Gly SEQ ID NO:59 or Ile-Val-Gly-Gly SEQ ID NO:60, and preferred $(AA)_m$ is Gly, Ala, or m=0. When m is 0, cleavage of $(AA)_n$ Rhodamine amide bond by the adenovirus protease will produce a fluorescent dye of Formula VI. When m is not 0, cleavage of the $(AA)_n$-$(AA)_m$ amide bond by adenovirus protease in the cells will give the Rhodamine attached to $(AA)_m$. Aminopeptidases present inside the cells will then remove the $(AA)_m$ to give the fluorescent dye of Formula VI. Compounds of Formula IX will be used for the screening of inhibitors of adenovirus protease in adenovirus infected cells.

Compounds of Formula IX also can be designed to be substrates of herpes simplex virus type 1 (HSV-1) protease. Human herpes simplex virus type 1 is responsible for herpes labialis (cold sores). The HSV-1 protease is a serine protease and is responsible for proteolytic processing of itself and ICP35 for assembly of viral capside (Gao, M., et al., *J Virol.* 68:3702–3712 (1994)). Two proteolytic sites have been identified to be Ala247 and Ser248 and Ala610 and Ser611 within the protease (Dilanni, C. L., et al., *J Biol. Chem.* 268:25449–25454 (1993)). Recently, an eight amino acid consensus peptide of LVLASSSF SEQ ID NO:61 was found to be cleaved as efficiently as a 20-mer maturation site peptide, and the $P_4$ to $P_1$ sequence was defined as the minimal substrate recognition domain for the HSV-1 protease (O'Boyle, D. R., et al., *Virology* 236:338–347 (1997)). It also have been reported that the specificity of HSV-1 protease resides within the $P_4$-$P_1'$ region of the cleavage sites (McCann, P. J., et al., *J Virol.* 68:526–529 (1994)). Taking advantage of the presence of aminopeptidase in whole cells, fluorogenic or fluorescent substrates of HSV-1 protease are designed to incorporate amino acids either from the $P_4$–$P_1$ only, or both from P4–P, and P' side of HSV-1 protease substrate for application in whole cell assays.

For compounds of Formula IX designed to be substrates of HSV-1 protease, preferred $R_1$ is acetyl or Cbz, preferred $(AA)_n$ is Leu-Val-Leu-Ala SEQ ID NO:62, and preferred $(AA)_m$ is Ser, Ser-Ser, or m=0. When m is 0, cleavage of $(AA)_n$- Rhodamine amide bond by the HSV-1 protease will produce fluorescent dye of the Formula VI. When m is not 0, cleavage of the $(AA)_n$-$(AA)_m$ amide bond by HSV-1 in the cells will give the Rhodamine attached to $(AA)_m$. Aminopeptidases present inside the cells will then remove the $(AA)_m$ to give the fluorescent dye of Formula VI. Compounds of Formula IX will be used for the screening of inhibitors of HSV-1 protease in HSV-1 infected cells.

Compounds of Formula IX also can be designed to be substrates of human cytomegalovirus (HCMV) protease. HCMV can cause life-threatening infections in congenitally infected infants, immunocompromised individuals and immunosuppressed cancer or transplant patients. Human cytomegalovirus (HCMV) encodes a protease that cleaves itself and the HCMV assembly protein and is essential for virus replication, therefore it is a potential target for therapeutic intervention. The HCMV protease is a serine protease and two proteolytic processing sites within the protease were identified at Ala 256-Ser 257 (release site) and Ala 643-Ser 644 (maturation site). (Sztevens, J. T., et al, *Eur. J. Biochem.* 226:361–367(1994)). A fluorogenic substrate, DABCYL-Arg-Gly-Val-Val-Asn-Ala-Ser-Ser-Arg-Leu-Ala-EDANS SEQ ID NO:63 was synthesized and found to be cleaved efficiently by CMV protease at the Ala-Ser peptide bond (Holskin, B. P., et al., *Anal. Biochem.* 227:148–155 (1995)). Recently, it was reported that replacement of the Val-Val-Asn sequence corresponding to the $P_4$–$P_2$ residues of the maturation site of the enzyme by the optimized Tbg-Tbg-Asn(NMe$_2$) (Tbg, t-butylglycine) sequence increase significant the affinity of the substrate to the protease. An AMC fluorogenic substrate was prepared with the P side peptide sequence including these improved amino acids (Bonneau, P. R., et al., *Anal. Biochem.* 255:59–65 (1998)). Taking advantage of the presence of aminopeptidase in whole cells, fluorogenic or fluorescent substrates of HCMV protease are designed to incorporate amino acids either from the P side only, or both from P side and P' side of HCMV protease substrate for application in whole cell assays.

For compounds of Formula IX designed to be substrates of HCMV protease, preferred $R_1$ is acetyl or Cbz, preferred $(AA)_n$ is Val-Val-Asn-Ala SEQ ID NO:64, Tbg-Tbg-Asn-Ala SEQ ID NO:65, and preferred $(AA)_m$ is Ser, Ser-Ser, or m=0. When m is 0, cleavage of $(AA)_n$-Rhodamine amide bond by the HCMV protease will produce fluorescent dye of the Formula VI. When m is not 0, cleavage of the $(AA)_n$-$(AA)_m$ amide bond by HCMV in the cells will give the Rhodamine attached to $(AA)_m$. Aminopeptidases present inside the cells will then remove the $(AA)_m$ to give the fluorescent dye of Formula VI. Compounds of Formula IX will be used for the screening of inhibitors of HCMV protease in HCMV infected cells.

Compounds of Formula IX also can be designed to be substrates of hepatitis C virus (HCV) protease. HCV is the major causative agent of both parenterally transmitted and sporadic non-A and non-B hepatitis, which infected an estimated 50 million people worldwide. HCV protease NS3 and its protein activator NS4A participate in the processing of the viral polyprotein, thus the NS3/4A protease complex is an attractive target for antiviral therapy against HCV. The HCV protease is a serine protease and Cys-Ser has been identified as a cleavage site. One of the substrate sequence is Asp-Asp-Ile-Val-Pro-Cys-Ser-Met-Ser-Tyr SEQ ID NO:66, and $P_1$ Cys and $P_3$ Val were found to be critical (Zhang, R., et al., *J. Virol.* 71:6208–6213 (1997)). Taking advantage of the presence of aminopeptidase in whole cells, fluorogenic or fluorescent substrates of HCV protease are designed to incorporate amino acids both from the P side and P' side of HCV protease substrate for application in whole cell assays.

For compounds of Formula IX designed to be substrates of HCV protease, preferred $R_1$ is acetyl or Cbz, preferred $(AA)_n$ is Asp-Asp-Ile-Val-Pro-Cys SEQ ID NO:67, Asp-Ile-Val-Pro-Cys SEQ ID NO:68, or Ile-Val-Pro-Cys SEQ ID NO:69 and preferred $(AA)_m$ is Ser-Met-Ser-Tyr SEQ ID NO:70, Ser-Met-Ser, Ser-Met, Ser, or m=0. When m is 0, cleavage of $(AA)_n$-Rhodamine amide bond by the HCV protease will produce fluorescent dye of the Formula VI. When m is not 0, cleavage of the $(AA)_n$-$(AA)_m$ amide bond by HCV in the cells will give the Rhodamine attached to $(AA)_m$. Aminopeptidases present inside the cells will then remove the $(AA)_m$ to give the fluorescent dye of Formula VI.

Compounds of Formula IX will be used for the screening of inhibitors of HCV protease in HCV infected cells.

The invention also relates to novel compounds of Formula VI which are derivatives of a Rhodamine and are obtained by introducing a blocking group $R_6$ onto one of the two amino groups on a Rhodamine. The $R_2HN$ group in Formula VI provides the point of attachment for the reaction with a potential enzyme substrate, such as the carboxylic group of a N-blocked peptide, to form an peptide amide bond. The reaction converts the fluorescent molecule of Formula VI into a non-fluorescent molecule of Formulae VII–IX and produces a peptide-reporter molecule which functions as a substrate for a protease or peptidase. The peptide-reporter amide bond in Formulae VII–IX is the scissile bond under biological conditions. Cleavage of the scissile peptide-reporter amide bond in the peptide-reporter by proteases or peptidases produces a compound of Formula VI or VI' which is fluorescent. More importantly, the blocking group can incorporate a hydrophobic group. The hydrophobic group is designed to increase the membrane permeability of the substrates, and to result in an accumulation of the substrate inside the cells, as well as to increase retention of the fluorescence moiety inside the cells after its cleavage by targeted protease or peptidase.

The novel fluorescent dyes of this invention are of Formula VI:

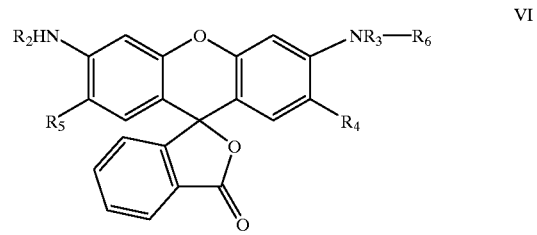

VI or biologically acceptable salts wherein $R_2$–$R_6$ are defined above with respect to Formula VII.

Preferred $R_2$ and $R_3$ are hydrogen, methyl or ethyl;
Preferred $R_4$ and $R_5$ are hydrogen or methyl.

Compounds of Formula VI of the present invention may exist in tautomeric forms, particularly the ring opening form of Formula VI'. The invention includes all tautomeric forms including VI and VI'.

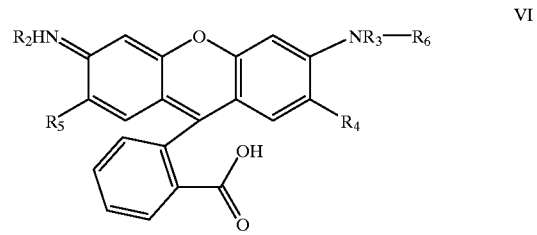

VI

Preferred fluorogenic or fluorescent substrates of the present invention are compounds having Formula II and include, but are not limited to:
(Z-WEHD)$_2$-Rhodamine 110, SEQ ID NO:1
(Z-YVAD)$_2$-Rhodamine 110, SEQ ID NO:2
(Z-DETD)$_2$-Rhodamine 110, SEQ ID NO:4
(Z-DEVD)$_2$-Rhodamine 110, SEQ ID NO:5
(Z-DEHD)$_2$-Rhodamine 110, SEQ ID NO:6
(Z-VEHD)$_2$-Rhodamine 110, SEQ ID NO:7
(Z-LETD)$_2$-Rhodamine 110, SEQ ID NO:8
(Z-LEHD)$_2$-Rhodamine 110, SEQ ID NO:3

(Z-LBVD)₂-Rhodamine 110, SEQ ID NO:9
(Z-IEPD)₂-Rhodamine 110, SEQ ID NO:23
(Z-VEPD)₂-Rhodamine 110, SEQ ID NO:27
(Z-SHVD)₂-Rhodamine 110, SEQ ID NO:10
(Z-DELD)₂-Rhodamine 110, SEQ ID NO:11
(Z-DGPD)₂-Rhodamine 110, SEQ ID NO:12
(Z-DEPD)₂-Rhodamine 110, SEQ ID NO:13
(Z-DGTD)₂-Rhodamine 110, SEQ ID NO:14
(Z-DLND)₂-Rhodamine 110, SEQ ID NO:15
(Z-DEED)₂-Rhodamine 110, SEQ ID NO:16
(Z-DSLD)₂-Rhodamine 110, SEQ ID NO:17
(Z-DVPD)₂-Rhodamine 110, SEQ ID NO:18
(Z-DEAD)₂-Rhodamine 110, SEQ ID NO:19
(Z-DSYD)₂-Rhodamine 110, SEQ ID NO:20
(Z-ELPD)₂-Rhodamine 110, SEQ ID NO:21
(Z-VEID)₂-Rhodamine 110, SEQ ID NO:26
(Z-IETD)₂-Rhodamine 110, SEQ ID NO:24
(Z-VD)₂-Rhodamine 110,
(Z-TD)₂-Rhodamine 110,
(Z-AD)₂-Rhodamine 110,
(Z-VAD)₂-Rhodamine 110,
(Boc-WEHD)₂-Rhodamine 110, SEQ ID NO:1
(Boc-YVAD)₂-Rhodamine 110, SEQ ID NO:2
(Boc-DETD)₂-Rhodamine 110, SEQ ID NO:4
(Boc-DEVD)₂-Rhodamine 110, SEQ ID NO:5
(Boc-DEHD)₂-Rhodamine 110, SEQ ID NO:6
(Boc-VEHD)₂-Rhodamine 110, SEQ ID NO:7
(Ac-YVAD)₂-Rhodamine 110, SEQ ID NO:2
(Ac-LETD)₂-Rhodamine 110, SEQ ID NO:8
(Ac-LEHD)₂-Rhodamine 110, SEQ ID NO:3
(Ac-DEVD)₂-Rhodamine 110, SEQ ID NO:5
(Ac-LEVD)₂-Rhodamine 110, SEQ ID NO:9
(Ac-IEPD)₂-Rhodamine 110, SEQ ID NO:23
(Ac-VEPD)₂-Rhodamine 110, SEQ ID NO:27
(Ac-VD)₂-Rhodamine 110,
(Ac-TD)₂-Rhodamine 110,
(Ac-AD)₂-Rhodamine 110,
(Ac-VAD)₂-Rhodamine 110,
(Z-YVAD)₂-Rhodamine 116, SEQ ID NO:2
(Z-LEHD)₂-Rhodamine 116, SEQ ID NO:3
(Z-DETD)₂-Rhodamine 116, SEQ ID NO:4
(Z-DEVD)₂-Rhodamine 116, SEQ ID NO:5
(Z-YVAD)₂-Rhodamine 19, SEQ ID NO:2
(Z-LEHD)₂-Rhodamine 19, SEQ ID NO:3
(Z-DETD)₂-Rhodamine 19, SEQ ID NO:4
(Z-DEVD)₂-Rhodamine 19, SEQ ID NO:5
(Z-YVAD(OAM))₂-Rhodamine 110, SEQ ID NO:2
(Z-LE(OAM)HD(OAM))₂-Rhodamine 110, SEQ ID NO:3
(Z-D(OAM)E(OAM)TD(OAM))₂-Rhodamine 110, SEQ ID NO:4
(Z-D(OAM)E(OAM)VD(OAM))₂-Rhodamine 110, SEQ ID NO:5
(Z-D(OMe)E(OMe)VD(OAM))₂-Rhodamine 110, and SEQ ID NO:5
(Z-D(OMe)E(OMe)VD)₂-Rhodamine 110. SEQ ID NO:5

Preferred fluorogenic or fluorescent substrates of the present invention are compounds having Formula VII and include, but are not limited to:
N-(Z-WEHD)-N'-acetyl-Rhodamine 110, SEQ ID NO:1
N-(Z-YVAD)-N'-acetyl-Rhodamine 110, SEQ ID NO:2
N-(Z-LEHD)-N'-acetyl-Rhodamine 110, SEQ ID NO:3
N-(Z-LEVD)-N'-acetyl-Rhodamine 110, SEQ ID NO:9
N-(Z-DETD)-N'-acetyl-Rhodamine 110, SEQ ID NO:4
N-(Z-DEVD)-N'-acetyl-Rhodamine 110, SEQ ID NO:5
N-(Z-DEHD)-N'-acetyl-Rhodamine 110, SEQ ID NO:6
N-(Z-VEHD)-N'-acetyl-Rhodamine 110, SEQ ID NO:7
N-(Z-LETD)-N'-acetyl-Rhodamine 110, SEQ ID NO:8
N-(Z-IEPD)-N'-acetyl-Rhodamine 110, SEQ ID NO:23
N-(Z-VEPD)-N'-acetyl-Rhodamine 110, SEQ ID NO:27
N-(Z-SHVD)-N'-acetyl-Rhodamine 110, SEQ ID NO:10
N-(Z-DELD)-N'-acetyl-Rhodamine 110, SEQ ID NO:11
N-(Z-DGPD)-N'-acetyl-Rhodamine 110, SEQ ID NO:12
N-(Z-DEPD)-N'-acetyl-Rhodamine 110, SEQ ID NO:13
N-(Z-DGTD)-N'-acetyl-Rhodamine 110, SEQ ID NO:14
N-(Z-DLND)-N'-acetyl-Rhodamine 110, SEQ ID NO:15
N-(Z-DEED)-N'-acetyl-Rhodamine 110, SEQ ID NO:16
N-(Z-DSLD)-N'-acetyl-Rhodamine 110, SEQ ID NO:17
N-(Z-DVPD)-N'-acetyl-Rhodamine 110, SEQ ID NO:18
N-(Z-DEAD)-N'-acetyl-Rhodamine 110, SEQ ID NO:19
N-(Z-DSYD)-N'-acetyl-Rhodamine 110, SEQ ID NO:20
N-(Z-ELPD)-N'-acetyl-Rhodamine 110, SEQ ID NO:21
N-(Z-VEID)-N'-acetyl-Rhodamine 110, SEQ ID NO:26
N-(Z-IETD)-N'-acetyl-Rhodamine 110, SEQ ID NO:24
N-(Z-VD)-N'-acetyl-Rhodamine 110,
N-(Z-TD)-N'-acetyl-Rhodamine 110,
N-(Z-AD)-N'-acetyl-Rhodamine 110,
N-(Z-VAD)-N'-acetyl-Rhodamine 110,
N-(Boc-WEHD)-N'-acetyl-Rhodamine 110, SEQ ID NO:1
N-(Boc-YVAD)-N'-acetyl-Rhodamine 110, SEQ ID NO:2
N-(Ac-LETD)-N'-acetyl-Rhodamine 110, SEQ ID NO:8
N-(Ac-LEHD)-N'-acetyl-Rhodamine 110, SEQ ID NO:3
N-(Z-DEVD)-N'-methoxycarbonyl-Rhodamine 110, SEQ ID NO:5
N-(Z-YVAD)-N'-methoxycarbonyl-Rhodamine 110, SEQ ID NO:2
N-(Z-LEVD)-N'-methoxycarbonyl-Rhodamine 110, SEQ ID NO:9
N-(Z-LEHD)-N'-methoxycarbonyl-Rhodamine 110, SEQ ID NO:3
N-(Ac-WEHD)-N'-methoxycarbonyl-Rhodamine 110, SEQ ID NO:1
N-(Ac-YVAD)-N'-methoxycarbonyl-Rhodamine 110, SEQ ID NO:2
N-(Ac-DEVD)-N'-methoxycarbonyl-Rhodamine 110, SEQ ID NO:5
N-(Ac-DEVD)-N'-methoxycarbonyl-Rhodamine 110, SEQ ID NO:6
N-(Ac-DETD)-N'-methoxycarbonyl-Rhodamine 110, SEQ ID NO:4
N-(Ac-LEVD)-N'-methoxycarbonyl-Rhodamine 110, SEQ ID NO:9
N-(Ac-LEHD)-N'-methoxycarbonyl-Rhodamine 110, SEQ ID NO:3
N-(Ac-LETD)-N'-methoxycarbonyl-Rhodamine 110, SEQ ID NO:8
N-(Ac-VEHD)-N'-methoxycarbonyl-Rhodamine 110, SEQ ID NO:7
N-(Ac-IEPD)-N'-methoxycarbonyl-Rhodamine 110, SEQ ID NO:23
N-(Z-WEHD)-N'-ethoxycarbonyl-Rhodamine 110, SEQ ID NO:1
N-(Z-YVAD)-N'-ethoxycarbonyl-Rhodamine 110, SEQ ID NO:2
N-(Z-DEVD)-N'-ethoxycarbonyl-Rhodamine 110, SEQ ID NO:5
N-(Z-LEVD)-N'-ethoxycarbonyl-Rhodamine 110, SEQ ID NO:9
N-(Ac-WEHD)-N'-ethoxycarbonyl-Rhodamine 110, SEQ ID NO:1
N-(Ac-YVAD)-N'-ethoxycarbonyl-Rhodamine 110, SEQ ID NO:2
N-(Ac-DEVD)-N'-ethoxycarbonyl-Rhodamine 110, SEQ ID NO:5
N-(Ac-DEHD)-N'-ethoxycarbonyl-Rhodamine 110, SEQ ID NO:6

N-(Ac-DETD)-N'-ethoxycarbonyl-Rhodamine 110, SEQ ID NO:4
N-(Ac-LEVD)-N'-ethoxycarbonyl-Rhodamine 110, SEQ ID NO:9
N-(Ac-LEHD)-N'-ethoxycarbonyl-Rhodamine 110, SEQ ID NO:3
N-(Ac-LETD)-N'-ethoxycarbonyl-Rhodamine 110, SEQ ID NO:8
N-(Ac-VEHD)-N'-ethoxycarbonyl-Rhodamine 110, SEQ ID NO:7
N-(Ac-IEPD)-N'-ethoxycarbonyl-Rhodamine 110, SEQ ID NO:23
N-(Z-WEHD)-N'-hexyloxycarbonyl-Rhodamine 110, SEQ ID NO:1
N-(Z-YVAD)-N'-hexyloxycarbonyl-Rhodamine 110, SEQ ID NO:2
N-(Z-DEVD)-N'-hexyloxycarbonyl-Rhodamine 110, SEQ ID NO:5
N-(Z-LEVD)-N'-hexyloxycarbonyl-Rhodamine 110, SEQ ID NO:9
N-(Ac-WEHD)-N'-hexyloxycarbonyl-Rhodamine 110, SEQ ID NO:1
N-(Ac-YVAD)-N'-hexyloxycarbonyl-Rhodamine 110, SEQ ID NO:2
N-(Ac-DEVD)-N'-hexyloxycarbonyl-Rhodamine 110, SEQ ID NO:5
N-(Ac-DEHD)-N'-hexyloxycarbonyl-Rhodamine 110, SEQ ID NO:6
N-(Ac-DETD)-N'-hexyloxycarbonyl-Rhodamine 110, SEQ ID NO:4
N-(Ac-LEVD)-N'-hexyloxycarbonyl-Rhodamine 110, SEQ ID NO:9
N-(Ac-LEHD)-N'-hexyloxycarbonyl-Rhodamine 110, SEQ ID NO:3
N-(Ac-LETD)-N'-hexyloxycarbonyl-Rhodamine 110, SEQ ID NO:8
N-(Ac-VEHD)-N'-hexyloxycarbonyl-Rhodamine 110, SEQ ID NO:7
N-(Ac-IEPD)-N'-hexyloxycarbonyl-Rhodamine 110, SEQ ID NO:23
N-(Z-WEHD)-N'-octyloxycarbonyl-Rhodamine 110, SEQ ID NO:3
N-(Z-YVAD)-N'-octyloxycarbonyl-Rhodamine 110, SEQ ID NO:2
N-(Z-DEVD)-N'-octyloxycarbonyl-Rhodamine 110, SEQ ID NO:5
N-(Z-LEVD)-N'-octyloxycarbonyl-Rhodamine 110, SEQ ID NO:9
N-(Ac-WEHD)-N'-octyloxycarbonyl-Rhodamine 110, SEQ ID NO:1
N-(Ac-YVAD)-N'-octyloxycarbonyl-Rhodamine 110, SEQ ID NO:2
N-(Ac-DEVD)-N'-octyloxycarbonyl-Rhodamine 110, SEQ ID NO:5
N-(Ac-DEHD)-N'-octyloxycarbonyl-Rhodamine 110, SEQ ID NO:6
N-(Ac-DETD)-N'-octyloxycarbonyl-Rhodamine 110, SEQ ID NO:4
N-(Ac-LEVD)-N'-octyloxycarbonyl-Rhodamine 110, SEQ ID NO:9
N-(Ac-LEHD)-N'-octyloxycarbonyl-Rhodamine 110, SEQ ID NO:3
N-(Ac-LETD)-N'-octyloxycarbonyl-Rhodamine 110, SEQ ID NO:8
N-(Ac-VEHD)-N'-octyloxycarbonyl-Rhodamine 110, SEQ ID NO:7
N-(Ac-IEPD)-N'-octyloxycarbonyl-Rhodamine 110, SEQ ID NO:23
N-(Z-WEHD)-N'-decyloxycarbonyl-Rhodamine 110, SEQ ID NO:1
N-(Z-YVAD)-N'-decyloxycarbonyl-Rhodamine 110, SEQ ID NO:2
N-(Z-DEVD)-N'-decyloxycarbonyl-Rhodamine 110, SEQ ID NO:5
N-(Z-LEVD)-N'-decyloxycarbonyl-Rhodamine 110, SEQ ID NO:9
N-(Ac-WEHD)-N'-decyloxycarbonyl-Rhodamine 110, SEQ ID NO:1
N-(Ac-YVAD)-N'-decyloxycarbonyl-Rhodamine 110, SEQ ID NO:2
N-(Ac-DEVD)-N'-decyloxycarbonyl-Rhodamine 110, SEQ ID NO:5
N-(Ac-DEHD)-N'-decyloxycarbonyl-Rhodamine 110, SEQ ID NO:6
N-(Ac-DETD)-N'-decyloxycarbonyl-Rhodamine 110, SEQ ID NO:4
N-(Ac-LEVD)-N'-decyloxycarbonyl-Rhodamine 110, SEQ ID NO:9
N-(Ac-LEHD)-N'-decyloxycarbonyl-Rhodamine 110, SEQ ID NO:3
N-(Ac-LETD)-N'-decyloxycarbonyl-Rhodamine 110, SEQ ID NO:8
N-(Ac-VEHD)-N'-decyloxycarbonyl-Rhodamine 110, SEQ ID NO:7
N-(Ac-LEPD)-N'-decyloxycarbonyl-Rhodamine 110, SEQ ID NO:23
N-(Z-WEHD)-N'-dodecyloxycarbonyl-Rhodamine 110, SEQ ID NO:1
N-(Z-YVAD)-N'-dodecyloxycarbonyl-Rhodamine 110, SEQ ID NO:2
N-(Z-DEVD)-N'-dodecyloxycarbonyl-Rhodamine 110, SEQ ID NO:5
N-(Z-LEVD)-N'-dodecyloxycarbonyl-Rhodamine 110, SEQ ID NO:29
N-(Ac-WEHD)-N'-dodecyloxycarbonyl-Rhodamine 110, SEQ ID NO:1
N-(Ac-YVAD)-N'-dodecyloxycarbonyl-Rhodamine 110, SEQ ID NO:2
N-(Ac-DEVD)-N'-dodecyloxycarbonyl-Rhodamine 110, SEQ ID NO:5
N-(Ac-DEHD)-N'-dodecyloxycarbonyl-Rhodamine 110, SEQ ID NO:6
N-(Ac-DETD)-N'-dodecyloxycarbonyl-Rhodamine 110, SEQ ID NO:4
N-(Ac-LEVD)-N'-dodecyloxycarbonyl-Rhodamine 110, SEQ ID NO:9
N-(Ac-LEHD)-N'-dodecyloxycarbonyl-Rhodamine 110, SEQ ID NO:3
N-(Ac-LETD)-N'-dodecyloxycarbonyl-Rhodamine 110, SEQ ID NO:8
N-(Ac-VEHD)-N'-dodecyloxycarbonyl-Rhodamine 110, SEQ ID NO:7
N-(Ac-IEPD)-N'-dodecyloxycarbonyl-Rhodamine 110, SEQ ID NO:23
N-(Z-DEVD)-N'-(methylthio)carbonyl-Rhodamine 110, SEQ ID NO:5
N-(Z-YVAD)-N'-(methylthio)carbonyl-Rhodamine 110, SEQ ID NO:2
N-(Z-LEVD)-N'-(methylthio)carbonyl-Rhodamine 110, SEQ ID NO:3
N-(Z-LEHD)-N'-(methylthio)carbonyl-Rhodamine 110, SEQ ID NO:3
N-(Ac-WEHD)-N'-(methylthio)carbonyl-Rhodamine 110, SEQ ID NO:1
N-(Ac-YVAD)-N'-(methylthio)carbonyl-Rhodamine 110, SEQ ID NO:2

N-(Ac-DEVD)-N'-(methylthio)carbonyl-Rhodamine 110, SEQ ID NO:5
N-(Ac-DEHD)-N'-(methylthio)carbonyl-Rhodamine 110, SEQ ID NO:6
N-(Ac-DETD)-N'-(methylthio)carbonyl-Rhodamine 110, SEQ ID NO:4
N-(Ac-LEVD)-N'-(methylthio)carbonyl-Rhodamine 110, SEQ ID NO:9
N-(Ac-LEHD)-N'-(methylthio)carbonyl-Rhodamine 110, SEQ ID NO:3
N-(Ac-LETD)-N'-(methylthio)carbonyl-Rhodamine 110, SEQ ID NO:8
N-(Ac-VEHD)-N'-(methylthio)carbonyl-Rhodamine 110, SEQ ID NO:7
N-(Ac-IEPD)-N'-(methylthio)carbonyl-Rhodamine 110, SEQ ID NO:23
N-(Z-WEHD)-N'-(ethylthio)carbonyl-Rhodamine 110, SEQ ID NO:1
N-(Z-YVAD)-N'-(ethylthio)carbonyl-Rhodamine 110, SEQ ID NO:2
N-(Z-DEVD)-N'-(ethylthio)carbonyl-Rhodamine 110, SEQ ID NO:5
N-(Z-LEVD)-N'-(ethylthio)carbonyl-Rhodamine 110, SEQ ID NO:9
N-(Ac-WEHD)-N'-(ethylthio)carbonyl-Rhodamine 110, SEQ ID NO:5
N-(Ac-YVAD)-N'-(ethylthio)carbonyl-Rhodamine 110, SEQ ID NO:2
N-(Ac-DEVD)-N'-(ethylthio)carbonyl-Rhodamine 110, SEQ ID NO:5
N-(Ac-DEHD)-N'-(ethylthio)carbonyl-Rhodamine 110, SEQ ID NO:6
N-(Ac-DETD)-N'-(ethylthio)carbonyl-Rhodamine 110, SEQ ID NO:4
N-(Ac-LEVD)-N'-(ethylthio)carbonyl-Rhodamine 110, SEQ ID NO:9
N-(Ac-LEHD)-N'-(ethylthio)carbonyl-Rhodamine 110, SEQ ID NO:3
N-(Ac-LETD)-N'-(ethylthio)carbonyl-Rhodamine 110, SEQ ID NO:8
N-(Ac-VEHD)-N'-(ethylthio)carbonyl-Rhodamine 110, SEQ ID NO:7
N-(Ac-IEPD)-N'-(ethylthio)carbonyl-Rhodamine 110, SEQ ID NO:2
N-(Z-WEHD)-N'-(hexylthio)carbonyl-Rhodamine 110, SEQ ID NO:1
N-(Z-YVAD)-N'-(hexylthio)carbonyl-Rhodamine 110, SEQ ID NO:2
N-(Z-DEVD)-N'-(hexylthio)carbonyl-Rhodamine 110, SEQ ID NO:5
N-(Z-LEVD)-N'-(hexylthio)carbonyl-Rhodamine 110, SEQ ID NO:9
N-(Ac-WEHD)-N'-(hexylthio)carbonyl-Rhodamine 110, SEQ ID NO:1
N-(Ac-YVAD)-N'-(hexylthio)carbonyl-Rhodamine 110, SEQ ID NO:2
N-(Ac-DEVD)-N'-(hexylthio)carbonyl-Rhodamine 110, SEQ ID NO:5
N-(Ac-DEHD)-N'-(hexylthio)carbonyl-Rhodamine 110, SEQ ID NO:6
N-(Ac-DETD)-N'-(hexylthio)carbonyl-Rhodamine 310, SEQ ID NO:4
N-(Ac-LEVD)-N'-(hexylthio)carbonyl-Rhodamine 110, SEQ ID NO:9
N-(Ac-LEHD)-N'-(hexylthio)carbonyl-Rhodamine 110, SEQ ID NO:3
N-(Ac-LETD)-N'-(hexylthio)carbonyl-Rhodamine 110, SEQ ID NO:8
N-(Ac-VEHD)-N'-(hexylthio)carbonyl-Rhodamine 110, SEQ ID NO:7
N-(Ac-IEPD)-N'-(hexylthio)carbonyl-Rhodamine 110, SEQ ID NO:23
N-(Z-LEHD)-N'-(octylthio)carbonyl-Rhodamine 110, SEQ ID NO:8
N-(Z-YVAD)-N'-(octylthio)carbonyl-Rhodamine 110, SEQ ID NO:2
N-(Z-DEVD)-N'-(octylthio)carbonyl-Rhodamine 110, SEQ ID NO:5
N-(Z-LEVD)-N'-(octylthio)carbonyl-Rhodamine 110, SEQ ID NO:9
N-(Ac-IEHD)-N'-(octylthio)carbonyl-Rhodamine 110, SEQ ID NO:1
N-(Ac-YVAD)-N'-(octylthio)carbonyl-Rhodamine 110, SEQ ID NO:2
N-(Ac-DEVD)-N'-(octylthio)carbonyl-Rhodamine 110, SEQ ID NO:5
N-(Ac-DEHD)-N'-(octylthio)carbonyl-Rhodamine 110, SEQ ID NO:6
N-(Ac-DETD)-N'-(octylthio)carbonyl-Rhodamine 110, SEQ ID NO:4
N-(Ac-LEVD)-N'-(octylthio)carbonyl-Rhodamine 110, SEQ ID NO:9
N-(Ac-LEHD)-N'-(octylthio)carbonyl-Rhodamine 110, SEQ ID NO:3
N-(Ac-LETD)-N'-(octylthio)carbonyl-Rhodamine 110, SEQ ID NO:8
N-(Ac-VEHD)-N'-(octylthio)carbonyl-Rhodamine 110, SEQ ID NO:7
N-(Ac-IEPD)-N'-(octylthio)carbonyl-Rhodamine 110, SEQ ID NO:23
N-(Z-WEHD)-N'-(decylthio)carbonyl-Rhodamine 110, SEQ ID NO:1
N-(Z-YVAD)-N'-(decylthio)carbonyl-Rhodamine 110, SEQ ID NO:2
N-(Z-DEVD)-N'-(decylthio)carbonyl-Rhodamine 110, SEQ ID NO:5
N-(Z-LEVD)-N'-(decylthio)carbonyl-Rhodamine 110, SEQ ID NO:9
N-(Ac-WEHD)-N'-(decylthio)carbonyl-Rhodamine 110, SEQ ID NO:1
N-(Ac-YVAD)-N'-(decylthio)carbonyl-Rhodamine 110, SEQ ID NO:2
N-(Ac-DEVD)-N'-(decylthio)carbonyl-Rhodamine 110, SEQ ID NO:5
N-(Ac-DEHD)-N'-(decylthio)carbonyl-Rhodamine 110, SEQ ID NO:6
N-(Ac-DETD)-N'-(decylthio)carbonyl-Rhodamine 110, SEQ ID NO:4
N-(Ac-LEVD)-N'-(decylthio)carbonyl-Rhodamine 110, SEQ ID NO:9
N-(Ac-LEHD)-N'-(decylthio)carbonyl-Rhodamine 110, SEQ ID NO:3
N-(Ac-LETD)-N'-(decylthio)carbonyl-Rhodamine 110, SEQ ID NO:8
N-(Ac-VEHD)-N'-(decylthio)carbonyl-Rhodamine 110, SEQ ID NO:7
N-(Ac-IEPD)-N'-(decylthio)carbonyl-Rhodamine 110, SEQ ID NO:23
N-(Z-WEHD)-N'-(dodecylthio)carbonyl-Rhodamine 110, SEQ ID NO:1
N-(Z-YVAD)-N'-(dodecylthio)carbonyl-Rhodamine 110, SEQ ID NO:2
N-(Z-DEVD)-N'-(dodecylthio)carbonyl-Rhodamine 110, SEQ ID NO:5
N-(Z-LEVD)-N'-(dodecylthio)carbonyl-Rhodamine 110, SEQ ID NO:9

N-(Ac-WEHD)-N'-(dodecylthio)carbonyl-Rhodamine 110, SEQ ID NO:1
N-(Ac-YVAD)-N'-(dodecylthio)carbonyl-Rhodamine 110, SEQ ID NO:2
N-(Ac-DEVD)-N'-(dodecylthio)carbonyl-Rhodamine 110, SEQ ID NO:5
N-(Ac-DEHD)-N'-(dodecylthio)carbonyl-Rhodamine 110, SEQ ID NO:6
N-(Ac-DETD)-N'-(dodecylthio)carbonyl-Rhodamine 110, SEQ ID NO:4
N-(Ac-LEVD)-N'-(dodecylthio)carbonyl-Rhodamine 110, SEQ ID NO:9
N-(Ac-LEHD)-N'-(dodecylthio)carbonyl-Rhodamine 110, SEQ ID NO:3
N-(Ac-LETD)-N'-(dodecylthio)carbonyl-Rhodamine 110, SEQ ID NO:8
N-(Ac-VEHD)-N'-(dodecylthio)carbonyl-Rhodamine 110, SEQ ID NO:7
N-(Ac-IEPD)-N'-(dodecylthio)carbonyl-Rhodamine 110, SEQ ID NO:23
N-(Z-WEHD)-N'-(dimethylcarbamyl)-Rhodamine 110, SEQ ID NO:1
N-(Z-YVAD)-N'-(dimethylcarbamyl)-Rhodamine 110, SEQ ID NO:2
N-(Z-DEVD)-N'-(dimethylcarbamyl)-Rhodamine 110, SEQ ID NO:5
N-(Z-LEVD)-N'-(dimethylcarbamyl)-Rhodamine 110, SEQ ID NO:9
N-(Ac-WEHD)-N'-(dimethylcarbamyl)-Rhodamine 110, SEQ ID NO:1
N-(Ac-YVAD)-N'-(dimethylcarbamyl)-Rhodamine 110, SEQ ID NO:2
N-(Ac-DEVD)-N'-(dimethylcarbamyl)-Rhodamine 110, SEQ ID NO:5
N-(Ac-DEHD)-N'-(dimethylcarbamyl)-Rhodamine 110, SEQ ID NO:6
N-(Ac-DETD)-N'-(dimethylcarbamyl)-Rhodamine 110, SEQ ID NO:4
N-(Ac-LEVD)-N'-(dimethylcarbamyl)-Rhodamine 110, SEQ ID NO:9
N-(Ac-LEHD)-N'-(dimethylcarbamyl)-Rhodamine 110, SEQ ID NO:6
N-(Ac-LETD)-N'-(dimethylcarbamyl)-Rhodamine 110, SEQ ID NO:8
N-(Ac-VEHD)-N'-(dimethylcarbamyl)-Rhodamine 110, SEQ ID NO:7
N-(Ac-IEPD)-N'-(dimethylcarbamyl)-Rhodamine 110, SEQ ID NO:23
N-(Z-WEHD)-N'-(N-hexyl-N-methylcarbamyl)-Rhodamine 110, SEQ ID NO:1
N-(Z-YVAD)-N'-(N-hexyl-N-methylcarbamyl)-Rhodamine 110, SEQ ID NO:2
N-(Z-DEVD)-N'-(N-hexyl-N-methylcarbamyl)-Rhodamine 110, SEQ ID NO:25
N-(Z-LEVD)-N'-(N-hexyl-N-methylcarbamyl)-Rhodamine 110, SEQ ID NO:9
N-(Ac-WEHD)-N'-(N-hexyl-N-methylcarbamyl)-Rhodamine 110, SEQ ID NO:1
N-(Ac-YVAD)-N'-(N-hexyl-N-methylcarbamyl)-Rhodamine 110, SEQ ID NO:2
N-(Ac-DEVD)-N'-(N-hexyl-N-methylcarbamyl)-Rhodamine 110, SEQ ID NO:5
N-(Ac-DEHD)-N'-(N-hexyl-N-methylcarbamyl)-Rhodamine 110, SEQ ID NO:6
N-(Ac-DETD)-N'-(N-hexyl-N-methylcarbamyl)-Rhodamine 110, SEQ ID NO:4
N-(Ac-LEVD)-N'-(N-hexyl-N-methylcarbamyl)-Rhodamine 110, SEQ ID NO:9
N-(Ac-LEHD)-N'-(N-hexyl-N-methylcarbamyl)-Rhodamine 110, SEQ ID NO:3
N-(Ac-LETD)-N'-(N-hexyl-N-methylcarbamyl)-Rhodamine 110, SEQ ID NO:8
N-(Ac-VEHD)-N'-(N-hexyl-N-methylcarbamyl)-Rhodamine 110, SEQ ID NO:7
N-(Ac-IEPD)-N'-(N-hexyl-N-methylcarbamyl)-Rhodamine 110, SEQ ID NO:23
N-(Z-DEVD)-N'-methanesulfonyl-Rhodamine 110, SEQ ID NO:5
N-(Z-YVAD)-N'-methanesulfonyl-Rhodamine 110, SEQ ID NO:2
N-(Z-DEVD)-N'-acetyl-Rhodamine 116, SEQ ID NO:5
N-(Z-YVAD)-N'-methanesulfonyl-Rhodamine 116, SEQ ID NO:2
N-(Z-DEVD)-N'-acetyl-Rhodamine 19, SEQ ID NO:5
N-(Z-YVAD)-N'-methanesulfonyl-Rhodamine 19, SEQ ID NO:2
N-(Z-YVAD(OAM))-N'-acetyl-Rhodamine 110, SEQ ID NO:2
N-(Z-LE(OAM)HD(OAM))-N'-acetyl-Rhodamine 110, SEQ ID NO:3
N-(Z-D(OAM)E(OAM)TD(OAM))-N'-acetyl-Rhodamine 110, SEQ ID NO:4
N-(Z-D(OAM)E(OAM)VD(OAM))-N'-acetyl-Rhodamine 110, SEQ ID NO:5
N-(Z-D(OMe)E(OMe)VD(OAM))-N'-acetyl-Rhodamine 110, SEQ ID NO:5
N-(Z-D(OMe)E(OMe)VD)-N'-acetyl-Rhodamine 110, SEQ ID NO:5
N-(Z-VD(OAM))-N'-acetyl-Rhodamine 110, and
N-(Z-E(OAM)VD(OAM))-N'-acetyl-Rhodamine 110.

Another preferred fluorogenic or fluorescent substrates of the present invention are compounds having Formula VIII and include, but are not limited to:
N-(Z-WEHDG)-N'-acetyl-Rhodamine 110, SEQ ID NO:71
N-(Z-YVADG)-N'-acetyl-Rhodamine 110, SEQ ID NO:72
N-(Z-LEHDG)-N'-acetyl-Rhodamine 110, SEQ ID NO:73
N-(Z-LEVDG)-N'-acetyl-Rhodamine 110, SEQ ID NO:74
N-(Z-DETDG)-N'-acetyl-Rhodamine 110, SEQ ID NO:75
N-(Z-DEVDG)-N'-acetyl-Rhodamine 110, SEQ ID NO:76
N-(Ac-LETDG)-N'-acetyl-Rhodamine 110, SEQ ID NO:77
N-(Ac-LEHDG)-N'-acetyl-Rhodamine 110, SEQ ID NO:73
N-(Ac-WEHDG)-N'-methoxycarbonyl-Rhodamine 110, SEQ ID NO:71
N-(Ac-YVADG)-N'-methoxycarbonyl-Rhodamine 110, SEQ ID NO:72
N-(Ac-DEVDG)-N'-methoxycarbonyl-Rhodamine 110, SEQ ID NO:76
N-(Ac-DEHDG)-N'-methoxycarbonyl-Rhodamine 110, SEQ ID NO:78
N-(Z-WEHDGG)-N'-ethoxycarbonyl-Rhodamine 110, SEQ ID NO:79
N-(Z-YVADG)-N'-ethoxycarbonyl-Rhodamine 110, SEQ ID NO:72
N-(Z-DEVDG)-N'-ethoxycarbonyl-Rhodamine 110, SEQ ID NO:76
N-(Z-LEVDG)-N'-ethoxycarbonyl-Rhodamine 110, SEQ ID NO:74
N-(Ac-WEHDG)-N'-ethoxycarbonyl-Rhodamine 110, SEQ ID NO:71
N-(Ac-YVADG)-N'-ethoxycarbonyl-Rhodamine 110, SEQ ID NO:72
N-(Ac-DEVDG)-N'-ethoxycarbonyl-Rhodamine 110, SEQ ID NO:76
N-(Ac-DEHDG)-N'-ethoxycarbonyl-Rhodamine 110, SEQ ID NO:78

N-(Ac-WEHDG)-N'-hexyloxycarbonyl-Rhodamine 110, SEQ ID NO:71
N-(Ac-YVADG)-N'-hexyloxycarbonyl-Rhodamine 110, SEQ ID NO:72
N-(Ac-DEVDG)-N'-hexyloxycarbonyl-Rhodamine 110, SEQ ID NO:76
N-(Ac-DEHDG)-N'-hexyloxycarbonyl-Rhodamine 110, SEQ ID NO:78
N-(Ac-WEHDG)-N'-octyloxycarbonyl-Rhodamine 110, SEQ ID NO:71
N-(Ac-YVADG)-N'-octyloxycarbonyl-Rhodamine 110, SEQ ID NO:72
N-(Ac-DEVDG)-N'-octyloxycarbonyl-Rhodamine 110, SEQ ID NO:76
N-(Ac-DEHDG)-N'-octyloxycarbonyl-Rhodamine 110, SEQ ID NO:78
N-(Ac-WEHDG)-N'-decyloxycarbonyl-Rhodamine 110, SEQ ID NO:71
N-(Ac-YVADG)-N'-decyloxycarbonyl-Rhodamine 110, SEQ ID NO:72
N-(Ac-DEVDG)-N'-decyloxycarbonyl-Rhodamine 110, SEQ ID NO:76
N-(Ac-DEHDG)-N'-decyloxycarbonyl-Rhodamine 110, SEQ ID NO:78
N-(Ac-WEHDG)-N'-dodecyloxycarbonyl-Rhodamine 110, SEQ ID NO:71
N-(Ac-YVADG)-N'-dodecyloxycarbonyl-Rhodamine 110, SEQ ID NO:72
N-(Ac-DEVDG)-N'-dodecyloxycarbonyl-Rhodamine 110, SEQ ID NO:76
N-(Ac-DEHDG)-N'-dodecyloxycarbonyl-Rhodamine 110, SEQ ID NO:78
N-(Ac-WEHDG)-N'-(ethylthio)carbonyl-Rhodamine 110, SEQ ID NO:71
N-(Ac-YVADG)-N'-(ethylthio)carbonyl-Rhodamine 110, SEQ ID NO:72
N-(Ac-DEVDG)-N'-(ethylthio)carbonyl-Rhodamine 110, SEQ ID NO:76
N-(Ac-DEHDG)-N'-(ethylthio)carbonyl-Rhodamine 110, SEQ ID NO:78
N-(Ac-WEHDG)-N'-(hexylthio)carbonyl-Rhodamine 110, SEQ ID NO:71
N-(Ac-YVADG)-N'-(hexylthio)carbonyl-Rhodamine 110, SEQ ID NO:72
N-(Ac-DEVDG)-N'-(hexylthio)carbonyl-Rhodamine 110, SEQ ID NO:76
N-(Ac-DEHDG)-N'-(hexylthio)carbonyl-Rhodamine 110, SEQ ID NO:78
N-(Ac-WEHDG)-N'-(octylthio)carbonyl-Rhodamine 110, SEQ ID NO:71
N-(Ac-YVADG)-N'-(octylthio)carbonyl-Rhodamine 110, SEQ ID NO:72
N-(Ac-DEVDG)-N'-(octylthio)carbonyl-Rhodamine 110, SEQ ID NO:76
N-(Ac-DEHDG)-N'-(octylthio)carbonyl-Rhodamine 110, SEQ ID NO:78
N-(Ac-WEHDG)-N'-(decylthio)carbonyl-Rhodamine 110, SEQ ID NO:71
N-(Ac-YVADGG)-N'-(decylthio)carbonyl-Rhodamine 110, SEQ ID NO:142
N-(Ac-DEVDG)-N'-(decylthio)carbonyl-Rhodamine 110, SEQ ID NO:76
N-(Ac-DEHDG)-N'-(decylthio)carbonyl-Rhodamine 110, SEQ ID NO:78
N-(Ac-WEHDG)-N'-(dodecylthio)carbonyl-Rhodamine 110, SEQ ID NO:71
N-(Ac-YVADG)-N'-(dodecylthio)carbonyl-Rhodamine 110, SEQ ID NO:72
N-(Ac-DEVDG)-N'-(dodecylthio)carbonyl-Rhodamine 110, SEQ ID NO:76
N-(Ac-DEHDG)-N'-(dodecylthio)carbonyl-Rhodamine 110, SEQ ID NO:78
N-(Ac-WEHDG)-N'-(dimethylcarbamyl)-Rhodamine 110, SEQ ID NO:71
N-(Ac-YVADG)-N'-(dimethylcarbamyl)-Rhodamine 110, SEQ ID NO:72
N-(Ac-DEVDG)-N'-(dimethylcarbamyl)-Rhodamine 110, SEQ ID NO:76
N-(Ac-DEHDG)-N'-(dimethylcarbamyl)-Rhodamine 110, SEQ ID NO:78
N-(Ac-WEHDG)-N'-(N-hexyl-N-methylcarbamyl)-Rhodamine 110, SEQ ID NO:71
N-(Ac-YVADG)-N'-(N-hexyl-N-methylcarbamyl)-Rhodamine 110, SEQ ID NO:72
N-(Ac-DEVDG)-N'-(N-hexyl-N-methylcarbamyl)-Rhodamine 110, SEQ ID NO:76
N-(Ac-DEHDG)-N'-(N-hexyl-N-methylcarbamyl)-Rhodamine 110, SEQ ID NO:78
N-(Z-DEVDG)-N'-methanesulfonyl-Rhodamine 110, SEQ ID NO:76
N-(Z-YVADG)-N'-methanesulfonyl-Rhodamine 110, SEQ ID NO:72
N-(Z-DEVDG)-N'-acetyl-Rhodamine 116, SEQ ID NO:76
N-(Z-YVADG)-N'-methanesulfonyl-Rhodamine 116, SEQ ID NO:72
N-(Z-DEVDG)-N'-acetyl-Rhodamine 19, and SEQ ID NO:76
N-(Z-YVADG)-N'-methanesulfonyl-Rhodamine 19 SEQ ID NO:72.

Another preferred fluorogenic or fluorescent substrates of the present invention are compounds having Formula IX and include, but are not limited to:
N-(GP)-N'-octyloxycarbonyl-Rhodamine 110,
N-(GPG)-N'-octyloxycarbonyl-Rhodamine 110,
N-(GP)-N'-ethoxycarbonyl-Rhodamine 110,
N-(GPG)-N'-ethoxycarbonyl-Rhodamine 110,
N-(GPA)-N'-ethoxycarbonyl-Rhodamine 110,
N-(GP)-N'-hexyloxycarbonyl-Rhodamine 110,
N-(GPG)-N'-hexyloxycarbonyl-Rhodamine 110,
N-(GP)-N'-(ethylthio)carbonyl-Rhodamine 110,
N-(GPG)-N'-(ethylthio)carbonyl-Rhodamine 110,
N-(MG)-N'-octyloxycarbonyl-Rhodamine 110,
N-(MA)-N'-octyloxycarbonyl-Rhodamine 110,
N-(MGG)-N'-octyloxycarbonyl-Rhodamine 110,
N-(MGA)-N'-octyloxycarbonyl-Rhodamine 110,
N-(MAG)-N'-octyloxycarbonyl-Rhodamine 110,
N-G-N'-octyloxycarbonyl-Rhodamine 110,
N-(MG)-N'-ethoxycarbonyl-Rhodamine 110,
N-(MA)-N'-ethoxycarbonyl-Rhodamine 110,
N-G-N'-ethoxycarbonyl-Rhodamine 110,
N-(MG)-N'-hexyloxycarbonyl-Rhodamine 110,
N-(MA)-N'-hexyloxycarbonyl-Rhodamine 110,
N-G-N'-hexyloxycarbonyl-Rhodamine 110,
N-(MO)-N'-(ethylthio)carbonyl-Rhodamine 110,
N-G-N'-(ethylthio)carbonyl-Rhodamine 110,
N-(Boc-LM)-N'-octyloxycarbonyl-Rhodamine 110,
N-(Ac-LM)-N'-octyloxycarbonyl-Rhodamine 110,
N-(Boc-LM)-N'-ethoxycarbonyl-Rhodamine 110,
N-(Ac-LM)-N'-ethoxycarbonyl-Rhodamine 110,
N-(Boc-LM )-N'-hexyloxycarbonyl-Rhodamine 110,
N-(Ac-LM)-N'-hexyloxycarbonyl-Rhodamine 110,
N-(Boc-LM)-N'-(ethylthio)carbonyl-Rhodamine 110,
N-(Ac-LM)-N'-(ethylthio)carbonyl-Rhodamine 110,
N-(Ac-SLNFPIV)-N'-octyloxycarbonyl-Rhodamine 110, SEQ ID NO:80

N-(Ac-SLNFPI)-N'-octyloxycarbonyl-Rhodamine 110, SEQ ID NO:81
N-(Ac-SLNFP)-N'-octyloxycarbonyl-Rhodamine 110, SEQ ID NO:82
N-(Ac-LNFPIV)-N'-octyloxycarbonyl-Rhodamine 110, SEQ ID NO:83
N-(Ac-LNFPI)-N'-octyloxycarbonyl-Rhodamine 110, SEQ ID NO:84
N-(Ac-LNFP)-N'-octyloxycarbonyl-Rhodamine 110, SEQ ID NO:85
N-(Ac-RGFP)-N'-octyloxycarbonyl-Rhodamine 110, SEQ ID NO:37
N-(Z-LNFPIV)-N'-octyloxycarbonyl-Rhodamine 110, SEQ ID NO:83
N-(Z-LNFPI)-N'-octyloxycarbonyl-Rhodamine 110, SEQ ID NO:84
N-(Z-LNFP)-N'-octyloxycarbonyl-Rhodamine 110, SEQ ID NO:85
N-(Z-RGFP)-N'-octyloxycarbonyl-Rhodamine 110, SEQ ID NO:37
N-(Z-RQANFLG)-N'-octyloxycarbonyl-Rhodamine 110, SEQ ID NO:31
N-(Z-RQANFL)-N'-octyloxycarbonyl-Rhodamine 110, SEQ ID NO:86
N-(Z-RQANF)-N'-octyloxycarbonyl-Rhodamine 110, SEQ ID NO:387
N-(Z-RKVLFLD)-N'-octyloxycarbonyl-Rhodamine 110, SEQ ID NO:36
N-(Z-RKVLFL)-N'-octyloxycarbonyl-Rhodamine 110, SEQ ID NO:88
N-(Z-RKVLF)-N-octyloxycarbonyl-Rhodamine 110, SEQ ID NO:89
N-(Z-ARVLFLG)-N'-octyloxycarbonyl-Rhodamine 110, SEQ ID NO:90
N-(Z-ARVLFL)-N'-octyloxycarbonyl-Rhodamine 110, SEQ ID NO:91
N-(Z-ARVLF)-N'-octyloxycarbonyl-Rhodamine 110, SEQ ID NO:92
N-(Z-SQNYFLG)-N'-octyloxycarbonyl-Rhodamine 110, SEQ ID NO:93
N-(Z-SQNYFL)-N'-octyloxycarbonyl-Rhodamine 110, SEQ ID NO:94
N-(Z-SQNYF)-N'-octyloxycarbonyl-Rhodamine 110, SEQ ID NO:95
N-(Ac-SLNFPIV)-N'-ethoxycarbonyl-Rhodamine 110, SEQ ID NO:80
N-(Ac-SLNFPI)-N'-ethoxycarbonyl-Rhodamine 110, SEQ ID NO:81
N-(Ac-SLNFP)-N'-ethoxycarbonyl-Rhodamine 110, SEQ ID NO:82
N-(Ac-RGFP)-N'-ethoxycarbonyl-Rhodamine 110, SEQ ID NO:37
N-(Ac-SLNFPIV)-N'-(ethylthio)carbonyl-Rhodamine 110, SEQ ID NO:80
N-(Ac-SLNFPI)-N'-(ethylthio)carbonyl-Rhodamine 110, SEQ ID NO:81
N-(Ac-SLNFP)-N'-(ethylthio)carbonyl-Rhodamine 110, SEQ ID NO:82
N-(Ac-RGFP)-N'-(ethylthio)carbonyl-Rhodamine 110, SEQ ID NO:37
N-(Ac-MRGGG)-N'-octyloxycarbonyl-Rhodamine 110, SEQ ID NO:96
N-(Ac-IRGGG)-N'-octyloxycarbonyl-Rhodamine 110, SEQ ID NO:97
N-(Ac-LVGGG)-N'-octyloxycarbonyl-Rhodamine 110, SEQ ID NO:98
N-(Ac-MVGGG)-N'-octyloxycarbonyl-Rhodamine 110, SEQ ID NO:99
N-(Ac-IVGGG)-N'-octyloxycarbonyl-Rhodamine 110, SEQ ID NO:100
N-(Ac-LRGGG)-N'-octyloxycarbonyl-Rhodamine 110, SEQ ID NO:101
N-(Ac-LRGGA)-N'-octyloxycarbonyl-Rhodamine 110, SEQ ID NO:102
N-(Ac-LRGG)-N'-octyloxycarbonyl-Rhodamine 110, SEQ ID NO:55
N-(Z-LRGGG)-N'-octyloxycarbonyl-Rhodamine 110, SEQ ID NO:101
N-(Z-LRGGA)-N'-octyloxycarbonyl-Rhodamine 110, SEQ ID NO:102
N-(Z-LRGG)-N'-octyloxycarbonyl-Rhodamine 110, SEQ ID NO:55
N-(Ac-LRGGG)-N'-ethoxycarbonyl-Rhodamine 110, SEQ ID NO:101
N-(Ac-LRGGA)-N'-ethoxycarbonyl-Rhodamine 110, SEQ ID NO:102
N-(Ac-LRGG)-N'-ethoxycarbonyl-Rhodamine 110, SEQ ID NO:55
N-(Ac-LRGGG)-N'-(ethylthio)carbonyl-Rhodamine 110, SEQ ID NO:101
N-(Ac-LRGGA)-N=-(ethylthio)carbonyl-Rhodamine 110, SEQ ID NO:102
N-(Ac-LRGG)-N'-(ethylthio)carbonyl-Rhodamine 110, SEQ ID NO:55
N-(Ac-LVLASSS)-N'-octyloxycarbonyl-Rhodamine 110, SEQ ID NO:103
N-(Ac-LVLASS)-N'-octyloxycarbonyl-Rhodamine 110, SEQ ID NO:104
N-(Ac-LVLAS)-N'-octyloxycarbonyl-Rhodamine 110, SEQ ID NO:105
N-(Ac-LVLA)-N'-octyloxycarbonyl-Rhodamine 110, SEQ ID NO:62
N-(Z-LVLASSS)-N'-octyloxycarbonyl-Rhodamine 110, SEQ ID NO:103
N-(Z-LVLASS)-N'-octyloxycarbonyl-Rhodamine 110, SEQ ID NO:104
N-(Z-LVLAS)-N'-octyloxycarbonyl-Rhodamine 110, SEQ ID NO:105
N-(Z-LVLA)-N'-octyloxycarbonyl-Rhodamine 110, SEQ ID NO:62
N-(Ac-LVLASS)-N'-ethoxycarbonyl-Rhodamine 110, SEQ ID NO:104
N-(Ac-LVLAS)-N'-ethoxycarbonyl-Rhodamine 110, SEQ ID NO:105
N-(Ac-LVLA)-N'-ethoxycarbonyl-Rhodamine 110, SEQ ID NO:62
N-(Ac-LVLASS)-N'-(ethylthio)carbonyl-Rhodamine 110, SEQ ID NO:104
N-(Ac-LVLAS)-N'-(ethylthio)carbonyl-Rhodamine 110, SEQ ID NO:105
N-(Ac-LVLA)-N'-(ethylthio)carbonyl-Rhodamine 110, SEQ ID NO:62
N-(Ac-VVNASS)-N'-octyloxycarbonyl-Rhodamine 110, SEQ ID NO:106
N-(Ac-VVNAS)-N'-octyloxycarbonyl-Rhodamine 110, SEQ ID NO:107
N-(Ac-VVNA)-N'-octyloxycarbonyl-Rhodamine 110, SEQ ID NO:64
N-(Ac-Tbg-Tbg-NASS)-N'-octyloxycarbonyl-Rhodamine 110, SEQ ID NO:108
N-(Ac-Tbg-Tbg-NAS)-N'-octyloxycarbonyl-Rhodamine 110, SEQ ID NO:109
N-(Ac-Tbg-Tbg-NA)-N'-octyloxycarbonyl-Rhodamine 110, SEQ ID NO:110
N-(Z-Tbg-Tbg-NASS)-N'-octyloxycarbonyl-Rhodamine 110, SEQ ID NO:108

N-(Z-Tbg-Tbg-NAS)-N'-octyloxycarbonyl-Rhodamine 110, SEQ ID NO:109
N-(Z-Tbg-Tbg-NA)-N'-octyloxycarbonyl-Rhodamine 110, SEQ ID NO:110
N-(Ac-Tbg-Tbg-NASS)-N'-ethoxycarbonyl-Rhodamine 110, SEQ ID NO:108
N-(Ac-Tbg-Tbg-NAS)-N'-ethoxycarbonyl-Rhodamine 110, SEQ ID NO:109
N-(Ac-Tbg-Tbg-NA)-N'-ethoxycarbonyl-Rhodamine 110, SEQ ID NO:110
N-(Ac-Tbg-Tbg-NASS)-N'-(ethylthio)carbonyl-Rhodamine 110, SEQ ID NO:108
N-(Ac-Tbg-Tbg-NAS)-N'-(ethylthio)carbonyl-Rhodamine 110, SEQ ID NO:109
N-(Ac-Tbg-Tbg-NA)-N'-(ethylthio)carbonyl-Rhodamine 110, SEQ ID NO:110
N-(Ac-DDIVPCSMST )-N'-octyloxycarbonyl-Rhodamine 110, SEQ ID NO:111
N-(Ac-DIVPCSMST)-N'-octyloxycarbonyl-Rhodamine 110, SEQ ID NO:112
N-(Ac-IVPCSMST)-N'-octyloxycarbonyl-Rhodamine 110, SEQ ID NO:113
N-(Ac-IVPCSMS)-N'-octyloxycarbonyl-Rhodamine 110, SEQ ID NO:114
N-(Ac-IVPCSM)-N'-octyloxycarbonyl-Rhodamine 110, SEQ ID NO:115
N-(Ac-IVPCS)-N'-octyloxycarbonyl-Rhodamine 110, SEQ ID NO:116
N-(Ac-IVPC)-N'-octyloxycarbonyl-Rhodamine 110, SEQ ID NO:69
N-(Z-IVPCSMST)-N'-octyloxycarbonyl-Rhodamine 110, SEQ ID NO:113
N-(Z-IVPCSMS)-N'-octyloxycarbonyl-Rhodamine 110, SEQ ID NO:114
N-(Z-IVPCSM)-N'-octyloxycarbonyl-Rhodamine 110, SEQ ID NO:115
N-(Z-IVPCS)-N'-octyloxycarbonyl-Rhodamine 110, SEQ ID NO:116
N-(Ac-IVPCSMS)-N'-ethoxycarbonyl-Rhodamine 110, SEQ ID NO:114
N-(Ac-IVPCSM)-N'-ethoxycarbonyl-Rhodamine 110, SEQ ID NO:115
N-(Ac-IVPCS)-N'-ethoxycarbonyl-Rhodamine 110, SEQ ID NO:116
N-(Ac-IVPCSMS)-N'-(ethylthio)carbonyl-Rhodamine 110, SEQ ID NO:114
N-(Ac-IVPCSM)-N'-(ethylthio)carbonyl-Rhodamine 110, and SEQ ID NO:115
N-(Ac-IVPCS)-N'-(ethylthio)carbonyl-Rhodamine 110 SEQ ID NO:116.
where Z is benzyloxycarbonyl, BOC is tert.-butoxycarbonyl, Ac is acetyl, Tbg is t-butylglycine, and AM is acetoxymethyl.

Preferred novel fluorescent dyes of the present invention are compounds having Formula VI and include, but are not limited to:
N-formyl-Rhodamine 110,
N-acetyl-Rhodamine 110,
N-hexanoyl-Rhodamine 110,
N-octanoyl-Rhodamine 110,
N-decanoyl-Rhodamine 110,
N-dodecanoyl-Rhodamine 110,
N-methoxycarbonyl-Rhodamine 110,
N-ethoxycarbonyl-Rhodamine 110,
N-butoxycarbonyl-Rhodamine 110,
N-hexyloxycarbonyl-Rhodamine 110,
N-octyloxycarbonyl-Rhodamine 110,
N-decyloxycarbonyl-Rhodamine 110,
N-odecyloxycarbonyl-Rhodamine 110,
N-benzyloxycarbonyl-Rhodamine 110,
N-(2-butoxyethoxycarbonyl)-Rhodamine 110,
N-(2,5,8-trioxadecyloxycarbonyl)-Rhodamine 110,
N-(methylthio)carbonyl-Rhodamine 110,
N-(ethylthio)carbonyl-Rhodamine 110,
N-(butylthio)carbonyl-Rhodamine 110,
N-(hexylthio)carbonyl-Rhodamine 110,
N-(octylthio)carbonyl-Rhodamine 110,
N-(decylthio)carbonyl-Rhodamine 110,
N-(dodecylthio)carbonyl-Rhodamine 110,
N-methanesulfonyl-Rhodamine 110,
N-ethanesulfonyl-Rhodamine 110,
N-hexanesulfonyl-Rhodamine 110,
N-octanesulfonyl-Rhodamine 110,
N-decanesulfonyl-Rhodamine 110,
N-dodecanesulfonyl-Rhodamine 110,
N-trifluoromethanesulfonyl-Rhodamine 110,
N-dimethylcarbamyl-Rhodamine 110,
N-diethylcarbamyl-Rhodamine 110,
N-(N-methyl-N-hexylcarbamyl)-Rhodamine 110
N-(N-methyl-N-octylcarbamyl)-Rhodamine 110,
N-(N-methyl-N-decylcarbamyl)-Rhodamine 110,
N-acetyl-Rhodamine 116,
N-methoxycarbonyl-Rhodamine 116,
N-ethoxycarbonyl-Rhodamine 116,
N-octyloxycarbonyl-Rhodamine 116,
N-hexyloxycarbonyl-Rhodamine 116,
N-benzyloxycarbonyl-Rhodamine 116,
N-methanesulfonyl-Rhodamine 116,
N-trifluoromethanesulfonyl-Rhodamine 116,
N-octanesulfonyl-Rhodamine 116,
N-acetyl-Rhodamine 19,
N-ethoxycarbonyl-Rhodamine 19,
N-octyloxycarbonyl-Rhodamine 19,
N-methoxycarbonyl-Rhodamine 19, and
N-methanesulfonyl-Rhodamine 19.

Typical aryl groups are $C_{6-10}$ aryl groups including phenyl, naphthyl, fluorenyl and the like, any of which may be substituted with halo or alkyl groups.

Typical alkyl groups are $C_{1-10}$ alkyl groups including methyl, ethyl, propyl, butyl, pentyl, hexyl, heptyl, octyl, nonyl, decyl and branched chain isomers thereof.

Typical acyl (alkanoyl) groups are $C_{2-10}$ alkanoyl groups such as acetyl, propionyl, butanoyl, pentanoyl, hexanoyl and the like as well as the branched chain isomers thereof.

Typical biologically acceptable salts of the compounds of the invention include the sodium, potassium, ammonium, TRIS and the like.

Certain of the compounds of the present invention may be in tautomeric forms, particularly in the y-portion of Formula I. The invention includes all such tautomers. The invention also includes stereoisomers, the racemic mixtures of such stereoisomers as well as the individual entantiomers that may be separated according to methods that are well known to those of ordinary skill in the art.

The compounds of this invention may be prepared using methods known to those skilled in the art. Specifically, compounds with Formulae I–III can be prepared as illustrated by exemplary reactions in Schemes 1–5.

Scheme 1 is the least preferred method since deprotection with HBr/HOAc led to the removal of both the t-butoxy and benzyloxycarbonyl (Z) groups, which makes the next coupling reaction complicated. Thus, where the t-butoxy group is desired, it must be reintroduced. When an N-(9-fluorenylmethoxycarbonyl) (fmoc) group is employed as the N-blocking group (Scheme 2), it can be selectively removed with morpholine, piperidine or other amine base without removing the t-butoxy protecting groups, thus allowing for the ready introduction of additional Z-blocked amino acids or peptides (see Schemes 2–4). The final Z-blocked compounds can be selectively deprotected with trifluoroacetic acid (TFA) to remove the t-butoxy group without removing the Z group.
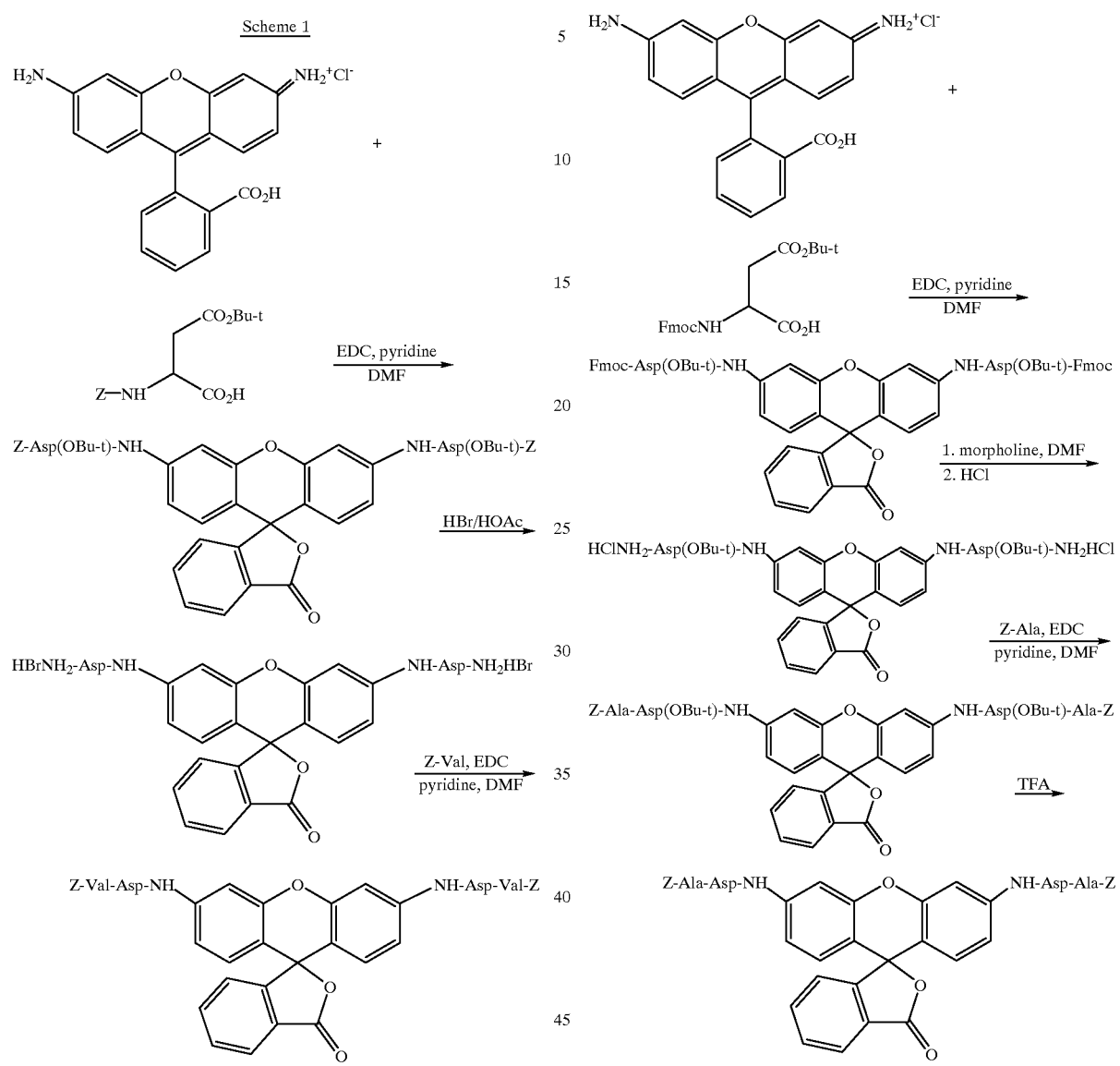
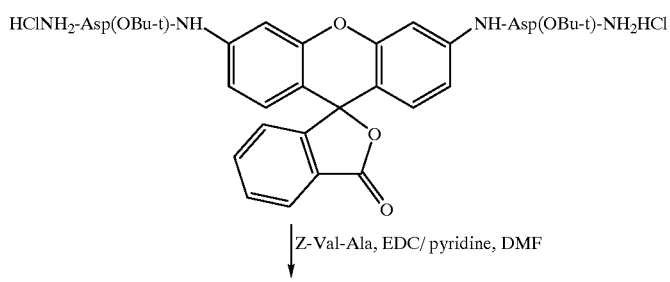

-continued
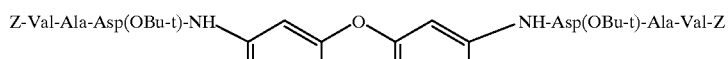
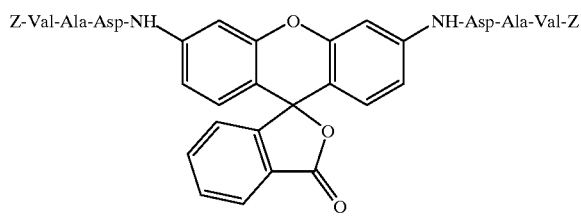
Scheme 4
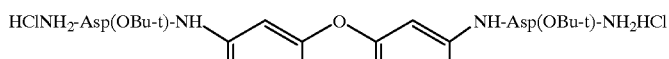
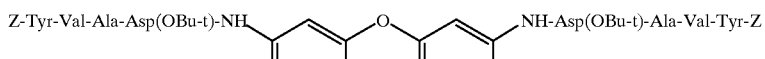
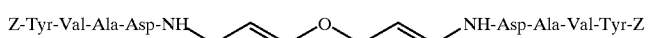

Scheme 5

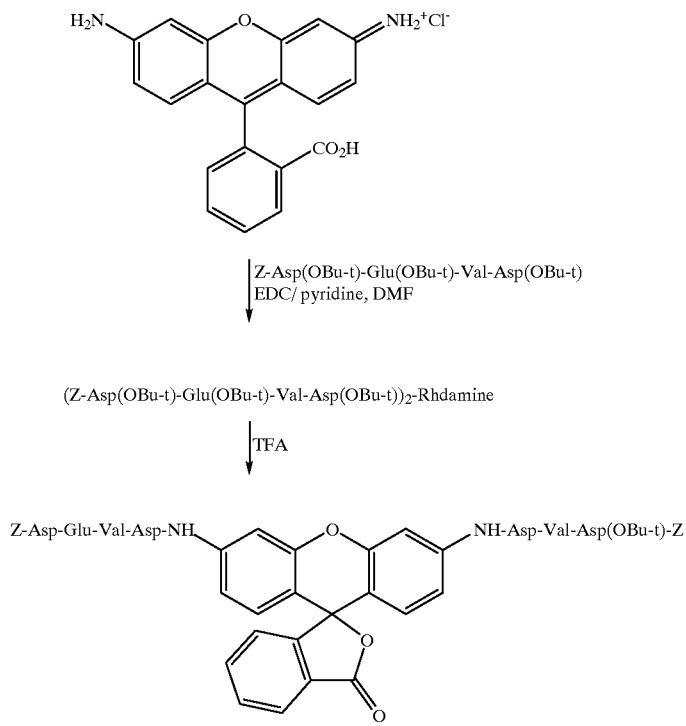

Thus, the invention also relates to a method for the preparation of a compound of Formula III, comprising
(a) condensing Rhodamine 110 together with N-fmoc-L-aspartic acid β-t-butyl ester to give (Fmoc-Asp(OBu-t))$_2$-Rhodamine 110;
(b) removing the Fmoc group to give (Asp(OBu-t))$_2$-Rhodamine 110;
(c) condensing (Asp(OBu-t))$_2$-Rhodamine 110 with Z-(AA)$_n$ to give (Z-(AA)$_n$-Asp(OBu-t))$_2$-Rhodamine 110; and
(d) removing the OBu-t protecting group.

In a preferred embodiment, -(AA)$_n$ is WEH, YVA, LEH, DET, DEV, DEH, VEH, LET, SHV, DEL, DGP, DEP, DGT, DLN, DEE, DSL, DVP, DEA, DSY, ELP, VED, IEP or IET. Where the amino acid is substituted by a carboxy group, it is protected with a OBu-t protecting group which is removed in the final step.

The condensation reaction may be carried out using any conventional condensing agent that is used for peptide synthesis. In a preferred embodiment, the condensing agent is 1-(3-dimethylaminopropyl)-3-ethylcarbodiimide (EDC), or 2-ethoxy-1-ethoxycarbonyl-1,2-dihydroquinoline (EEDQ). The solvent for the reaction may be pyridine or dimethylformamide (DMF). The reaction is generally carried out at room temperature. The ratio of condensing agent to Rhodamine may be about 10:1 and the ratio of protected amino acid or peptide to Rhodamine or (Asp(OBu-t))$_2$-Rhodamine 110 may also be about 10:1.

The Fmoc group is generally removed by treatment with morpholine, piperidine or other amine base, in a polar aprotic solvent such as DMF. In general, the morpholine is added in excess, and the reaction is carried out at room temperature. α,α-Dimethyl-3,5-dimethoxybenzyloxycarbonyl (Ddz) is another N-blocking group which can be used in the place of fmoc. Thus, N-Ddz-L-aspartic acid β-t-butyl ester can be used in place of N-fmoc-L-aspartic acid β-t-butyl ester. Ddz can be cleaved selectively in the presence of t-butoxy group by 1%TFA in methylene chloride.

The OBu-t group is removed with trifluoroacetic acid in an aprotic solvent such as methylene chloride at room temperature.

Compounds with Formula VI can be prepared as illustrated by exemplary reaction in Scheme 6.

Scheme 6

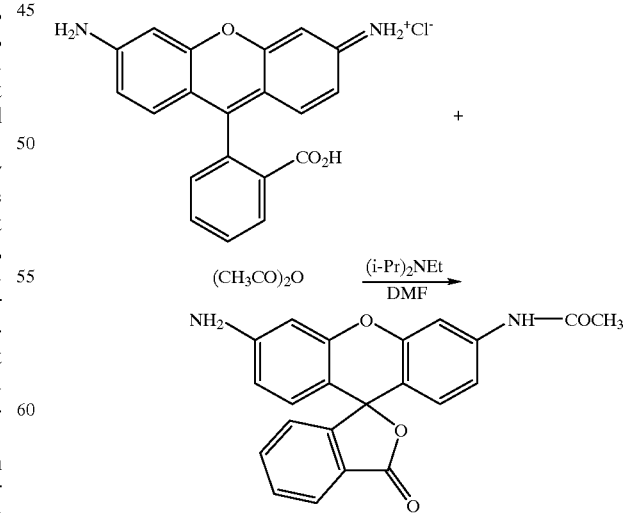

Compounds with Formulae VII–IX can be prepared as illustrated by exemplary reactions in Schemes 7–10.

Scheme 7
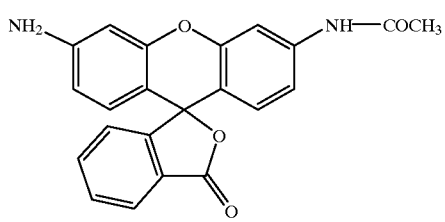
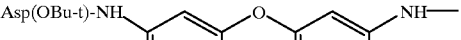
Scheme 8
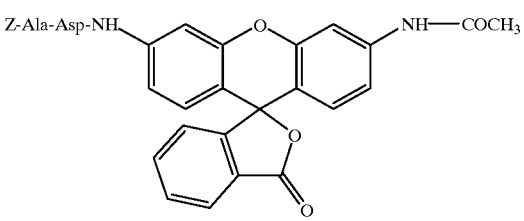
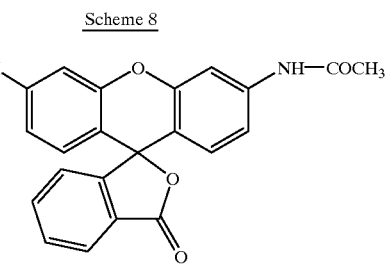
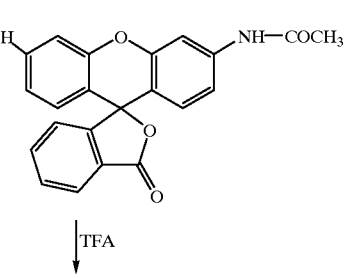
Scheme 9

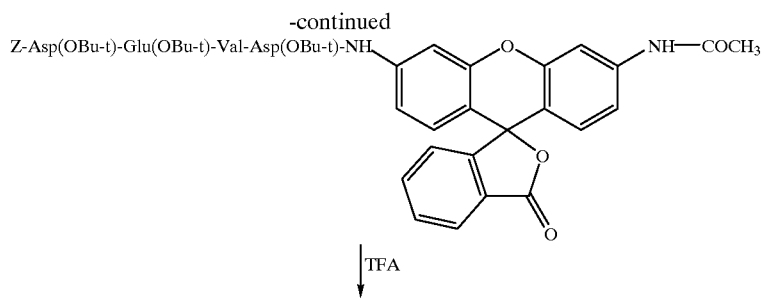

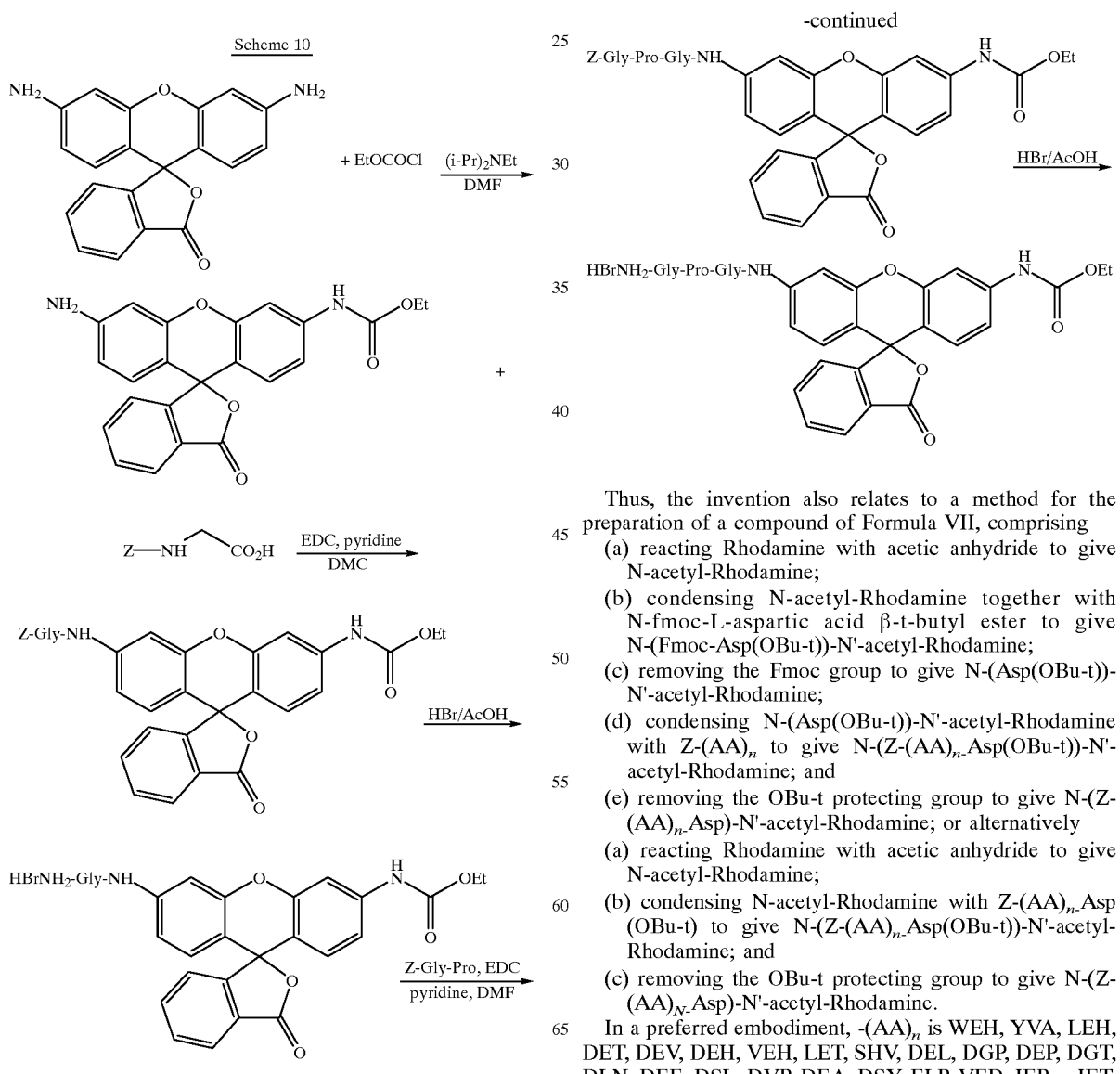

Thus, the invention also relates to a method for the preparation of a compound of Formula VII, comprising
(a) reacting Rhodamine with acetic anhydride to give N-acetyl-Rhodamine;
(b) condensing N-acetyl-Rhodamine together with N-fmoc-L-aspartic acid β-t-butyl ester to give N-(Fmoc-Asp(OBu-t))-N'-acetyl-Rhodamine;
(c) removing the Fmoc group to give N-(Asp(OBu-t))-N'-acetyl-Rhodamine;
(d) condensing N-(Asp(OBu-t))-N'-acetyl-Rhodamine with Z-(AA)$_n$ to give N-(Z-(AA)$_n$-Asp(OBu-t))-N'-acetyl-Rhodamine; and
(e) removing the OBu-t protecting group to give N-(Z-(AA)$_n$-Asp)-N'-acetyl-Rhodamine; or alternatively
(a) reacting Rhodamine with acetic anhydride to give N-acetyl-Rhodamine;
(b) condensing N-acetyl-Rhodamine with Z-(AA)$_n$-Asp(OBu-t) to give N-(Z-(AA)$_n$-Asp(OBu-t))-N'-acetyl-Rhodamine; and
(c) removing the OBu-t protecting group to give N-(Z-(AA)$_N$-Asp)-N'-acetyl-Rhodamine.

In a preferred embodiment, -(AA)$_n$ is WEH, YVA, LEH, DET, DEV, DEH, VEH, LET, SHV, DEL, DGP, DEP, DGT, DLN, DEE, DSL, DVP, DEA, DSY, ELP, VED, IEP or IET.

Compounds of Formula VII also can be prepared using an acyl (alkanoyl) chloride in place of acetic anhydride, such as acetyl chloride, hexanoyl chloride, octanoyl chloride and decanoyl chloride. Other reagents can be used in place of acetic anhydride include, but are not limited to carbamyl chloride such as dimethylcarbamyl chloride, diethylcarbamyl chloride and N-methyl-N-hexylcarbamyl chloride; chloroformate such as methyl chloroformate, ethyl chloroformate, octyl chloroformate, 2-butoxyethyl chloroformate and 2,5,8-trioxadecyl chloroformate; chlorothiolformate such as methyl chlorothiolformate, ethyl chlorothiolformate, octyl chlorothiolformate; alkyl, haloalkyl and aralkyl sulfonyl halides such as methanesulfonyl chloride, octanesulfonyl chloride, trifluoromethanesulfonyl chloride and tosylchloride. The reaction is carried out in the presence of a base, such as $(Et)_3N$, $(i-Pr)_2$-NEt or pyridine. The preferred solvent is DMF. The reaction is generally carried out at room temperature. The ratio of anhydride or acyl chloride to Rhodamine is about 1:1.

The condensation reaction may be carried out using any conventional condensing agent that is used for peptide synthesis. In a preferred embodiment, the condensing agent is EDC or EEDQ, and the solvent for the reaction is pyridine or dimethylformamide (DMF). The reaction is generally carried out at room temperature. The ratio of condensing agent to N-acetyl-Rhodamine is about 3:1 and the ratio of protected amino acid or peptide to N-acetyl-Rhodamine or N-(Asp(OBu-t))-N'-acetyl-Rhodamine is about 3:1.

Condensing N-acetyl-Rhodamine with a peptide such as Z-$(AA)_n$-Asp(OBu-t) to give N-(Z-$(AA)_n$-Asp(OBu-t))-N'-acetyl-Rhodamine in a one-step reaction is a preferred procedure. Thus, compounds of Formula VI provide fluorescent dyes which can be condensed with any peptide or other structure for the preparation of fluorogenic or fluorescent compounds which are substrates for proteases or peptidases.

In principle, compounds of Formula VII also can be prepared by first condensing a peptide with a Rhodamine to give N-peptide-Rhodamine, then reacting the N-peptide-Rhodamine with acetyl anhydride or other acylating reagent to give for example, N-acetyl-N'-peptide-Rhodamine. However, a) peptides in general are much more expensive than acyl chlorides or anhydrides, b) the condensation reaction between peptide and Rhodamine is not an efficient reaction. For these reasons it is preferred to attach the peptide to N-acetyl-Rhodamine rather than attach the acyl group to N-peptide-Rhodamine.

In one aspect, the invention relates to a method for determining whether a test substance has an effect on an enzyme involved in the apoptosis cascade in a test cell, comprising (a) contacting the test cell with the test substance and the reporter compound according to the invention under conditions whereby the test substance either interacts with an external membrane receptor of the cell or is taken into the cell and the reporter compound is taken into the cell, and (b) recording the fluorescence of the test cell, wherein a change in fluorescence, either of magnitude or of wavelength, within the test cell compared to said control cell which has only been contacted with the reporter compound and not with the test substance, is an indication that said test substance has an effect on said enzyme.

The results obtained by this method can be compared to the results obtained with test compounds which are known to affect enzymes involved in the apoptosis cascade in cells to generate a measure of the relative effectiveness of the test substance. Compounds which can be used include known activitors and inhibitors of enzymes involved in the apoptosis cascade. Activators, either by direct or indirect mechanisms, of enzymes involved in the apoptosis cascade include but are not limited to known chemotherapeutic agents, such as etoposide (Yoon H J, Choi I Y, Kang M R, Kim S S, Muller M T, Spitzner J R, Chung I K (1998), *Biochim Biophys Acta* 1395:110–120) and doxorubicin (Gamen S, Anel A, Lasierra P, Alava M A, Martinez-Lorenzo M J, Pineiro A, Naval J (1997), *FEBS Lett* 417:360–364) which are topoisomerase II inhibitors; cisplatin (Maldonado V, Melendez-Zajgla J, Ortega A (1997), *Mutat Res* 381:67–75); chlorambucil (Hickman J A. (1992), *Cancer Metastasis Rev.* 11:121–139) which is an alkylating agent; and fluorouracil, an RNA/DNA anti-metabolite (Hickman J A. (1992), *Cancer Metastasis Rev.* 11:121–139). These activators of apoptosis also can be used to induce apoptosis when screening for inhibitor of apoptosis in whole cells. Inactivators, either by direct or indirect mechanisms, of enzymes involved in the apoptosis cascade include but are not limited to endogenous proteins including Bcl-2 (Joensuu H, Pylkkanen L, Toikkanen S (1994), *Am. J Pathol.* 5:1191–1198), the viral produced agent p35 (Miller L K (1997), *J Cell Physiol.* 173:178–182) and the synthetic caspase inhibitor Z-VAD-FMK (An S, Knox K A (1996), *FEBS Lett.* 386:115–122).

In particular, the invention relates to the use of the reporter compounds having Formulae I–III, V, VII and VIII in whole-cell assays, using whole cells or tissue samples which have been induced to undergo apoptosis, to screen for compounds that inhibit either directly or indirectly an enzyme or enzymes involved in apoptosis (programmed cell death). These screening assays using compounds having Formulae I–III, V, VII and VIII are expected to lead to discovery of new drugs or new uses for known drugs that slow or block cell death in a variety of clinical conditions in which the loss of cells, tissues or entire organs occurs.

The reporter compounds having Formulae I–III, V, VII and VIII and the screening assays of the present invention can be used to identify drugs that reduce or prevent cell death in the nervous system (brain, spinal cord, and peripheral nervous system) under various conditions of ischemia and excitotoxicity, including, but not limited to, focal ischemia due to stroke and global ischemia due to cardiac arrest. The screening assays can also be used to identify compounds that reduce or prevent cell death in the nervous system due to traumatic injury (such as head trauma or spinal cord injury), viral infection or radiation-induced nerve cell death (for example, as a side-effect of cancer radiotherapy) or environmental toxicity (e.g. by certain halogenated hydrocarbon). The screening assays can also be used to identify cell death inhibitors which are useful to reduce or prevent cell death in a range of neurodegenerative disorders, including but not limited to Alzheimer's disease, Huntington's Disease, Parkinson's Disease, multiple sclerosis, amyotrophic lateral sclerosis, and spinobulbar atrophy.

The screening assays of this invention can be used to identify compounds that prevent cell death in any condition which potentially results in the death of cardiac muscle. This includes myocardial infarction, congestive heart failure and cardiomyopathy. One particular application of the screening assay is to identify compounds which reduce or prevent myocardial cell death that occurs in certain viral infections of the heart.

The screening assays of the invention can be used to identify compounds which prevent cell death of retinal neurons that occurs in disorders associated with increased intraocular pressure (such as glaucoma) or retinal disorders associated with the aging process (such as age-related macular degeneration). The assays can also be used to identify compounds which treat hereditary degenerative disorders of the retina, such as retinitis pigmentosa.

The screening assays of the invention can also be used to identify cell death inhibitors that can be used to reduce or prevent premature death of cells in the immune system, and are particularly useful in identifying inhibitors which are useful in treating immune deficiency disorders, such as acquired immune deficiency syndrome (AIDS), severe combined immune deficiency syndrome (SCIDS) and related diseases. The screening assays can also be used to identify cell death inhibitors that can be used to treat radiation-induced immune suppression.

The screening assays of the invention can also be used to identify drugs useful in organ transplantation procedures. Transplantation of human organs and tissues is a common treatment for organ failure. However, during the transplantation process, the donor organ or tissue is at risk for cell death since it is deprived of its normal blood supply prior to being implanted in the host. This ischemic state can be treated with cell death inhibitors by infusion into the donor organ or tissue, or by direct addition of the cell death inhibitors to the organ/tissue storage medium. Such cell death inhibitors can be identified using the screening assays described in this invention. Cell death inhibitors may also be used to reduce or prevent cell death in the donor organ/tissue after it has been transplanted to protect it from the effects of host immune cells which kill their targets by triggering apoptosis. The screening assays described in this invention can be used to identify cell death inhibitors useful in protecting transplanted organs from rejection. The cytoprotective effects of cell death inhibitors can also be used to prevent the death of human or animal sperm and eggs used in in vitro fertilization procedures. These inhibitors can be used during the harvesting process and can also be included in the storage medium. Cell death inhibitors useful for application in fertilization procedures can be identified using the screening assay methods described in this invention.

Mammalian cell lines and yeast cells are commonly used to produce large amounts of recombinant proteins (such as antibodies, enzymes or hormones) for industrial or medicinal use. The lifespan of some of these cell lines is limited due to growth conditions, the nature of the recombinant molecule being expressed (some are toxic) and other unknown factors. The lifespans of industrial cell lines can be extended by including cell death inhibitors in the growth medium. Cell death inhibitors useful in extending the life span of cell lines can be identified using the screening assay procedures described in this invention.

The factors governing hair growth and loss are largely unknown. There is some evidence, however, that hair follicle regression (referred to as catagen) may be due at least partially to apoptosis. Therefore, it is possible that cell death inhibitors can be used to treat hair loss that occurs due to various conditions, including but not limited to male-pattern baldness, radiation-induced or chemotherapy-induced hair loss, and hair loss due to emotional stress. There is also evidence that apoptosis may play a role in the loss of hair color. Therefore, it is possible that cell death inhibitors can also be used in treating cases of premature graying of the hair. Cell death inhibitors useful in treating or preventing hair loss or graying of the hair can be identified using the screening assay procedures described in this invention.

The death of skin epithelial cells can occur after exposure to high levels of radiation, heat or chemicals. It is possible that cell death inhibitors can be used to reduce or prevent this type of skin damage. In one particular application, cell death inhibitors can be applied in an ointment to treat acute over-exposure to the sun and to prevent blistering and peeling of the skin. Cell death inhibitors useful in treating or preventing death of skin cells can be identified using the screening assay procedures described in this invention.

Another important aspect of the present invention is use of the reporter compounds having Formulae I–III, V, VII and VIII in whole-cell assays using live or dead whole cells or tissue samples to screen for compounds that stimulate, either directly or indirectly, an enzyme or enzymes involved in apoptosis. Therefore, these screening assays using compounds having Formulae I–III, V, VII and VIII are expected to lead to discovery of new drugs or new uses for known drugs that act as anti-cancer agents in diseases such as cancers, tumors and cell hyperplasias etc. Compounds that may be found using the screening assays and reagents described herein are useful for treatment of cancers, tumors or tissue hyperplasias including but not limited to cancers or tumors of the brain, peripheral nervous system, eye, ear, nose, mouth, tonsils, teeth, esophagus, lung, heart, blood, blood vessels, bone marrow, lymph nodes, thymus, spleen, immune system, liver, stomach, intestinal tract, pancreas, endocrine glands and tissues, kidney, bladder, reproductive organs and glands, joints, bones and skin.

Another important aspect of the present invention is the use of reporter compounds having Formulae I–III, V, VII and VIII in whole-cell assays using yeast and other fungi, and bacteria to screen compound libraries for anti-fungal or anti-bacterial drugs that act by inducing, either directly or indirectly, the caspase cascade or other enzymes involved in apoptosis in those cells.

Another important aspect of the invention is to use the reporter compounds having Formulae I–III, V, VII and VIII to monitor the therapeutic effects of therapeutic agents or treatments given to patients with the aim of reducing, preventing or treating maladies in which apoptotic cell death is either a cause or a result.

Another important aspect of the present invention is to use the reporter compounds having Formulae IX to screen for HIV protease inhibitors in HIV infected cells, comprising (a) contacting the test cell with the test substance and the reporter compound according to the invention under conditions whereby the test substance either interacts with an external membrane receptor or is taken into said cell and the reporter compound is taken into the cell, and (b) recording the fluorescence of the test cell, wherein a change in fluorescence, either of magnitude or of wavelength, within the test cell compared to a control cell which has only been contacted with the reporter compound and not with the test substance, is an indication that said test substance has an inhibiting effect on the HIV protease.

Yet another important aspect of the present invention is to use the reporter compounds having Formulae IX to diagnose HIV infection, comprising (a) contacting a test cell from an individual suspected of having HIV infection with the reporter compound according to the invention under conditions whereby the reporter compound is taken into the cell, and (b) recording the fluorescence of the test cell, wherein a change in fluorescence, either of magnitude or of wavelength, within the test cell compared to a control cell which is contacted with the reporter compound, is an indication that said test cell has been infected by HIV virus and that the individual has been infected with HIV.

Applying the same procedure for the screening of HIV protease inhibitors in HIV infected cells, the reporter compounds having Formula IX of the present invention can be used to screen for adenovirus protease inhibitors in adenovirus infected cells. The reporter compounds having Formula IX of the present invention also can be used to screen for herpes simplex virus type-1 (HSV-1) protease inhibitors in HSV-1 infected cells. The reporter compounds also can be used to screen for human cytomegalovirus (HCMV) protease inhibitors in HCMV infected cells; to screen for hepatitis C virus (HCV) protease inhibitors in HCV infected cells; to screen for DPP-IV inhibitors in T-cells; as well as to screen for type-2 methionine aminopeptidase (MetAP-2) inhibitors in endothelial cells.

Additionally, using the same procedure for the diagnostics of HIV infection, the reporter compounds having Formula IX of the present invention also can be used to diagnose adenovirus, herpes simplex virus type-1, human cytomegalovirus and hepatitis C virus.

Compositions within the scope of this invention include all compositions wherein the fluorogenic or fluorescent compounds of the present invention are contained in an amount which are effective to achieve its intended purpose. While amounts may vary from assay to assay, determination of optimal ranges of effective amounts of each component is within the skill of the art. Typically, the fluorogenic or fluorescent substrate compounds may be applied to cells or cell lines from mammals, e.g. humans, or other animals by incubating the cells or tissues containing the cells with the fluorogenic or fluorescent substrate at a concentration of about 0.01 nanomolar to about 1 molar, or an equivalent amount of a salt or proreporter molecule thereof in a physiologically compatible buffer. Such buffers include cellular growth medias, an example for leukemia derived cancer cells being RPMI-1640 with or without 10% fetal bovine serum. Other known cellular incubation buffers could involve isotonic solutions buffered with either phosphate or HEPES. One of ordinary skill in the art can identify other suitable buffers with no more than routine experimentation. The cells can be derived from any organ or organ system for which it is desirable to find—by means of the screening assays—drugs that could be useful in treating apoptosis-mediated disorders, e.g., neuronal cell death, heart disease, liver disease, retinal disorders, kidney, joint and bone diseases, immune system disorders, cancers, tumors and tissue hyperplasias etc.

Suitable solubilizers may be used for presenting the fluorogenic or fluorescent compounds of the present invention to tissues, cells or cell lines. Suitable solubilizers include aqueous solutions of the active compounds in water-soluble form, for example, water-soluble salts and alkaline solutions. In addition, suspensions of the compounds as appropriate oily suspensions may be presented to the cells or tissues. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400) or dimethylsulfoxide (DMSO) or another suitable solubilizer. Optionally, the suspension or solution may also contain stabilizers. Optionally, electroporation or presentation of the reporter molecules in liposomes or detergents may be used to enhance the cell permeability of the fluorogenic or fluorescent reporter molecules.

Typically, the cells are contacted with the reporter compounds of the invention and the test substance for about 30 minutes to about 5 hours, most preferably, about 1 hour.

The invention also relates to the pro-reporter derivatives of the compounds of the invention. Such pro-reporter derivatives include compounds which are cleaved in situ by endogenous enzymes to give the compounds of Formulae I–III, V, and VII–IX. Such pro-reporter derivatives include lower alkyl esters of carboxyl-containing amino acid residues such as Asp and Glu. Especially preferred pro-reporter derivatives include the methyl esters and acetoxymethyl (AM) esters of Asp- and Glu-containing compounds.

The following examples demonstrate usefulness of the invention in measuring the activity of caspases and other enzymes involved in apoptosis in cells and tissues. The examples also demonstrate usefulness of the invention in drug screening assays that can be utilized to find enhancers or inhibitors of apoptosis. These examples are illustrative, but not limiting, of the method and compositions of the present invention. Other suitable modifications and adaptations of the variety of conditions and parameters normally encountered in in vitro assays, drug screening procedures or diagnostic procedures which are obvious to those skilled in the art are within the spirit and scope of the invention.

EXAMPLE 1

[Fmoc-Asp(OBu-t)]$_2$-Rhodamine 110

To a solution of Fmoc-L-aspartic acid β-t-butyl ester (4.9 g, 11.91 mmol) dissolved in an anhydrous 1:1 mixture of dimethylformamide and pyridine (30 mL) at 0° C. was added EDC (2.28 g, 11.91 mmol). The solution was stirred for 45 min, then a solution of Rhodamine 110 HCl (0.44 g, 1.19 mmol) in the same solvent (2 mL) was added. The reaction mixture was stirred at room temperature for 60 h and it was concentrated in vacuo to about 10 mL. The residue was then diluted with 100 mL of water and extracted with ethyl acetate (3×50 mL). The organic phase was washed with 1N HCl (2×50 mL) and water (2×50 mL). The solution was dried over Na$_2$SO$_4$ and concentrated to give crude product which was purified by column chromatography (CH$_2$Cl$_2$/EtOAc 10:1), gave 0.89 g (67%) of title compound as colorless solid, mp 156–158° C. $^1$H NMR (CDCl$_3$): δ8.75 (bs, 2H), 8.02 (d,J=9.3 Hz, 2H), 7.80–6.70 (m, 26H), 6.12 (bs, 2H), 4.64 (bs, 2H), 4.46 (d,J=6.8 Hz, 4H), 4.22 (t,J=6.8 Hz, 2H), 2.82 (m, 4H), 1.45 (s, 18H),

EXAMPLE 2

[Asp(OBu-t)]$_2$-Rhodamine 110 2HCl

A chilled solution of DMF/morpholine (3 mL, 1:1) was added dropwise into a stirred solution of [Fmoc-Asp(OBu-t)]$_2$-Rhodamine 110 (150 mg, 0.13 mmol) in dimethylformamide (3 mL). The solution was stirred for 20 min and it was poured into ice water (100 mL) and extracted with ethyl acetate (2×100 mL). The organic phase was washed with water (3×100 mL) and dried over Na$_2$SO$_4$. To the solution was added 1N HCl in ether (0.39 mL) and it was concentrated to give a red solid. The red solid was collected and dissolved in methanol (1 mL), and precipitated with ether (50 mL) to give the title compound (65 mg, 77%) as red solid. m.p. 200° C. (dec).

EXAMPLE 3

[Z-Ala-Asp(OBu-t)]$_2$-Rhodamine 110

From benzyloxycarbonyl-L-alanine (376 mg, 1.69 mmol), EDC (258 mg, 1.35 mmol) and [Asp(OBu-t)]$_2$-Rhodamine 110 2HCl (50 mg, 0.072 mmol) in 1:1 anhydrous DMF/pyridine (10 mL) at 0° C. was obtained 63 mg (86%) of the title compound as a solid, mp 124–126° C. $^1$H NMR (CDCl$_3$): δ8.85 (d, 2H), 7.90 (m, 2H), 7.60 (m, 4H), 7.32 (m, 10H), 7.10 (m, 2H), 6.68 (m, 2H), 5.20 (s, 2H), 5.10 (d, 4H), 4.90 (s, 2H), 4.18 (m, 2H), 2.82 (m, 4H), 1.42 (m, 24H).

EXAMPLE 4

(Z-Ala-Asp)$_2$-Rhodamine 110

To the cooled solution (0° C.) of [Z-Ala-Asp(OBu-t)]$_2$-Rhodamine 110 (41 mg, 0.038 mmol) in methylene chloride (5 ml) was added 50% trifluoroacetic acid in methylene chloride (16 mL). The solution turned orange and was stirred at room temperature for 3 h. The solvent was removed and the crude product was purified by flash column chromatography (EtOAc/CF$_3$CO$_2$H=20:0.5) to yield 34 mg (91%) of the title compound. $^1$H NMR (CD$_3$OD): δ8.02 (d, J=8.1 Hz, 1H), 7.85 (s, 2H), 7.73 (t, J=7.5 Hz, 2H), 7.34–6.60 (m, 15H), 5.08 (d, 4H), 4.05 (m, 2H), 2.95 (m, 4H), 1.38 (d, J=6.4 Hz, 6H).

EXAMPLE 5

[Z-Asp(OBu-t)]$_2$-Rhodamine 110

From benzyloxycarbonyl-L-aspartic acid β-t-butyl ester (4.41 g, 13.63 mmol), EDC (2.61 g, 13.63 mmol) and Rhodamine 110 HCl (0.50 g, 1.36 mmol) in 1:1 anhydrous DMF/pyridine (40 mL) at 0° C. was obtained 1.09 g (82%) of the title compound as colorless solid. mp 127–129° C. $^1$H NMR (CDCl$_3$): δ8.75 (bs, 2H), 8.06 (d, J=6.3 Hz, 2H), 7.68–7.56 (m, 4H), 7.40–6.60 (m, 15H), 6.12 (bs, 2H), 5.16 (s, 4H), 4.62 (bs, 2H), 2.97 (dd, J$_1$=17.1 Hz, J$_2$=3.3 Hz, 2H), 2.69 (dd, J$_1$=17.3 Hz, J$_2$=6.9 Hz, 2H), 1.44 (s, 18H).

EXAMPLE 6

(Asp)$_2$-Rhodamine 110 2HBr

A chilled solution of 30% HBr in acetic acid (5 mL) was added dropwise into a stirred solution of [Z-Asp(OBu-t)]$_2$-Rhodamine 110 (200 mg, 0.21 mmol) in acetic acid (2 mL). The solution was stirred at room temperature for 1 h and it was then concentrated in vacuo. To the residue was added 100 mL of anhydrous ether to give a red precipitate which was isolated after centrifugation to give 118 mg (78%) of solid, mp 130° C. $^1$H NMR (DMSO-d$_6$): δ10.81 (s, 2H), 8.35 (bs, 6H), 8.05–6.79 (m, 10H), 4.25 (bs, 2H), 2.96 (m, 4H).

EXAMPLE 7

(Z-Val-Asp)$_2$-Rhodamine 110

From benzyloxycarbonyl-L-valine (628 mg, 2.5 mmol), EDC (383 mg, 2 mmol) and (Asp)$_2$-Rhodamine 110 2HBr (72 mg, 0.1 mmol) in 1:1 anhydrous DMF/pyridine (12 mL) at 0° C. was obtained 38 mg (37%) of the title compound, mp 169–171° C. $^1$H NMR (DMSO): δ8.70 (d, 2H), 8.04 (d, J=7.5 Hz, 1H), 7.80 (m, 2H), 7.48–7.20 (m, 11H), 7.05 (m, 2H), 5.02 (bs, 4H), 4.70 (m, 2H), 3.85 (t, 2H), 3.20 (m, 2H), 2.60 (m, 2H), 2.05 (bs, 2H), 0.85 (t, 12H).

EXAMPLE 8

[Z-Val-Ala-Asp(OBu-t)]$_2$-Rhodamine 110

From benzyloxycarbonyl-L-Val-L-Ala (200 mg, 0.62 mmol), EDC (110 mg, 0.57 mmol) and [Asp(OBu-t)]$_2$-Rhodamine 110 2HCl (31 mg, 0.043 mmol) in 1:1 anhydrous DMF/pyridine at 0° C. was obtained 45 mg (85%) of the title compound, mp 85–87° C. $^1$H NMR (CDCl$_3$): δ9.10 (bs, 1H), 8.90 (bs, 1H), 8.80 (d, 1H), 7.80–6.60 (m, 19H), 5.42 (bs, 2H), 5.10 (bs, 4H), 4.90 (s, 2H), 4.00 (d, 2H), 2.90 (m, 4H), 2.12 (m, 2H), 1.35 (s, 18H), 1.30 (d, J=6.4 Hz, 6H), 0.92 (m, 12H).

EXAMPLE 9

(Z-Val-Ala-Asp)$_2$-Rhodamine 110

From [Z-Val-Ala-Asp(OBu-t)]$_2$-Rhodamine 110 (28 mg, 0.022 mmol) and 50% trifluoroacetic acid in methylene chloride (30 mL) at 0° C. was obtained 23 mg (88%) of the title compound. $^1$H NMR (CD$_3$OD): δ8.00 (s, 1H), 7.92 (bs, 1H), 7.86 (bs, 1H), 7.70 (m, 2H), 7.40–7.21 (m, 13H), 6.70 (s, 1H), 6.68 (s, 1H), 5.08 (d, 4H), 4.22 (m, 2H), 3.90 (m, 2H), 2.92 (m, 4H), 2.06 (m, 2H), 1.34 (d, J=6.4 Hz, 6H), 0.95 (m, 12H).

EXAMPLE 10

[Z-Tyr-Val-Ala-Asp(OBu-t)]$_2$-Rhodamine 110 SEQ ID NO:2

From benzyloxycarbonyl-L-Tyr-L-Val-L-Ala (339 mg, 0.70 mmol), EDC (122 mg, 0.64 mmol) and [Asp(OBu-t)]$_2$-Rhodamine 110 2HCl (39 mg, 0.058 mmol) in 1:1 anhydrous DMF/pyridine at 0° C. was obtained 61 mg (65%) of the title compound, mp 155–157° C. $^1$H NMR (CD$_3$OD): δ8.02–6.60 (m, 28H), 5.02 (bs, 4H), 4.92 (t, 2H), 4.80 (t, 2H), 4.38 (m, 2H), 4.22 (m, 2H), 3.05–2.62 (m, 8H), 2.02 (m, 2H), 1.42 (s, 18H), 1.32 (d, J=6.6 Hz, 6H), 0.92 (m, 12H).

EXAMPLE 11

(Z-Tyr-Val-Ala-Asp)$_2$-Rhodamine 110 SEQ ID NO:2

From [Z-Tyr-Val-Ala-Asp(OBu-t)]$_2$-Rhodamine 110 SEQ ID NO:2 (47 mg, 0.029 mmol) and 50% trifluoroacetic acid in methylene chloride (30 mL) at 0° C. was obtained 36 mg (82%) of the title compound, mp 115° C. $^1$H NMR (CD$_3$OD): δ8.02 (bs, 2H), 7.82 (bs, 2H), 7.70 (m, 2H), 7.40–6.60 (m, 22H), 5.02 (bs, 4H), 4.80 (m, 2H), 4.38 (m, 2H), 4.22 (m, 2H), 4.10 (m, 2H), 3.10–2.60 (m, 6H), 2.06 (m, 2H), 1.36 (d, J=7.2 Hz, 6H), 0.91 (d, J=7.5 Hz, 12H).

EXAMPLE 12

N-Acetyl-Rhodamine 110

To a solution of Rhodamine 110 (500 mg, 1.36 mmol) dissolved in DMF (20 mL) at 0° C. was added N,N-diisopropylethylamine (176 mg, 1.36 mmol), then acetic anhydride (167 mg, 1.64 mmol) was added dropwise to the above solution. The reaction solution was stirred at room temperature for 24 h, and it was then diluted with 100 mL of water and extracted with ethyl acetate (3×50 mL). The organic phase was washed with water (2×100 mL), dried over Na$_2$SO$_4$ and concentrated to give crude product which was purified by column chromatography (Hexane/EtOAc 1:1) to give 210 mg (41%) of the title compound as colorless solid, mp 179° C. (dec). R$_f$=0.36 (EtOAc/CH$_2$Cl$_2$=1:1). $^1$H NMR (CDCl$_3$): δ8.00 (d, J=6.7 Hz, 1H), 7.78–7.52 (m, 4H), 7.14 (d, J=6.7 Hz, 1H), 6.93 (d, J=6.7 Hz, 1H), 6.64 (d, J=7.9 Hz, 1H), 6.54–6.28 (m, 3H), 3.86 (bs, 2H), 2.15 (s, 3H).

EXAMPLE 13

N-[Fmoc-Asp(OBu-t)]-N'-acetyl-Rhodamine 110

From Fmoc-L-aspartic acid t-butyl ester (739 mg, 1.79 mmol), EDC (302 mg, 1.57 mmol) and N-acetyl-Rhodamine 110 (160 mg, 0.43 mmol) in 1:1 anyhydrous DMF/pyridine (8 mL) at 0° C. was obtained 276 mg (84%) of the title compound as colorless solid. $R_f$=0.75 (EtOAc/CH$_2$Cl$_2$=1:1). $^1$H NMR (CDCl$_3$): δ8.72 (bs, 1H), 8.02 (d, J=6.3 Hz, 1H), 7.80–6.68 (m, 17H), 6.12 (bs, 1H), 4.63 (bs, 1H), 4.47 (d, J=5.5 Hz, 2H), 4.22 (t, J=7.2 Hz, 1H), 2.96 (m, 1H), 2.68 (m, 1H), 2.20 (s, 3H), 1.46 (s, 9H).

EXAMPLE 14

N-[Asp(OBu-t)]-N'-acetyl-Rhodamine 110

From a chilled solution of DMF/morpholine (3 mL, 1:1) and N-[Fmoc-Asp(OBu-t)]-N'-acetyl-Rhodamine 110 (100 mg, 0.13 mmol) was obtained the title compound (67 mg, 95%) as solid, mp 131–133° C. $^1$H NMR (CDCl$_3$): δ9.73 (s, 1H), 8.01 (d, J=7.2 Hz, 1H), 7.72 (s, 1H), 7.70–6.65 (m, 9H), 3.80 (m, 1H), 2.88 (d, J=16.5 Hz, 1H), 2.70 (m, 1H), 2.17 (s, 3H), 1.90 (bs, 2H), 1.44(s, 9H).

EXAMPLE 15

N-[Z-Ala-Asp(OBu-t)]-N'-acetyl-Rhodamine 110

From benzyloxycarbonyl-L-alanine (43 mg, 0.19 mmol), EDC (37 mg, 0.19 mmol) and N-Asp(OBu-t)-N'-acetyl-Rhodamine 110 (30 mg, 0.055 mmol) in 1:1 anyhydrous DMF/pyridine at 0° C. was obtained 38 mg (92%) of the title compound as a solid, mp 138–140° C. $R_f$=0.42 (EtOAc/Hexane 4:1). $^1$H NMR (CDCl$_3$): δ8.82 (bs, 1H), 8.01 (d, J=6.6 Hz, 1H), 7.70–6.67 (m, 14H), 5.20 (m, 1H), 5.16 (bs, 2H), 4.90 (m, 1H), 4.20 (m, 1H), 3.12 (m, 1H), 2.61 (m, 1H), 2.19 (s, 3H), 1.56(bs, 3H), 1.43 (s, 9H).

EXAMPLE 16

N-(Z-Ala-Asp)-N'-acetyl-Rhodamine-110

From N-[Z-Ala-Asp(OBu-t)]-N'-acetyl-Rhodamine 110 (38 mg, 0.052 mmol) and 50% trifluoroacetic acid in methylene chloride (3 mL) at 0° C. was obtained 34 mg (96%) of the title compound. $R_f$=0.6 (10 mL EtOAc with 5 drops of CF$_3$CO$_2$H). $^1$H NMR (CD$_3$OD): δ8.02 (d, J=7.5 Hz, 1H), 7.80–6.69 (m, 14H), 5.10 (bs, 2H), 2.92 (m, 2H), 2.14 (s, 3H), 1.37 (d, J=7.5 Hz, 3H).

EXAMPLE 17

N-[Z-Val-Asp(OBu-t)]-N'-acetyl-Rhodamine 110

From benzyloxycarbonyl-L-valine (49 mg, 0.19 mmol), EDC (37 mg, 0.19 mmol) and N-Asp(OBu-t)-N'-acetyl-Rhodamine 110 (30 mg, 0.055 mmol) in 1:1 anyhydrous DMF/pyridine (4 mL) at 0° C. was obtained 40 mg (94%) of the title compound as a solid, mp 155–157° C. $R_f$=0.5 (EtOAc/Hexane 4:1). $^1$H NMR (CDCl$_3$): δ8.87 (s, 1H), 8.01 (d, J=7.5 Hz, 1H), 7.64–6.66 (m, 14H), 5.32 (bs, 1H), 5.11 (d, J=3.3 Hz, 2H), 4.92 (m, 1H), 4.02 (m, 1H), 3.06 (d, J=15.6 Hz, 1H), 2.62 (m, J=15.8 Hz, 1H), 2.20 (s, 3H), 1.43 (s, 9H), 1.26 (bs, 1H), 0.96 (m, 6H).

EXAMPLE 18

N-(Z-Val-Asp)-N'-acetyl-Rhodamine 110

From N-[Z-Val-Asp(OBu-t)]-N'-acetyl-Rhodamine 110 (40 mg, 0.051 mmol) and 50% trifluoroacetic acid in methylene chloride (3 mL) at 0° C. was obtained 37 mg (99%) of the title compound. $R_f$=0.6 (10 mL EtOAc with 5 drops CF$_3$CO$_2$H). $^1$H NMR (CD$_3$OD): δ8.01 (d, J=7.5 Hz, 1H), 7.78–6.60 (m, 14H), 5.08 (d, J=6.5 Hz, 2H), 4.83 (m, 1H), 3.89 (d, J=5.7 Hz, 1H), 3.02 (m, 1H), 2.85 (m, 1H), 2.14 (s, 3H), 1.25 (m, 1H), 0.97 (bs, 6H).

EXAMPLE 19

N-[Z-Val-Ala-Asp(OBu-t)]-N'-acetyl-Rhodamine 110

From benzyloxycarbonyl-L-valine-L-alanine (63 mg, 0.019 mmol), EDC (37 mg, 0.019 mmol) and N-Asp(OBu-t)-N'-acetyl-Rhodamine 110 (30 mg, 0.052 mmol) in 1:1 anyhydrous DMF/pyridine at 0° C. was obtained 40 mg (97%) of the title compound, mp 101–103° C. $R_f$=0.35 (EtOAc/Hexane 6:1). $^1$H NMR (CDCl$_3$): δ7.99 (d, J=8.4Hz), 7.80–6.62 (m, 14H), 5.42 (m, 1H), 5.11 (bs, 2H), 4.90 (m, 1H), 4.40 (bs, 1H), 4.08 (m, 1H), 3.68 (bs, 2H), 3.50 (m, 1H), 2.90 (m, 2H), 2.16 (bs, 3H), 1.41 (s, 9H), 1.26 (d, J=6.3 Hz, 3H), 1.25 (m, 1H), 0.93 (m, 6H).

EXAMPLE 20

N-(Z-Val-Ala-Asp)-N'-acetyl-Rhodamine 110

From N-[Z-Val-Ala-Asp(OBu-t)]-N'-acetyl-Rhodamine 110 (36 mg, 0.043 mmol) and 50% trifluoroacetic acid in methylene chloride (4 mL) at 0° C. was obtained 35 mg (100%) of the title compound. $R_f$=0.4 (10 mL EtOAc with 4 drops of CF$_3$CO$_2$H). $^1$H NMR (CD$_3$OD): δ8.02 (d, J=5.7 Hz, 1H), 7.95–7.12 (m, 12H), 6.71 (s, 1H), 6.68 (s, 1H), 5.09 (bs, 2H), 4.82 (m, 1H), 4.25 (m, 1H), 3.88 (m, 1H), 3.64 (bs, 1H), 2.94 (m, 2H), 2.14 (s, 3H), 1.30 (d, J=6.0 Hz, 3H), 0.95 (d, J=6.9 Hz, 6H).

EXAMPLE 21

N-[Z-Tyr-Val-Ala-Asp(OBu-t)]-N'-acetyl-Rhodamine 110 SEQ ID NO:2

From benzyloxycarbonyl-L-tyrosine-L-valine-L-alanine (119 mg, 0.25 mmol), EDC (47 mg, 0.25 mmol) and N-Asp(OBu-t)-N'-acetyl-Rhodamine 110 (30 mg, 0.055 mmol) in 1:1 anyhydrous DMF/pyridine at 0° C. was obtained 50 mg (95%) of the title compound. $R_f$=0.5 (EtOAc). $^1$H NMR (CD$_3$OD): δ8.02 (d, J=7.8 Hz, 1H), 7.82–6.58 (m, 18H), 4.90 (m, 2H), 4.35 (m, 1H), 4.24 (m, 1H), 4.08 (m, 1H), 2.93 (m, 1H), 2.73 (m, 1H), 2.13 (s, 3H), 1.43 (s, 9H), 1.37 (d, J=7.2 Hz, 3H), 1.29 (bs, 1H), 0.91 (m, 6H).

EXAMPLE 22

N-(Z-Tyr-Val-Ala-Asp)-N'-acetyl-Rhodamine 110 SEQ ID NO:2

From N-[Z-Tyr-Val-Ala-Asp(OBu-t)]-N'-acetyl-Rhodamine 110 SEQ ID NO:2 (49 mg, 0.049 mmol) and 50% trifluoroacetic acid in methylene chloride (4 mL) at 0° C. was obtained 42 mg (89%) of the title compound. $R_f$=0.62 (10 mL EtOAc with 5 drops CF$_3$CO$_2$H). $^1$H NMR (CD$_3$OD): δ8.00 (d, J=7.2 Hz, 1H), 7.84–6.56 (m, 18H), 4.99 (bs, 2H), 4.80 (m, 1H), 4.32 (m, 1H), 4.23 (m, 1H), 4.10 (m, 1H), 2.97 (m, 2H), 2.13 (s, 3H), 1.37 (d, J=6.9 Hz, 3H), 1.23 (m, 1H), 0.90 (m, 6H).

EXAMPLE 23

N-[Z-Asp(OBu-t)-Glu(OBu-t)-Val-Asp(OBu-t)]-N'-acetyl-Rhodamine 110 SEQ ID NO:5

From benzyloxycarbonyl-L-Asp(OBu-t)-L-Glu(OBu-t)-L-Val-L-Asp(OBu-t) (262 mg, 0.34 mmol), EDC (65 mg, 0.34 mmol) and N-acetyl-Rhodamine 110 (30 mg, 0.08 mmol) in 1:1 anyhydrous DMF/pyridine (4 mL) at 0° C. was obtained 73 mg (81%) of the title compound, mp 127–129° C. $R_f$=0.69 (EtOAc/CH$_2$Cl$_2$=1:1). $^1$H NMR (CDCl$_3$): δ9.05 (s, 1H), 8.79 (d, J=10.8 Hz, 1H), 8.38 (bs, 1H), 8.01–6.65 (m, 15H), 6.10 (m, 1H), 5.14 (m, 2H), 4.92 (bs, 1H), 4.52 (m, 1H), 4.42 (m, 1H), 4.18 (m, 1H), 3.92 (m, 1H), 3.10–2.64 (m, 4H), 2.48 (m, 2H), 2.17 (bs, 3H), 1.40 (m, 27H), 0.99 (bs, 6H).

EXAMPLE 24

N-(Z-Asp-Glu-Val-Asp)-N'-acetyl-Rhodamine 110 SEQ ID NO:5

From N-[Z-Asp(OBu-t)-Glu(OBu-t)-Val-Asp(OBu-t)]-N'-acetyl-Rhodamine 110 SEQ ID NO:5 (49 mg, 0.043 mmol) and 50% trifluoroacetic acid in methylene chloride (5 mL) at 0° C. was obtained 38 mg (92%) of the title compound. $R_f$=0.52 (10 mL EtOAc with 5 drops of CF$_3$CO$_2$H). $^1$H NMR (CD$_3$OD): δ8.04–6.63 (m, 15H), 5.05 (m, 2H), 4.50 (m, 1H), 4.40 (m, 1H), 4.05 (m, 1H), 3.93 (d, J=7.9 Hz, 1H), 3.10–2.61 (m, 4H), 2.37 (m, 2H), 2.13 (s, 3H), 0.97 (m, 6H).

EXAMPLE 25

N-Ethoxycarbonyl-Rhodamine 110

To a solution of Rhodamine 110 (3.00 g, 8.18 mmol) dissolved in dimethylformamide (140 mL) at –50 ° C. was added N,N-diisopropylethylamine (1.27 g, 1.2 mmol), then ethyl chloroformate (1.07 g, 9.81 mmol) was added dropwise to the above solution. The reaction solution was then slowly warmed to room temperature and kept stirring for 5 h. It was then diluted with 200 mL of ice water and extracted with ethyl acetate (3×50 mL). The organic phase was washed with brine water (3×100 mL), dried over Na$_2$SO$_4$ and concentrated to give crude product which was purified by column chromatography (hexane/EtOAc 3:1) to give 1.31 g (40%) of the title compound as colorless solid. $R_f$=0.4 (EtOAc/Hexane=2:1). $^1$H NMR (CDCl$_3$): δ8.00 (d, J=6.9 Hz, 1H), 7.65–7.50 (m, 4H), 7.15 (d, J=7.2 Hz, 1H), 6.88–6.32 (m, 8H), 4.24(q, J=7.2 Hz, 2H), 3.92 (bs, 2H), 1.33 (t, J=7.2 Hz, 3H).

EXAMPLE 26

N-[Cbz-Val-Asp(OBu-t)]-N'-Ethoxycarbonyl-Rhodamine 110

From Cbz-Val-Asp(OBu-t) (197 mg, 0.47 mmol), EDC (89.53 mg, 0.47 mmol) and N-ethoxycarbonyl-Rhodamine 110 (47 mg, 0.12 mmol) (as described in Example 1) was obtained 47 mg (50%) of the title compound as a solid. $^1$H NMR (CDCl$_3$): δ9.04 (bs, 1H), 8.00 (d, J=6.9 Hz, 1H), 7.82–6.62 (m, 15H), 5.30 (bs, 1H), 5.20–5.11 (m, 2H), 4.98 (m, 1H), 4.23 (q, J=6.9 Hz, 2H), 3.74 (t, 1H), 3.15 (d, J=16.5 Hz, 1H), 2.59 (m, 1H), 2.10 (m, 1H), 1.45 (s, 9H), 1.32 (t, J=6.9 Hz, 3H), 1.01 (m, 6H).

EXAMPLE 27

N-(Cbz-Val-Asp)-N'-Ethoxycarbonyl-Rhodamine 110

From N-[Z-Val-Asp(OBu-t)]-N'-ethoxycarbonyl Rhodamine 110 (20 mg, 0.025 mmol) in 50% trifluoroacetic acid in methylene chloride (2 mL) was obtained 15 mg (80%) of the title compound. $^1$H NMR (CD$_3$OD): δ8.02 (d, J=6.6 Hz, 1H), 7.86–6.59 (m, 14H), 5.10 (m, 2H), 4.97 (m, 1H), 4.20 (q, J=6.9 Hz, 2H), 3.77 (d, J=8.1 Hz, 1H), 3.04 (m, 1H), 2.76 (m, 1H), 2.00 (m, 1H), 1.32 (t,J=7.2 Hz, 3H), 1.02 (m, 6H).

EXAMPLE 28

N-[Cbz-Asp(OBu-t)-Glu(OBu-t)-Val-Asp(OBu-t)]-N'-ethoxycarbonyl-Rhodamine 110 SEQ ID NO:5

From Cbz-Asp(OBu-t)-Glu(OBu-t)-Val-Asp(OBu-t) SEQ ID NO:5 (374 mg, 6.48 mmol), EDC (92 mg, 0.48 mmol) and N-ethoxycarbonyl-Rhodamine 110 (48.28 mg, 0.12 mmol) (as described in Example 1) was obtained 81 mg (58%) of the title compound as a solid. $^1$H NMR (CDCl$_3$): δ9.02 (bs, 1H), 8.80 (d, 1H), 8.00–6.78 (m, 15H), 6.18–6.02 (m, 1H), 5.13 (bs, 2H), 4.94 (bs, 1H), 4.60 (bs, 1H), 4.44 (bs, 1H), 4.22 (m, 2H), 3.89 (m, 1H), 3.15–2.00 (m, 8H), 1.46–1.31 (m, 27H), 1.26 (m, 1H), 1.05–0.98 (m, 9H).

EXAMPLE 29

N-(Cbz-Asp-Glu-Val-Asp)-N'-ethoxycarbonyl-Rhodamine 110 SEQ ID NO:5

From N-[Z-Asp(OBu-t)-Glu(OBu-t)-Val-Asp(OBu-t)]-N'-ethoxycarbonyl Rhodamine 110 SEQ ID NO:5 (100 mg, 0.086 mmol) and 50% trifluoroacetic acid in methylene chloride (3 mL) (as described in Example 4) was obtained 85 mg (99%) of the title compound. $R_f$=0.5 (10 mL EtOAc with 5 drops CF$_3$CO$_2$H). $^1$H NMR (CD$_3$OD): δ8.02–6.63 (m, 15H), 5.08–5.04 (d, 2H), 4.48–3.92 (m, 6H), 3.10–1.95 (m, 8H), 1.31 (t, J=7.2 Hz, 3H), 1.05–0.96 (m, 9H).

EXAMPLE 30

N-[Ac-Asp(OBu-t)-Glu(OBu-t)-Val-Asp(OBu-t)]-N'-ethoxycarbonyl-Rhodamine 110 SEQ ID NO:5

From Ac-Asp(OBu-t)-Glu(OBu-t)-Val-Asp(OBu-t) SEQ ID NO:5 (307.6 mg, 0.45 mmol), EDC (86 mg, 0.45 mmol) and N-ethoxycarbonyl-Rhodamine 110 (60 mg, 0.15 mmol) (as described in Example 1) was obtained 128 mg (80%) of the title compound as a solid. $R_f$=0.35 (EtOAc/CH$_2$Cl$_2$=1:1). $^1$H NMR (CDCl$_3$): δ9.00 (d, J=7.5 Hz), 8.80–8.54 (m, 2H), 8.05–6.90 (m, 9H),6.72 (s, 1H), 6.69 (s, 1H), 4.93–4.02 (m, 6H), 3.09–2.30 (m, 6H), 2.10 (s, 3H), 2.05 (m, 2H), 1.48–1.30 (m, 29H), 1.06–0.96 (m, 6H).

EXAMPLE 31

N-(Ac-Asp-Glu-Val-Asp)-N'-ethoxycarbonyl-Rhodamine 110 SEQ ID NO:5

From N-[Ac-Asp(OBu-t)-Glu(OBu-t)-Val-Asp(OBu-t)]-N'-ethoxycarbonyl Rhodamine 110 SEQ ID NO:5 (90 mg, 0.084 mmol) and 50% trifluoroacetic acid in methylene chloride (2 mL) was obtained 65 mg (86%) of the title compound. $^1$H NMR (CD$_3$OD): δ8.12–7.26 (m, 9H), 7.21 (d, J=7.2 Hz, 1H), 7.08–7.05 (m, 1H), 6.79–6.64 (m, 2H), 4.67 (m, 1H), 4.40 (m, 1H), 4.20 (q, J=6.9 Hz, 2H), 4.07–3.52 (m, 2H), 3.07–2.68 (m, 4H), 2.38 (m, 2H), 2H), 1.98–1.94 (t, 3H), 1.32 (t, J=6.9 Hz, 3H), 1.04–0.95 (m, 6H).

EXAMPLE 32

N-Octyloxycarbonyl-Rhodamine 110

From Rhodamine 110 (500 mg, 1.36 mmol), N,N-diisopropylethylamine (351.6 mg, 2.76 mmol), and octyl chloroformate (316 mg, 1.64 mmol) (as described in Example 25) was obtained 182 mg (28%) of the title compound as colorless solid. $R_f$=0.7 (EtOAc/hexane=1:1). $^1$H NMR (CDCl$_3$): δ7.99 (d, J=7.2 Hz, 1H), 7.65–7.56 (m, 2H), 7.52 (bs, 1H), 7.15 (d, J=7.5 Hz, 1H), 6.88–6.32 (m, 6H), 4.17 (t, J=6.6 Hz, 2H), 3.9 (2H), 1.68 (m, 2H), 1.42–1.26 (m, 8H), 0.89 (t, J=6.3 Hz, 3H).

EXAMPLE 33

N-[Ac-Asp(OBu-t)-Glu(OBu-t)-Val-Asp(OBu-t)]-N'-Octyloxycarbonyl-Rhodamine 110 SEQ ID NO:5

From Ac-Asp(OBu-t)-Glu(OBu-t)-Val-Asp(OBu-t) SEQ ID NO:5 (123.7 mg, 0.18 mmol), EDC (34.5 mg, 0.18 mmol) and N-octyloxycarbonyl-Rhodamine 110 (29 mg, 0.06 mmol) (as described in Example 1) was obtained 43 mg (62%) of the title compound as a solid. $^1$H NMR (CDCl$_3$): δ9.01–8.53 (m, 3H), 8.07–7.99 (m, 1H), 7.77–6.78 (m, 9H), 6.72 (s, 1H), 6.69 (s, 1H), 4.93 (m, 1H), 4.76–4.64 (m, 1H), 4.39 (m, 1H), 4.16 (m, 2H), 4.06 (m, 1H), 3.08–2.02 (m, 9H), 2.10 (s, 3H), 1.47–1.29 (m, 39H), 1.05–0.96 (m, 6H), 0.88 (t, J=5.7 Hz, 3H).

EXAMPLE 34

N-(Ac-Asp-Glu-Val-Asp)-N'-octyloxycarbonyl-Rhodamine 110 SEQ ID NO:5

From N-[Z-Asp(OBu-t)-Glu(OBu-t)-Val-Asp(OBu-t)]-N'-octyloxycarbonyl R-110 SEQ ID NO:5 and 50% trifluoroacetic acid in methylene chloride (2 mL) was obtained 16.5 mg (100%) of the title compound. $R_f$=0.46 (10 mL EtOAc with 5 drops CF$_3$CO$_2$H). $^1$H NMR (CD$_3$OD): δ8.02–7.04 (m, 8H), 6.79–6.64 (m, 2H), 4.67(m, 1H), 4.40 (m, 1H), 4.15 (t, J=6.6 Hz, 2H), 4.15–3.94 (m, 2H), 3.10–2.10 (m, 6H), 2.01–1.94 (m, 3H), 1.69 (m, 2H),1.29 (bs, 10H), 1.05–0.86 (m, 9H).

EXAMPLE 35

N-Methoxycarbonyl-Rhodamine 110

From Rhodamine 110 (600 mg, 1.64 mmol), N,N-diisopropylethylamine (254 mg, 1.96 mmol) and methyl chloroformate (201 mg, 2.13 mmol) (as described in Example 25) was obtained 28 mg (4.4%) of the title compound as colorless solid. $R_f$=0.77 (EtOAc/Hexane=3:1). $^1$H NMR (CDCl$_3$): δ8.10–6.53 (m, 9H), 6.35 (d, J=7.2 Hz, 1H), 3.90 (bs, 2H), 3.80 (s, 3H).

EXAMPLE 36

N-Methylsulfonyl-Rhodamine 110

From Rhodamine 110 (500 mg, 1.36 mmol), N,N-diisopropylethylamine (211 mg, 1.64 mmol) and methylsulfonyl chloride (187 mg, 1.64 mmol) (as described in Example 25) was obtained 42.1 mg (9.4%) of the title compound. $^1$H NMR (CDCl$_3$): δ8.02 (d, J=7.5 Hz, 1H), 7.71–7.62 (m, 3H), 7.24–6.36 (m, 7H), 3.95 (bs, 2H), 3.18 (s, 3H).

EXAMPLE 37

N-Acetyl-Rhodamine 116

From Rhodamine 116 (458.8 mg, 1.0 mmol), N,N-diisopropylethylamine (129.3 mg, 1.0 mmol) and acetic anhydride (122 mg, 1.2 mmol) (as described in Example 25) was obtained 141 mg (9.4%) of the title compound as colorless solid. $R_f$=0.64 (EtOAc/CH$_2$Cl$_2$=2:1). $^1$H NMR (CDCl$_3$): δ8.01 (d, J=7.5 Hz, 1H), 7.69–7.62 (m, 3H), 7.24–6.36 (m, 7H), 3.95 (bs, 2H), 3.28 (s, 3H), 2.87 (s, 3H), 1.95 (bs, 3H).

EXAMPLE 38

N-Dimethylcarbamyl-Rhodamine 110

From Rhodamine 110 (1.0 g, 2.73mmol), N,N-diisopropylethylamine (0.42 g, 3.27 mmol) and dimethylcarbamyl chloride (0.35 g, 3.27 mmol) (as described in Example 25) was obtained 10 mg (1%) of the title compound as solid. $R_f$=0.3 (EtOAc). $^1$H NMR (CD$_3$OD): δ8.00 (d, J=7.2 Hz, 1H), 7.80–7.64 (m, 3H), 7.55 (d, J=2.1 Hz, 1H), 7.21–6.40 (m, 6H), 3.03 (s, 6H).

EXAMPLE 39

N-Hexyloxycarbonyl-Rhodamine-110

From Rhodamine-110, diisopropylethylamine (0.24 mL, 2.52 mmol) and hexyl chloroformate (0.27 mL, 1.64 mmol) (as described in Example 25) was obtained the title compound as an orange solid (80 mg, 13%). $^1$H NMR (CDCl$_3$): δ7.99 (d, J=6.6, 1H), 7.67–7.56 (m, 2H), 7.51 (s, 1H), 7.14 (d, J=7.5, 1H), 6.87 (dd, J=1.8, 8.7, 1H), 6.79 (s, 1H), 6.66 (d, J=8.7, 1H), 6.54–6.50 (m, 2H), 6.33 (dd, J=2.1, 8.7, 1H), 4.17 (t, J=6.6, 2H), 3.92 (s, 2H), 1.68 (m, 2H), 1.34 (br s, 6H), 0.91 (t, J=6.0, 3H).

EXAMPLE 40

N-Decyloxycarbonyl-Rhodamine-110

The title compound was prepared as described in Example 25. $^1$H NMR (CDCl$_3$): δ7.98 (d, J=7.2, 1H), 7.67–7.56 (m, 2H), 7.51 (s, 1H), 7.14 (d, J=7.5, 1H), 6.89–6.87 (m, 2H), 6.66 (d, J=8.4, 1H), 6.53–6.49 (m, 2H), 6.32 (d, J=8.4, 1H), 4.17 (t, J=6.6, 2H), 3.93(s, 2H), 1.67 (m, 2H), 1.27 (br s, 14H), 0.89 (t, J=6.9, 3H).

EXAMPLE 41

N-Dodecyloxycarbonyl-Rhodamine-110

The title compound was prepared as described in Example 25. $^1$H NMR (CDCl$_3$): δ8.00 (d, J=6.9, 1H), 7.68–7.57 (m, 2H), 7.51 (s, 1H), 7.16 (d, J=6.9, 1H), 6.86 (d, J=8.4, 1H), 6.89–6.53 (m, 4H), 6.35 (d, J=7.1, 1H), 4.17 (t, J=6.3, 2H), 3.89(s, 2H), 1.67 (m, 2H), 1.27 (br s, 18H), 0.89 (t, J=5.7, 3H).

EXAMPLE 42

N-[Ac-Asp(OBu-t)-Glu(OBu-t)-Val-Asp(OBu-t)]-N'-hexyloxycarbonyl-Rhodamine-110 SEQ ID NO:5

From Ac-Asp(OBu-t)-Glu(OBu-t)-Val-Asp(OBu-t)-OH SEQ ID NO:5 (263 mg, 0.383 mmol), EDC (74 mg, 0.39 mmol) and N-hexyloxycarbonyl-Rhodamine-110 (44 mg, 0.096 mmol) (according to Example 1) was obtained the title compound as a white solid (30 mg, 28%). $^1$H NMR (CDCl$_3$): δ8.99 (d, J=6.9, 1H), 8.78 (d, J=11.7, 1H), 8.52 (s, 1H), 8.06–6.69 (m, 13H), 4.97–4.01 (m, 6H), 3.08–2.04 (m, 12H), 1.70–1.34 (m, 39H), 1.04–0.89 (m, 9H).

EXAMPLE 43

N-[Ac-Asp(OBu-t)-Glu(OBu-t)-Val-Asp(OBu-t)]-N'-decyloxycarbonyl-Rhodamine-110 SEQ ID NO:5

The title compound was prepared as described in Example 1. $^1$H NMR (CDCl$_3$): δ9.01–8.76 (m, 3H), 8.51 (s, 1H), 8.02–6.69 (m, 13H), 4.97–4.01 (m, 6H), 3.08–2.04 (m, 12H), 1.70–1.34 (m, 47H), 1.04–0.88 (m, 9H).

EXAMPLE 44

N-[Ac-Asp(OBu-t)-Glu(OBu-t)-Val-Asp(OBu-t)]-N'-dodecyloxycarbonyl-Rhodamine-110 SEQ ID NO:5

The title compound was prepared as described in Example 1. $^1$H NMR (CDCl$_3$): δ9.01–8.76 (m, 3H), 8.51 (s, 1H), 8.02–6.69 (m, 13H), 4.97–4.01 (m, 6H), 3.08–2.04 (m, 12H), 1.70–1.34 (m, 51H), 1.04–0.88 (m, 9H).

EXAMPLE 45

N-(Ac-Asp-Glu-Val-Asp)-N'-hexyloxycarbonyl-Rhodamine-110 SEQ ID NO:5

From N-[Ac-Asp(OBu-t)-Glu(OBu-t)-Val-Asp(OBu-t)]-N'-hexyloxycarbonyl-Rhodamine-110 SEQ ID NO:5 (30 mg, 0.027 mmol) and trifluroacetic acid (2 mL) was obtained the title compound as a yellow solid (22 mg, 85%). $^1$H NMR (CD$_3$OD): δ8.13–7.32 (m, 8H), 7.26 (d, J=6.6, 1H), 7.12 (d, J=8.7, 1H), 6.83–6.69 (m, 2H), 4.72 (m, 1H), 4.44–3.99 (m, 5H), 3.11–2.77 (m, 3H), 2.43 (m, 2H), 2.17 (m, 2H), 2.03–1.98(m, 5H), 1.73 (m, 2H), 1.49–1.34 (m, 8H), 1.04–0.97 (m, 9H).

EXAMPLE 46

N-(Ac-Asp-Glu-Val-Asp)-N'-decyloxycarbonyl-Rhodamine-110 SEQ ID NO:5

The title compound was prepared as described in Example 45. $^1$H NMR (CD$_3$OD): δ8.13–7.32 (m, 8H), 7.26 (d, J=7.8, 1H), 7.12 (d, J=8.1, 1H), 6.83–6.69 (m, 2H), 4.72 (m, 1H), 4.44–3.99 (m, 5H), 3.11–2.77 (m, 3H), 2.45 (m, 2H), 2.22–2.10 (m, 2H), 2.05–1.98(m, 5H), 1.73 (m, 2H), 1.49–1.26 (m, 14H), 1.06–0.92 (m, 9H).

EXAMPLE 47

N-(Ac-Asp-Glu-Val-Asp)-N'-dodecyloxycarbonyl-Rhodamine-110 SEQ ID NO:5

The title compound was prepared as described in Example 45. $^1$H NMR (CD$_3$OD): δ8.07–7.08 (m, 10H), 6.81–6.68 (m, 2H), 4.73 (m, 1H), 4.44–3.35 (m, 5H), 3.26–2.02 (m, 12H), 1.73 (m, 2H), 1.49–1.29 (m, 18H), 1.06–0.92 (m, 9H).

EXAMPLE 48

N-(Ethylthio)carbonyl-Rhodamine 110

To the solution of Rhodamine 110 (500 mg, 1.36 mmol) dissolved in dimethylformamide (12 mL) at −61 °C. was added N,N-diisopropylethylamine (264 mg, 2.04 mmol), then ethyl chlorothiolformate (204 mg, 1.64 mmol) was added dropwise to the above solution. The reaction solution was then slowly warmed to room temperature and kept stirring for 1 h. It was then diluted with 100 mL of ice water and extracted with ethyl acetate (3×30 mL). The organic phase was washed with brine (2×50 mL) and it was dried over Na$_2$SO$_4$ and concentrated to give crude product which was purified by chromatography (Hexane/EtOAc 2:1), gave 238 mg (42%) of the title compound as a solid. R$_f$=0.6 (EtOAc/Hexane=1:1). $^1$HNMR (CDCl$_3$): δ8.01 (d, J=6.9 Hz, 1H), 7.68–7.57 (m, 3H), 7.21 (bs, 1H), 7.14 (d, J=7.2 Hz, 1H), 6.88 (dd, J$_1$=8.4 Hz, J$_2$=2.1 Hz, 1H), 6.68 (d, 1H), 6.56–6.50 (m, 2H), 6.34 (dd, J$_2$=8.4 Hz, J2=2.1 Hz, 1H), 3.91 (s, 2H), 3.00 (q, J=7.5 Hz, 2H), 1.36 (t, J=7.5 Hz, 3H).

EXAMPLE 49

N-[Ac-Asp(OBu-t)-Glu(OBu-t)-Val-Asp(OBu-t)]-N'-(ethylthio)carbonyl-Rhodamine 110 SEQ ID NO:5

The title compound was prepared as described in Example 1. R$_f$=0.56 (EtOAc/CH$_2$Cl$_2$=2:1); $^1$H NMR (CDCl$_3$): δ9.04–8.46 (m, 3H), 8.01–6.68 (m, 11H), 4.93–3.86 (m, 4H), 3.15–1.85 (m, 8H), 2.14 (d, 3H), 1.48–1.33 (m, 29H), 1.06–0.98 (m, 6H).

EXAMPLE 50

N-(Ac-Asp-Glu-Val-Asp)-N'-(ethylthio)carbonyl-Rhodamine 110 SEQ ID NO:5

The title compound was prepared as described in Example 45. $^1$H NMR (CD$_3$OD): δ8.12–7.09 (m, 11H), 6.79–6.66 (m, 2H), 4.67–3.93 (m, 4H), 3.08–2.68 (m, 6H), 2.38 (m, 2H), 2.12 (m, 2H), 1.99–1.94 (t, 3H), 1.32 (t, J=7.5 Hz, 3H), 1.04–0.94 (m, 6H).

EXAMPLE 51

2,5,8-Trioxadecylchloroformate

A solution of triethylene glycol monomethyl ether (2 g, 12.2 mmol) in ether (15 mL) was added dropwise to a stirred, ice-cold solution of 20% phosgene in toluene (11.36 mL, 21.92 mmol) over 20 min. The reaction mixture was allowed to warm to rt and stirring was continued for 15 h. Evaporation of the solvent give 2.63 g (95%) of the title compound. $^1$H NMR (CDCl$_3$): δ4.44 (m, 2H), 3.37 (m, 2H), 3.68–3.63 (m, 6H), 3.55 (m, 2H), 3.38 (s, 3H).

EXAMPLE 52

N-(2,5,8-Trioxadecyloxycarbonyl)-Rhodamine 110

From Rhodamine 110 (500 mg, 1.36 mmol), N,N-diisopropylethylamine (317 mg, 2.45 mmol) and 2,5,8-trioxadecyl chloroformate (371 mg, 1.64 mmol) was obtained 261 mg (37%) of the title compound as solid. R$_f$=0.52 (EtOAc/Hexane=4:1). $^1$H NMR (CDCl$_3$): δ8.00 (d, J=6.6 Hz, 1H), 7.66–7.58(m, 3H), 7.49 (s, 1H), 7.26 (bs, 1H), 6.88 (d, J=9.0 Hz, 1H), 6.65 (d, J=8.4 Hz, 1H), 6.54–6.31 (m, 3H), 4.33 (t, J=4.2 Hz, 2H), 3.93 (bs, 2H), 3.74 (t, J=3.3 Hz, 2H), 3.70–3.64 (m, 6H), 3.55 (m, 2H), 3.37 (bs, 3H).

EXAMPLE 53

N-[Ac-Leu-Glu(OBu-t)-Val-Asp(OBu-t)]-N'-ethoxycarbonyl-Rhodamine 110 SEQ ID NO:9

From Ac-Leu-Glu(OBu-t)-Val-Asp(OBu-t) (189 mg, 0.3 mmol) SEQ ID NO:9, EDC (57.5 mg, 0.3 mmol) and N-ethoxycarbonyl-Rhodamine 110 (40 mg, 0.1 mmol) (according to Example 1) was obtained 48 mg (47%) of the title compound as a solid. R$_f$=0.35 (EtOAc/CH$_2$Cl$_2$=1:1); $^1$H NMR (CD$_3$OD): δ8.02–7.04 (m, 8H), 6.79–6.93 (m, 2H), 4.35 (m, 2H), 4.20 (q, J=6.9 Hz, 2H), 4.11 (m, 1H), 3.94 (d, J=6.3 Hz), 3.00–2.65 (m, 2H), 2.30 (bs, 2H), 2.00 (m, 2H), 1.98–1.95 (d, 3H), 1.62–1.28 (m, 25H), 1.04–0.82 (m, 12H).

EXAMPLE 54

N-(Ac-Leu-Glu-Val-Asp)-N'-ethoxycarbonyl-Rhodamine 110 SEQ ID NO:9

The title compound was prepared as described in Example 45. $^1$H NMR (CD$_3$OD): δ8.40–7.05 (m, 9H), 6.79–6.63 (m, 2H), 4.37 (m, 1H), 4.31 (m, 1H), 4.20 (q, J=6.9 Hz, 2H), 4.11 (m, 1H), 3.94 (m, 1H), 3.07–2.68 (m, 2H), 2.38 (m, 2H), 2.08 (m, 2H), 1.99–1.95 (t, 3H), 1.68–1.48 (m, 3H), 1.31 (t, J=6.9 Hz, 3H), 1.04–0.80 (m, 12H).

EXAMPLE 55

N-[Cbz-Gly-Pro]-N'-ethoxycarbonyl-Rhodamine 110

From Cbz-Gly-Pro (91.8 mg, 0.3 mmol), EDC (57.5 mg, 0.3 mmol) and N-ethoxycarbonyl-Rhodamine 110 (40.2 mg, 0.1 mmol) (according to Example 1) was obtained 68 mg (98%) of the title compound as a solid. $R_f$=0.6 (EtOAc/CH2Cl2=4: 1). $^1$H NMR (CDCl$_3$): δ9.45 (s, 1H), 8.00 (d, J=7.2 Hz, 1H), 7.61–6.91(m, 8H), 6.68–6.63 (m, 2H), 5.69 (bs, 1H), 5.11 (s, 2H), 4.72 (d, 1H), 4.22 (q, J=6.9 Hz, 2H), 4.03 (bs, 2H), 3.58 (1H), 3.43 (m, 1H), 2.49–1.90 (m, 4H), 2.42 (bs, 1H), 2.18–1.95(m, 3H), 1.31 (t, J=6.9 Hz, 3H).

EXAMPLE 56

N-(Gly-Pro)-N'-ethoxycarbonyl-Rhodamine 110. HBr $^1$H NMR (CD$_3$OD): δ8.11 (d, J=7.8 Hz, 1H), 8.00 (bs, 1H), 7.84–7.72 (m, 3H), 7.32–7.15 (m, 3H), 6.95–6.87 (m, 2H), 4.64(m, 1H), 4.23 (q, J=6.9 Hz, 2H), 3.96 (s, 2H), 3.68 (m, 2H), 2.35–2.05 (m, 4H), 1.33 (t, J=6.9 Hz, 3H)

EXAMPLE 57

1-Hexyl Chlorothiolformate

A solution of 1-hexanethiol (3.72 g, 31.5 mmol) in ether (15 mL) was added dropwise to a stirred, ice-cold solution of 20% phosgene in toluene (25 mL, 47 mmol) over 20 min. The reaction mixture was allowed to warm to room temperature and stirring was continued for 15 h. Evaporation of the solvent give 6.1 g (98%). $^1$H NMR (CDCl$_3$): δ2.96 (t, J=7.2 Hz, 2H), 1.64–1.24 (m, 8H), 0.91 (t,J=6.3Hz, 3H).

EXAMPLE 58

N-(Hexylthio)carbonyl-Rhodamine 110

The title compound was prepared according to Example 25. $R_f$=0.8 (EtOAc/Hexane=1:1). $^1$H NMR (CDCl$_3$): δ8.00 (d, J=7.2 Hz, 1H), 7.65–7.58 (m, 3H), 7.24 (bs, 1H), 7.14 (d, 1H), 6.87 (dd, 1H), 6.68–6.32 (m, 4H), 3.92 (bs, 2H), 2.99 (t, J=6.9 Hz, 2H), 1.68 (m, 2H), 1.42 (m, 2H), 1.34–1.26 (m, 4H), 0.90 (t,J=7.2 Hz, 3H).

EXAMPLE 59

2-Butoxyethyl Chloroformate

From 2-butoxyethanol (3.72 g, 31.5 mmol) and 20% phosgene in toluene (25 mL, 47 mmol) was obtained 4.51 g (79%) of the title compound. $^1$H NMR (CDCl$_3$): δ4.46 (t, 2H), 3.70 (m, 2H), 3.51 (t, J=6.6 Hz, 2H), 1.56 (m, 2H), 1.40 (m, 2H), 0.94 (t, J=6.9 Hz, 3H).

EXAMPLE 60

N-(2-Butoxyethoxycarbonyl)-Rhodamine 110

The title compound was prepared according to Example 25. $R_f$=0.58 (EtOAc/Hexane=1:1). $^1$H NMR (CDCl$_3$): δ8.00 (d, J=7.5 Hz, 1H), 7.67–7.49 (m, 3H), 7.15 (d, J=7.8 Hz, 1H), 6.89–6.32 (m, 6H), 4.34 (m, 2H), 3.91 (bs, 2H), 3.68 (m, 2H), 3.50 (t, J=6.6 Hz), 1.59 (m, 2H), 1.39 (m, 2H), 0.93 (t, J=7.2 Hz, 3H).

EXAMPLE 61

N-[Cbz-Asp(OEt)-Glu(OEt)-Val-Asp(OEt)]-N'-Ethoxycarbonyl-Rhodamine 110 SEQ ID NO:5

From Cbz-Asp(OEt)-Glu(OEt)-Val-Asp(OEt) SEQ ID NO:5 (181 mg, 0.3 mmol), EDC (57.5 mg, 0.3 mmol) and N-ethoxycarbonyl-Rhodamine 110 (40 mg, 0.1 mmol) (according to Example 1) was obtained 71 mg (72%) of the title compound as a solid. $R_f$=0.3 (EtOAc/CH2Cl2=4:1), $^1$H NMR (CDCl$_3$): δ9.00 (bs, 1H), 8.76 (d, 1H), 8.43 (bs, 1H), 8.14–6.90 (m, 10H), 6.80–6.62 (m, 2H), 3.8 (m, 6H), 3.2–2.0 (m, 11H), 1.35–1.22 (m, 12H), 1.12–0.84 (m, 7H).

EXAMPLE 62

N-[Ac-Leu-Glu(OBu-t)-Val-Asp(OBu-t)]-N'-octyloxycarbonyl-Rhodamine 110 SEQ ID NO:9

The title compound was prepared according to Example 1. $R_f$=0.65 (EtOAc/CH$_2$Cl2=1:1), $^1$H NMR (CD$_3$OD): δ8.02–7.04 (m, 8H), 6.79–6.93 (m, 2H), 6.20 (bs, 1H), 4.95 (bs, 1H), 4.52–4.20 (m, SH), 3.15–2.00 (m, 9H), 1.68 (m, 2H), 1.48 (s, 9H), 1.45 (s, 9H), 1.41–1.29 (m, 12H), 1.18–0.88 (m, 15H).

EXAMPLE 63

N-(Z-Gly)-N'-ethoxycarbonyl-Rhodamine 110

From Z-Glycine (284 mg, 1.356 mmol), EDC (260 mg, 1.356 mmol). and N-ethoxycarbonyl Rhodamine 110 (58 mg, 0.135 mmol) (according to Example 1) was obtained the title compound (70 mg, 83%) as a solid. $^1$H NMR (CDCl$_3$): δ8.95 (bs, 1H), 7.98 (s, 2H), 7.53 (m, 8H), 7.30 (s, 5H), 7.05 (m, 2H), 6.63 (dd, 2H, J=8.4, 11.4 Hz), 5.09 (s, 2H), 4.19 (q, 2H, J=7.5 Hz), 1.27 (t, 3H, J=7.5 Hz).

EXAMPLE 64

N-Gly-N'-ethoxycarbonyl-Rhodamine 110 HBr

The title compound was prepared according to Example 6. $^1$H NMR (CDCl$_3$): δ9.41 (bs, 1H), 9.20 (s, 1H), 8.04 (m, 1H), 7.62 (m, 3H), 7.33 (m, 2H), 7.12 (m, 2H), 6.97 (m, 2H), 6.74 (m, 2H), 4.25 (q, 2H, J=6.9), 1.33 (t, 3H, J=6.9 Hz).

EXAMPLE 65

N-(Z-Gly-Pro-Gly)-N'-ethoxycarbonyl-Rhodamine 110

From Z-Glycine-Proline (315 mg, 1.03 mmol), EDC (197 mg, 1.03 mmol) and N-Gly-N'-ethoxycarbonyl-Rhodamine 110 (50 mg, 0.103 mmol) (according to Example 1) was obtained the title compound (70 mg, 96%) as a pale yellow color solid. $^1$H NMR (CDCl$_3$): δ8.97 (bs, 1H), 7.94 (d, 1H, J=7.8 Hz), 7.77 (d, 1H, J=15 Hz), 7.52 (m, 4H), 7.32 (s, 5H), 7.22 (m, 2H), 7.15 (m, 2H), 6.64 (m, 1H), 5.92 (bs, 2H), 5.78 (bs, 1H), 5.57 (bs, 1H), 5.09 (s, 2H), 4.95 (m, 2H), 4.74 (m, 2H), 4.16 (m, 2H), 3.62 (m, 1H), 3.46 (m, 1H), 1.98 (m, 4H), 1.26 (m, 3H).

EXAMPLE 66

N-(Gly-Pro-Gly)-N'-Ethoxycarbonyl-Rhodamine 110 HBr $^1$H NMR (CD$_3$OD): δ8.02 (d, 1H, J=7.8 Hz), 7.71 (m, 3H), 7.28 (m, 2H), 7.19 (m, 1H), 7.01 (m, 1H),6.71 (m, 2H), 4.48 (m, 1H), 4.19 (q, 2H, J=7.2 Hz), 4.05 (m, 2H), 3.94 (m, 2H), 3.61 (m, 2H), 2.12 (m, 4H), 1.30 (t, 3H, J=7.2 Hz).

EXAMPLE 67

N-Hexyl-N-methylcarbamyl Chloride

To a solution of 0.35 ml of (i-Pr)$_2$NEt in 10 ml of diethyl ether at 0° C. was added phosgene (1.06 ml, 1.93 M solution in toluene) and N-hexylmethylamine (0.31 ml, 2.05 mm). The reaction mixture was allowed to warm up to 25° C., and further stirred at 25° C. for 14 h. The mixture was filtered, and the solvent was removed under vacuum. The product was used for the next step reaction without further purification. $^1$H NMR (CDCl$_3$): δ3.42 (m, 2H), 3.07 (s, 3H), 1.59 (m, 2H), 1.31 (m, 6H), 0.90 (m, 3H).

EXAMPLE 68

N-(N-Hexyl-N-methylcarbamyl)-Rhodamine 110

To a solution of Rhodamine 110 (0.5 g, 1.36 mmol) in DMF (15 ml) at −61° C. was added N,N-diisopropylethylamine (0.25 ml) and N-hexyl-N-methylcarbamyl chloride in DMF (2.05 mmol). The reaction mixture was stirred at −61° C. for 1 h, then was allowed to warm up to rt. The reaction mixture was further stirred at rt for 14 h, and then was partitioned between aqueous saturated NH$_4$Cl solution and ethyl acetate (2×50 ml). The organic solution was washed with brine (100 ml), and dried over Na$_2$SO$_4$. The solvent was removed and the crude product was purified by flash chromatography (hexane : EtOAc, 1:1). The title compound (115 mg, 18%) was obtained as a solid. $^1$H NMR (CDCl$_3$): δ7.97 (d, 1H, J=7.2 Hz), 7.59 (m, 3H), 7.12 (d, 1H, J=7.5 Hz), 6.85 (dd, 1H, J=8.4, 2.1 Hz), 6.60 (dd, 2H, J=5.1, 3.3 Hz), 6.48 (dd, 2H, J=8.4, 2.1 Hz), 6.31 (dd, 1H, J=8.4, 2.4 Hz), 3.93 (bs, 2H), 3.33 (t, 2H, J=6.9 Hz), 2.79 (s, 3H), 1.56 (m, 2H), 1.30 (m, 6H), 0.88 (t, 3H, J=6.6 Hz).

EXAMPLE 69

N-(Octylthio)carbonyl Rhodamine 110

The title compound was prepared according to Example 25. $^1$H NMR (CDCl$_3$): δ7.99 (d, 1H, J=7.5 Hz), 7.59 (m, 3H), 7.11 (dd, 1H, J=6.9, 0.9 Hz), 6.89 (dd, 1H, J=8.4, 2.1 Hz), 6.64 (d, 1H, J=8.4 Hz), 6.48 (dd, 2H, J=8.4, 2.1 Hz), 6.31 (dd, 1H, J=8.4, 2.4 Hz), 3.97 (bs, 2H), 2.95 (m, 2H), 1.67 (m, 2H), 1.29 (m, 10H), 0.88 (t, 3H, J=6.6 Hz).

EXAMPLE 70

N-[Z-Gly]-N'-octyloxycarbonyl-Rhodamine-110

The title compound was prepared according to Example 1. $^1$H NMR (CDCl$_3$): δ8.22 (s, 1H), 7.11 (d, J=7.5, 1H), 7.04–6.97 (m, 2H), 6.85 (s, 1H), 6.70 (dd, J=7.5, 7.5, 2H), 5.57 (s, 1H), 5.16 (s, 1H), 5.16 (s, 2H), 4.18 (t, J=6.6, 2H), 4.01 (d, J=5.7, 1H), 1.68 (q, J=6.6, 2H), 1.29 (br s, 10H), 0.89 (t, J=6.9, 3H).

EXAMPLE 71

N-Gly-N'-octyloxycarbonyl-Rhodamine-110 HBr

The title compound was prepared according to Example 6. $^1$H NMR (CD$_3$OD): δ8.10 (d, J=6.9, 1H), 7.93 (d, J=2.4, 1H), 7.86–7.75 (m, 3H), 7.28–7.24 (m, 2H), 7.11 (dd, J=2.4, 9.0, 1H), 6.85 (d, J=9.0, 1H), 6.78 (d, J=9.0, 1H), 4.20 (t, J=6.6, 2H), 3.94 (s, 2H), 1.74 (m, 2H), 1.50–1.30 (br m 10H), 0.94 (t,J=6.6,3H).

EXAMPLE 72

Fluorescence and Stability of N-Acetyl-Rhodamine 110 Compared to Rhodamine 110

The activities of Rhodamine 110 and N-acetyl-Rhodamine 110 as fluorescent moieties for synthetic substrates were measured in a fluorometric assay. The fluorescent signal is read in a spectrofluorometer or in a fluorometric microtiter plate reader at excitation wavelength of 485 and emission 530. Using this assay, the relative fluorescent values were determined for the two fluorescent moieties.

Fluorescence was measured using the following buffer conditions: 100 mM HEPES pH 7.5, with 10% sucrose, 1% CHAPS, 5 mM glutathione, and 1–200 nM test compound. The assay for stability was typically carried out at 37° C. for 2 days.

The ratio of fluorescent signal was 10.2 (Rhodamine 110/N-acetyl Rhodamine 110) at time zero and 10.1 after two days incubation at 37° C. The results show that similar to Rhodamine 110, N-acetyl-Rhodamine 110 is a stable and efficient fluorescent indicator.

EXAMPLE 73

Fluorescence of Modified Rhodamine Dye

Modified Rhodamine dyes were evaluated using both conventional spectrometry and spectrofluorometry. For both types of analysis the dyes were dissolved in either methanol or 50 mM Tris at final dye concentrations ranging from 10 nM to 100 μM. An absorbance spectrum from wavelengths of 200 nm to 700 nm was determined for each dye using a Beckman DU-7000 spectrophotometer. The dyes all had absorbance peaks at around 470 to 480 nm. This wavelength was chosen as the fluorescence excitation wavelength and a full fluorescence emission spectrum was determined using a Hitachi F-2000 spectrofluorometer. For each dye, the emission peak was around 520 nm and the fluorescent output was measured under the conditions tested (see Table 1).

TABLE 3

Fluorescence of Modified Rhodamine Dyes

| Compound | Test Conc. (μM) | Solvent | Peak Excitation Wavelength | Peak Emission Wavelength | Signal Amplitude |
|---|---|---|---|---|---|
| N-Octyl-oxycarbonyl-Rhodamine 110 | 1 | MeOH | 470 | 520 | 850 |
| N-Methoxy-carbonyl-Rhodamine 110 | 0.1 | Tris | 470 | 520 | 254 |
| N-Ethoxy-carbonyl-Rhodamine 110 | 1 | Tris | 485 | 520 | 3070 |
| Rhodamine 110 | 0.01 | Tris | 490 | 520 | 284 |
| N-Decyloxy-carbonyl-Rhodamine 110 | 1 | MeOH | 475 | 520 | 827 |
| N-Dodecyloxy-carbonly-Rhodamine 110 | 1 | MeOH | 480 | 520 | 640 |
| N-Hexyloxy-carbonyl-Rhodamine 110 | 0.1 | MeOH | 465 | 520 | 109 |

TABLE 3-continued

Fluorescence of Modified Rhodamine Dyes

| Compound | Test Conc. ($\mu$M) | Solvent | Peak Excitation Wavelength | Peak Emission Wavelength | Signal Amplitude |
|---|---|---|---|---|---|
| N-(Ethylthio) carbon-Rhodamine 110 | 1 | Tris | 490 | 520 | 2430 |
| N-(Hexylthio) carbonyl-Rhodamine 110 | 1 | MeOH | 490 | 530 | 650 |
| N-(Octylthio) carbonyl-Rhodamine 110 | 1 | MeOH | 470 | 520 | 471 |
| N-(2-Butoxy-ethoxy) carbonyl-Rhodamine 110 | 1 | Tris | 470 | 520 | 2047 |
| N-(2,5,8-trioxadecyloxy) carbonyl-Rhodamine 110 | 1 | Tris | 485 | 520 | 2841 |
| N-Acetyl-Rhodamine 116 | 1 | Tris | 470 | 530 | 644 |
| N-Methyl sulfonyl-Rhodamine 110 | 1 | Tris | 485 | 520 | 988 |
| N-Dimethyl-carbamyl-Rhodamine 110 | 0.1 | Tris | 490 | 520 | 446 |
| N-(N-Hexyl-N-methyl-carbamyl)-Rhodamine 110 | 1 | Tris | 470 | 520 | 1466 |

EXAMPLE 74

Uptake and Retention of Modified Rhodamine Dyes by HL-60 Cells

HL-60 cells were placed in 5 ml of Iscove's medium (without serum or phenol-red) containing 10 $\mu$M or 50 $\mu$M N-octyloxycarbonyl-Rhodamine 110, N-decyloxycarbonyl-Rhodamine-110, N-dodecyloxycarbonyl-Rhodamine-110, N-hexyloxycarbonyl-Rhodamine-110, N-(ethylthio)carbonyl-Rhodamine 110 or Rhodamine 110. The cells were incubated for varying times at 37° C. in a $CO_2$ incubator, recovered by centrifugation, and washed in 50 mL of ice-cold medium. The cells were re-centrifuged and the final pellet was resuspended in 50 $\mu$L of fresh medium. Aliquots of each cell suspension were placed in microslides and viewed on a Nikon inverted microscope with epifluorescent illumination. As shown in FIGS. 1A–1F, N-octyloxycarbonyl-Rhodamine 110 (FIG. 1A), N-decyloxycarbonyl-Rhodamine 110 (FIG. 1B), and N-dodecyloxycarbonyl-Rhodamine 110 (FIG. 1C) stained HL-60 cells intensely and there was almost no leakage of the dye into the medium. N-Hexyloxycarbonyl-Rhodamine 110 (FIG. 1D) stained HL-60 cells less intensely, but it was still well-retained. N-(Ethylthio)carbonyl-Rhodamine 110 (FIG. 1E) gave moderate, but still easily detectable staining, although there was slight leakage. Rhodamine 110 (FIG. 1F) stained cells rapidly, but the dye quickly leaked out of the cells, resulting in a low intensity of cellular staining and a high degree of fluorescence in the medium containing the cells. Therefore, the modified Rhodamine dyes are superior to Rhodamine 110 since they are readily taken up by HL-60 cells and are retained within the cells for at least 30 minutes.

EXAMPLE 75

Enzymetic Activity of the Substrates

The activities of N-(Z-VD)-N'-acetyl-Rhodamine 110, N-(Z-VAD)-N'-acetyl-Rhodamine 110, N-(Z-DEVD)-N'-acetyl-Rhodamine 110 SEQ ID NO:5, N-(Z-YVAD)-N'-acetyl-Rhodamine 110 SEQ ID NO:2, (Z-VAD)$_2$-Rhodamine 110 and (Z-YVAD)$_2$-Rhodamine 110 SEQ ID NO:2 as synthetic substrates for recombinant CPP32 and ICE were measured in a fluorometric enzyme assay. Recombinant CPP32 protein and ICE protein were prepared by expressing DNA clones encoding these enzymes in an insect host cell (sf9 cells) using baculovirus as the vector. See, Webb, N. R. et al., "Expression of proteins using recombinant Baculovirus," *Techniques* 2:173–188 (1990). Cleavage of the synthetic substrates by the enzyme results in a fluorescent signal which is read in a spectrofluorometer or in a fluorometric microtiter plate reader. Using this assay, the $K_m$ and $V_{max}$ values were determined for each substrate with either CPP32 or ICE.

CPP32 and ICE dependent substrate cleavage was measured using the following buffer conditions: 100 mM HEPES pH 7.5, with 10% sucrose, 1% CHAPS, 5 mM glutathione, and 1–100 $\mu$M test substrate. Nonspecific enzyme cleavage was determined with the use of the specific CPP32 and ICE inhibitors consisted of an oligomer with the sequence Asp-Glu-Val-Asp or Tyr-Val-Ala-Asp, respectively, with an aldehyde group conjugated to the C-terminus. The assay for enzyme activity was typically carried out at 37° C. for 60 minutes.

Table 4 lists the $K_m$ and $V_{max}$ values for N-(Z-VD)-N'-acetyl-Rhodamine 110, N-(Z-VAD)-N'-acetyl-Rhodamine 110, N-(Z-DEVD)-N'-acetyl-Rhodamine 110 SEQ ID NO:5, N-(Z-YVAD)-N'-acetyl-Rhodamine 110 SEQ ID NO:2, (Z-VAD)$_2$-Rhodamine 110 and (Z-YVAD)$_2$-Rhodamine 110 SEQ ID NO:2 as substrates for CPP32 and ICE.

TABLE 4

Cleavage of Substrate by CPP32 and ICE

| | Enzyme | | | |
|---|---|---|---|---|
| | CPP32 | | ICE | |
| | $K_m$ ($\mu$M) | $V_{max}$ (nmol/min) | $K_m$ ($\mu$M) | $V_{max}$ (nmol/min) |
| N-(Z-VD)-N'-Ac-Rhodamine 110 | 60 | 11 | NA | |
| N-(Z-VAD)-N'-Ac-Rhodamine 110 | NA | | 70 | 4 |
| N-(Z-DEVD)-N'-Ac-Rhodamine 110 SEQ ID NO: 5 | 154 | 160 | 12 | 9 |
| N-(Z-YVAD)-N'-Ac-Rhodamine 110 SEQ ID NO: 2 | NA | | 32 | 96 |
| (Z-VAD)$_2$-Rhodamine 110 | NA | | 21 | 9 |
| (Z-YVAD)$_2$-Rhodamine 110 SEQ ID NO: 2 | NA | | 6 | 14 |

NA = no activity observed at 1–100 $\mu$M substrate, 37° C., 3 h incubation

The results shown in Table 4 show that N-(Z-DEVD)-N'-acetyl-Rhodamine 110 SEQ ID NO:5 is an efficient substrate for both ICE and CPP32. Also shown is that N-(Z-VD)-N'-acetyl-Rhodamine 110 is an efficient substrate for CPP32 and not for ICE and that N-(Z-VAD)-N'-acetyl-Rhodamine 110, N-(Z-YVAD)-N'-acetyl-Rhodamine 110 SEQ ID NO:2, (Z-VAD)$_2$-Rhodamine 110 and (Z-YVAD)$_2$-Rhodamine 110 SEQ ID NO:2 are efficient substrates for ICE and not for CPP32.

EXAMPLE 76

Cleavage of Caspase-3 Substrates by Recombinant Human Caspase-3 and by Apoptotic HL-60 Cell Lysates The caspase substrates were assayed by recombinant caspase-3 and by lysates prepared from apoptotic HL-60 cells. The assays were carried out at 37° C. in 96-well plates in a 100 µL incubation containing 30 µL of caspase-3 preparation or cell lysate, 10 µM or 50 µM of the substrate, and caspase assay buffer (40 mM 1,4-piperazinebis (ethansulfonic acid) (PIPES, Aldrich Chemical Company) pH 7.2; 100 mM NaCl; 10% sucrose; 0.1% CHAPS; 1 mM EDTA; 10 mM DTT). At the end of the incubation period, the fluorescence was measured on a Bio-Tek FL500 fluorescence microplate reader using excitation and emission wavelengths of 485 and 530 nm, respectively. Two different controls were run: 1) an enzyme blank consisting of samples containing substrate, but without enzyme or cell lysate; 2) an inhibitor control, consisting of samples which contained the caspase inhibitor, Ac-DEVD-CHO (f.c., 10 µM). Table 5 is a summary of the results obtained with these substrates.

TABLE 5

Cleavage of Substrate by Caspase-3 and Lysates

| Compound | Cleavage by Caspase-3 | Cleavage by Apoptotic Lysates |
|---|---|---|
| N-Z-VD-N'-ethoxycarbonyl-R110 | Poor | Poor |
| N-Z-DEVD-N'-ethoxycarbonyl-R110 SEQ ID NO: 5 | Good | Good |
| N-Z-EVD-N'-ethoxycarbonyl-R110 | Fair | Fair |
| N-Ac-DEVD-N'-ethoxycarbonyl-R110 SEQ ID NO: 5 | Good | Good |
| N-Ac-DEVD-N'-octyloxycarbonyl-R110 SEQ ID NO: 5 | Good | Good |
| N-Ac-DEVD-N'-hexyloxycarbonyl-R110 SEQ ID NO: 5 | Good | Good |
| N-Ac-DEVD-N'-(ethylthio)carbonyl-R110 SEQ ID NO: 5 | Good | Good |

Figure 2A:
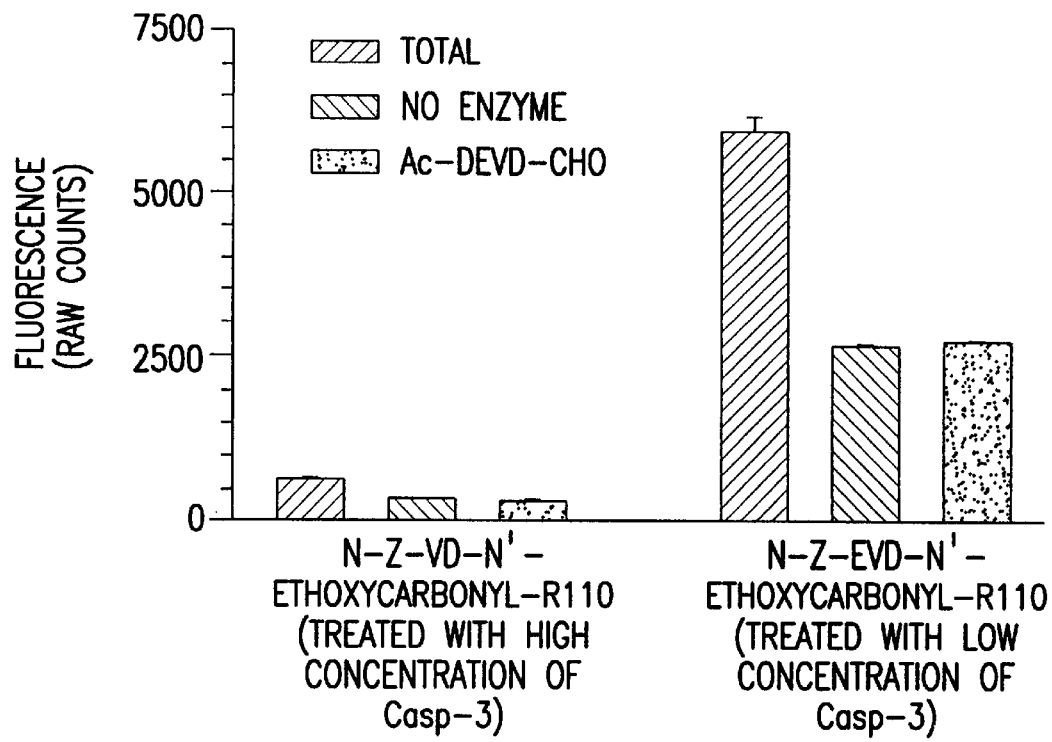
FIGS. 2A–2L depict the bar graphs of cleavage of the caspase substrates N-Z-VD-N'-ethoxycarbonyl-R110, N-Z-EVD-N'-ethoxycarbonyl-R110, N-Z-DEVD-N'-ethoxycarbonyl-R110 SEQ ID NO:5, N-Ac-DEVD-N'-ethoxycarbonyl-R110 SEQ ID NO:5, N-Ac-DEVD-N'-octyloxycarbonyl-R110 SEQ ID NO:5, N-Ac-DEVD-N'-hexyloxycarbonyl-R110 SEQ ID NO:5, and N-Z-DEVD-N'-(ethylthio)carbonyl-R110 SEQ ID NO:5, by r-caspase-3 (FIGS. 2A, 2B, 2D, 2G and 2J) and Vinblastine treated HL-60 cell lysates (FIGS. 2C, 2E, 2H and 2K) compared to HL-60 control (DMSO treated) lysates (FIGS. 2F, 2I and 2L).
Figure 2B:
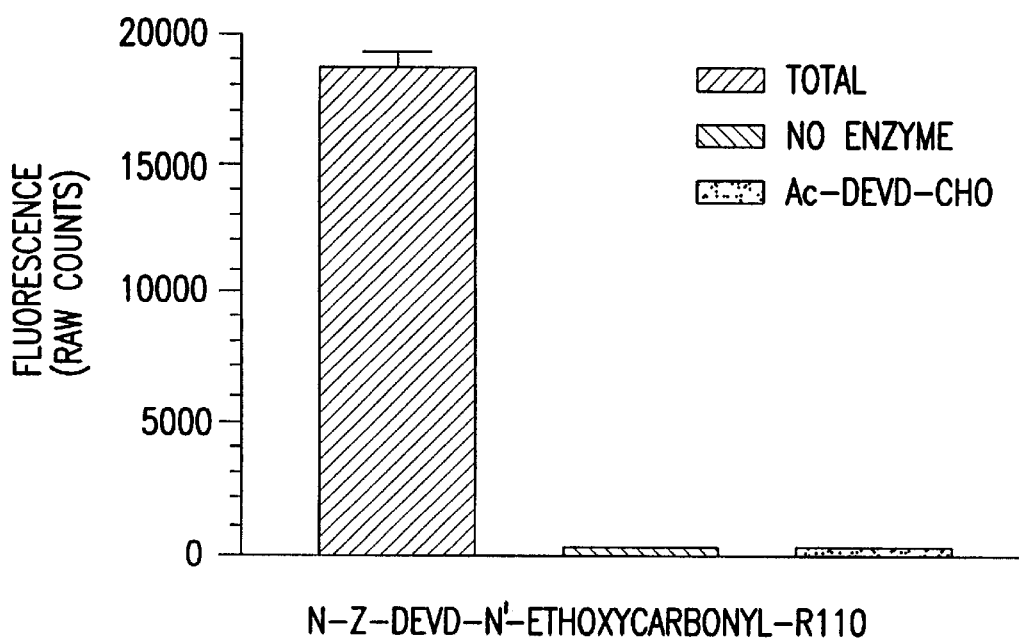
Figure 2C:
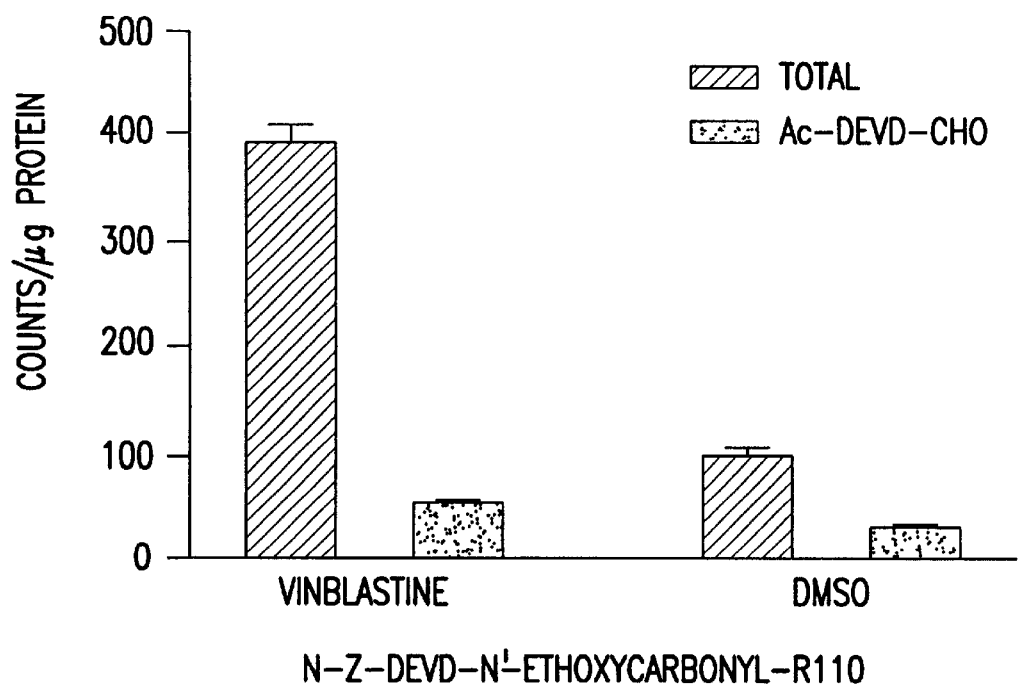
Figure 2D:
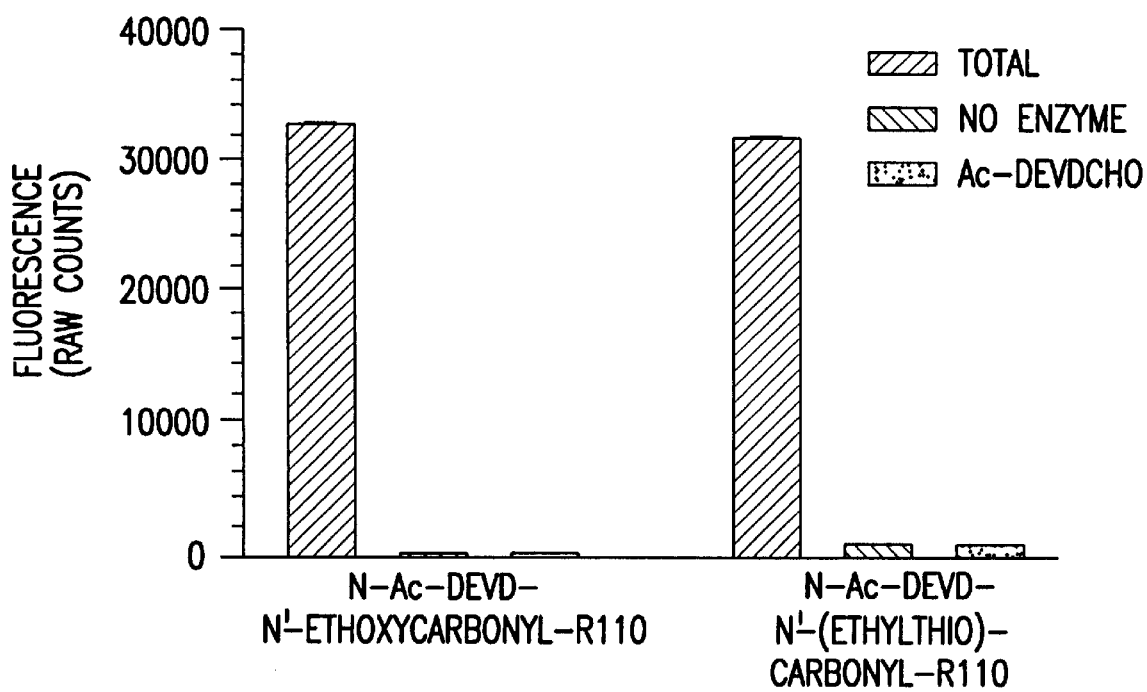
Figure 2E:
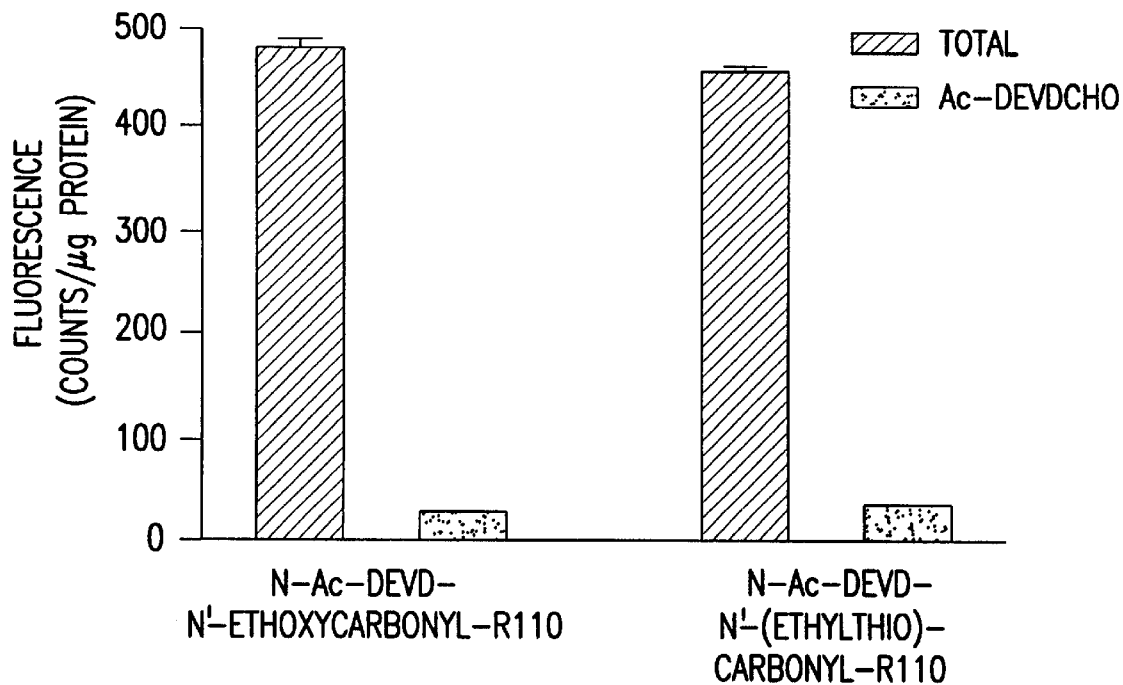
Figure 2F:
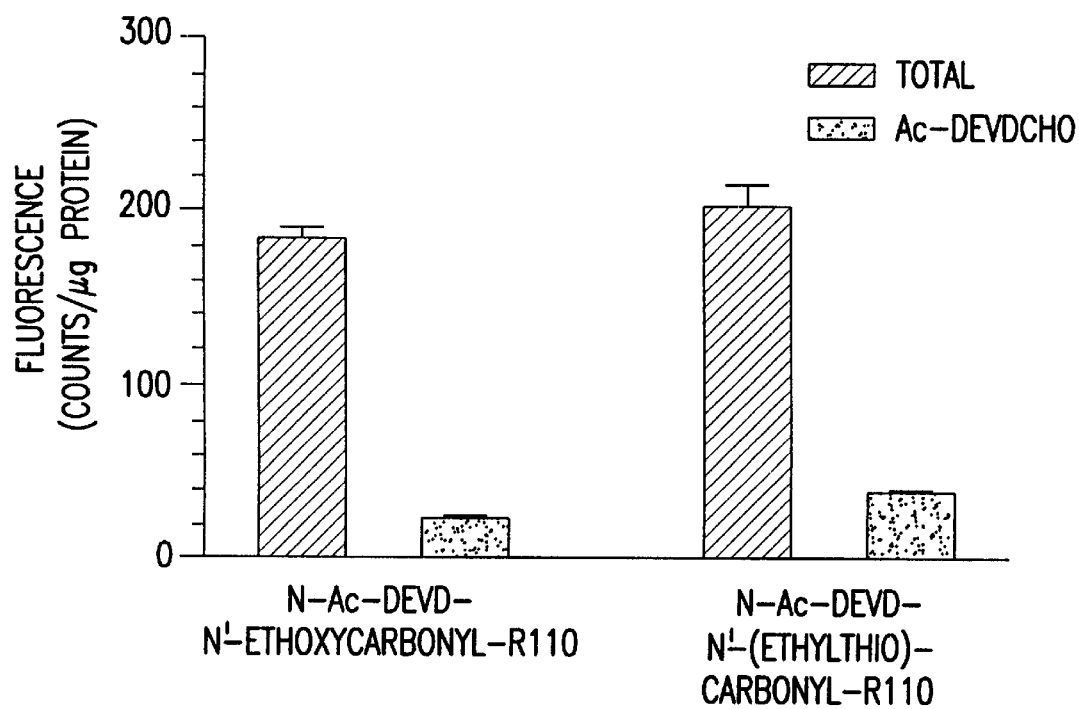
Figure 2G:
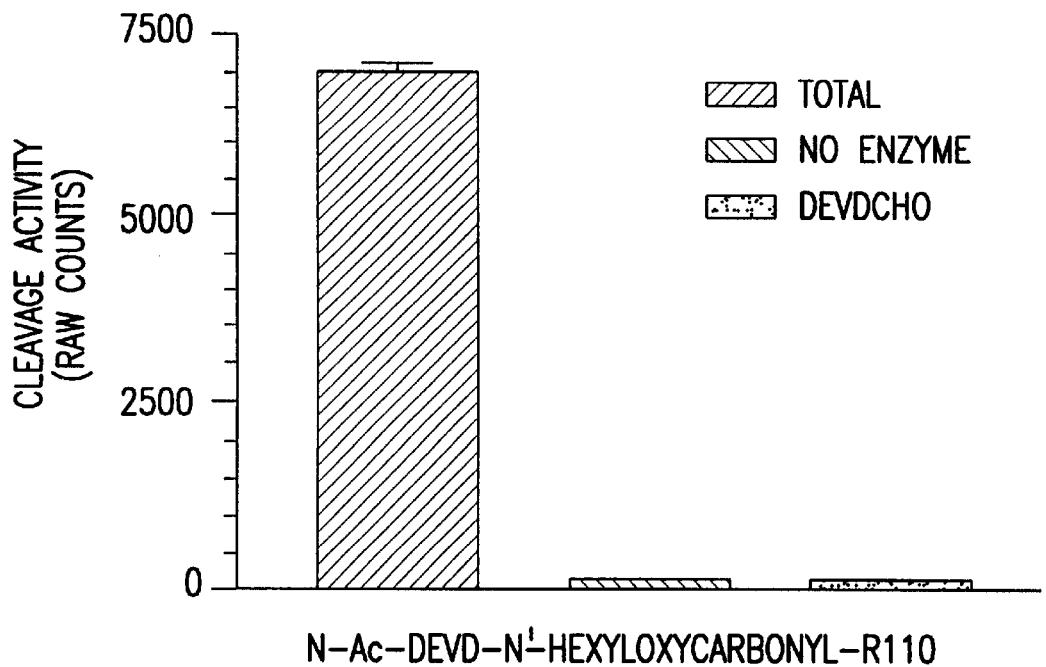
Figure 2H:
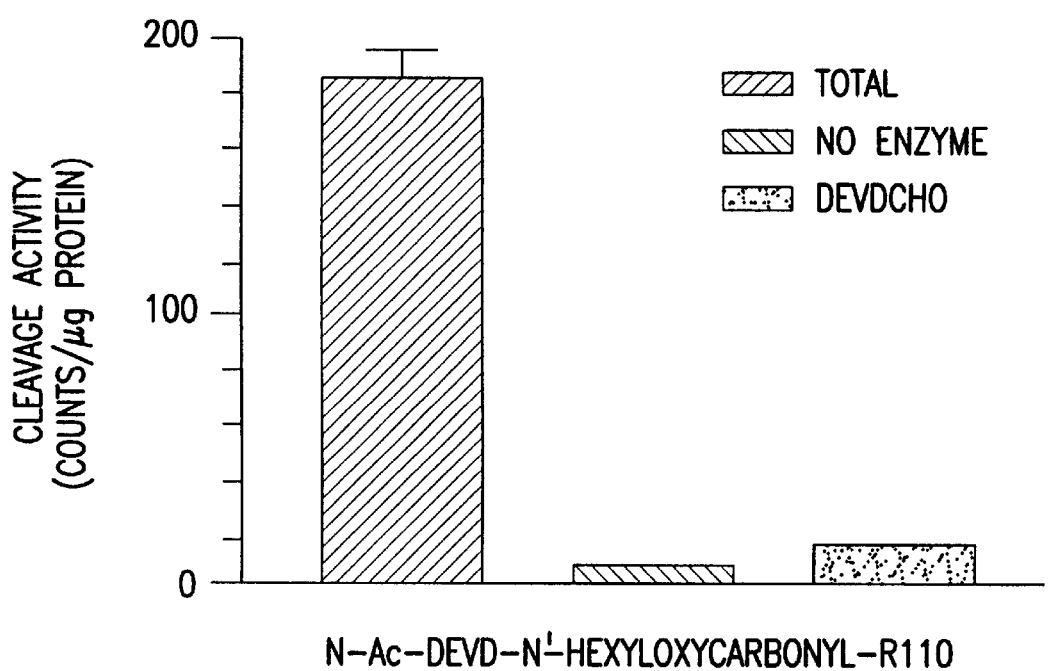
Figure 2I:
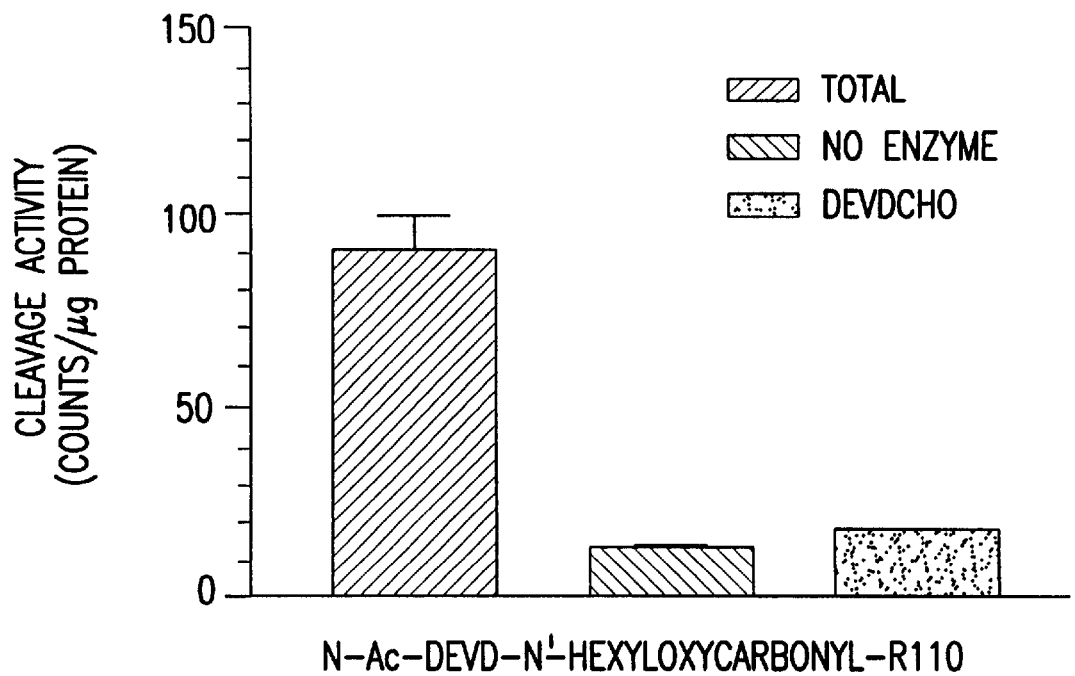
Figure 2J:
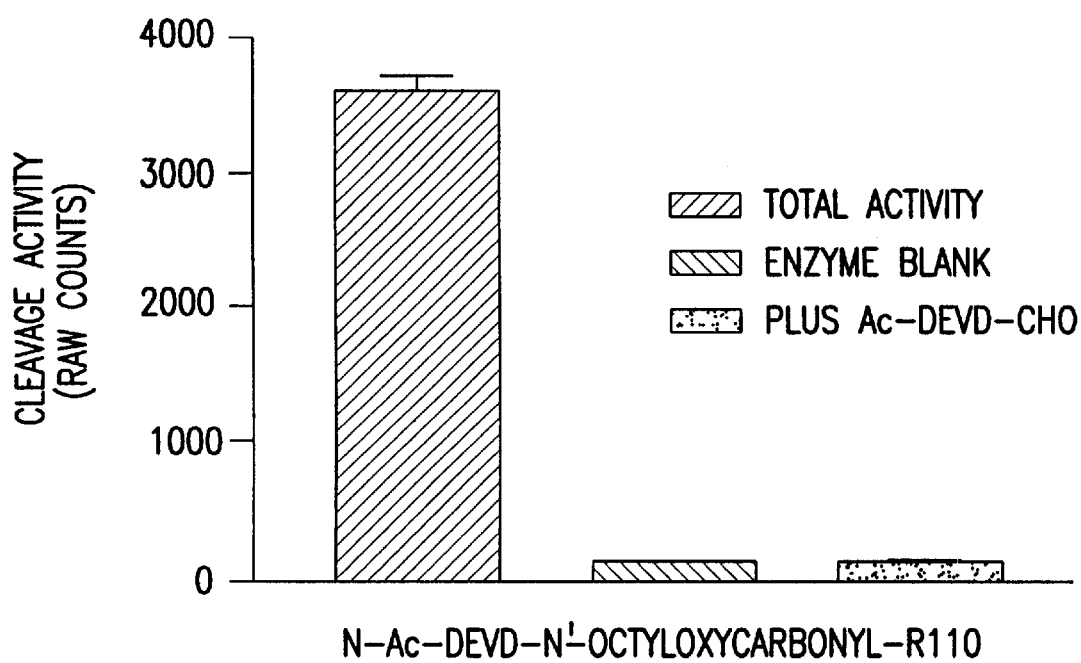
Figure 2K:
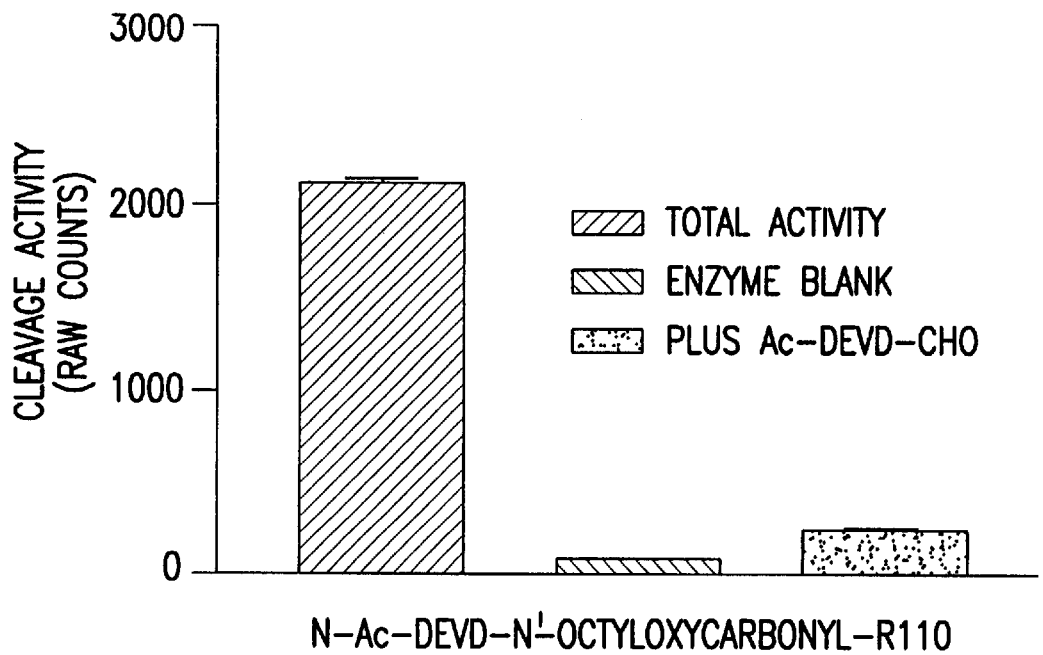
Figure 2L:
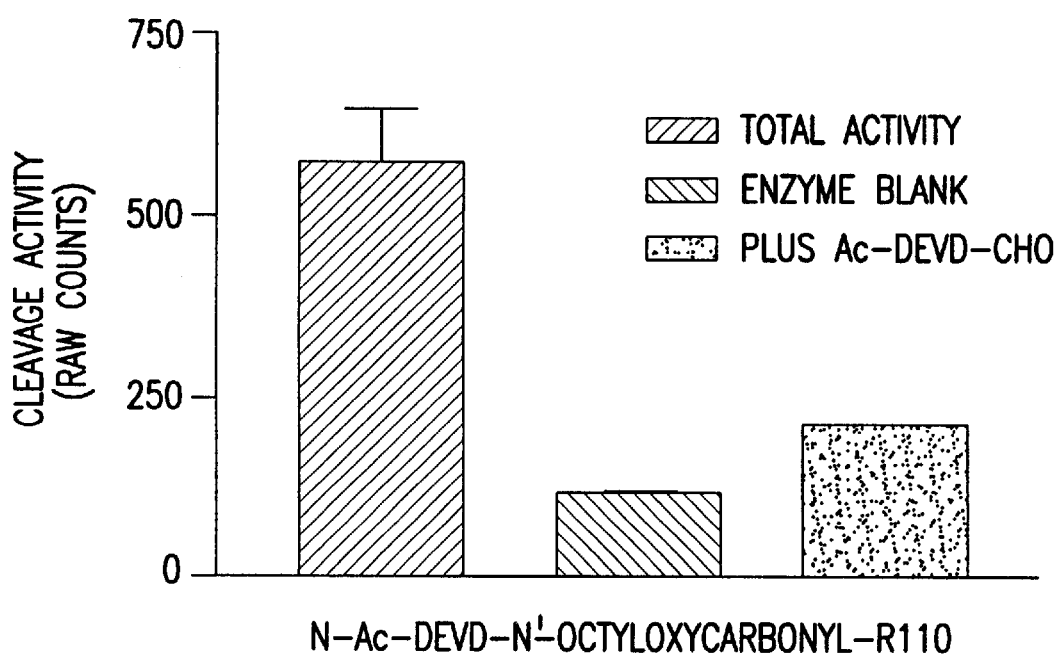

As shown in FIG. 2A, cleavage of the dipeptide substrate, N-Z-VD-N'-ethoxycarbonyl-R110, required extremely high concentrations of recombinant caspase-3 (a 50-fold greater amount of enzyme than needed for tri- and tetrapeptide substrates). Even with this large amount of enzyme, the signal was low. By contrast, the tripeptide substrate, N-Z-EVD-N'-Ethoxycarbonyl-R110 (FIG. 2A), and all of the tetrapeptide substrates (FIGS. 2B–2L) were cleaved efficiently by caspase-3 and apoptotic lysates.

EXAMPLE 77

Staining of Apoptotic HL-60 Cells by the Caspase-3 Substrate, N-Ac-DEVD-N'-octyloxycarbonyl R110

Figure 3A:
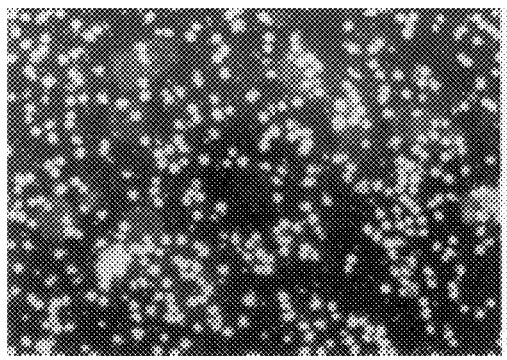
FIGS. 3A–3E depict photographs of cells stained by incubation with N-Ac-DEVD-N'-octyloxycarbonyl-R110 SEQ ID NO:5. Vinblastine (FIG. 3A) and DMSO (FIG. 3B) treated HL-60 cells, vinblastine treated HL-60 cells with N-Ac-DEVD-CHO SEQ ID NO:5 added in the assay stage (FIG. 3C), antiFas (FIG. 3D) and PBS (FIG. 3E) treated Jurkat cells.
Figure 3B:
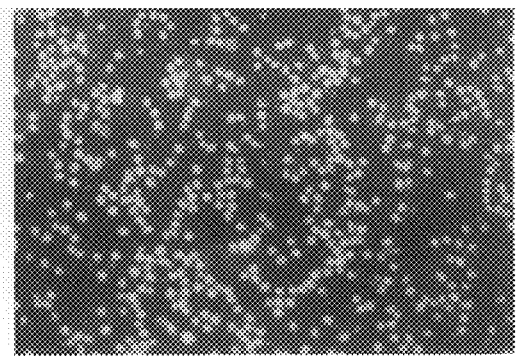
Figure 3C:
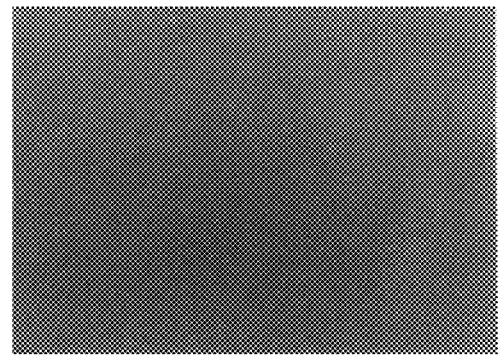
Figure 3D:
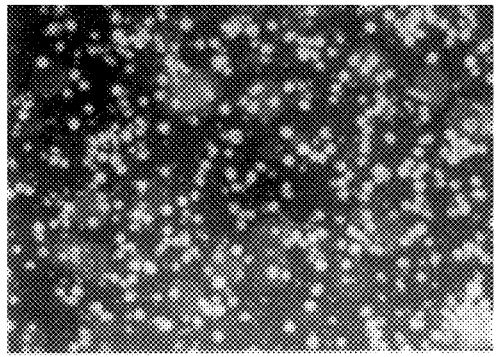
Figure 3E:
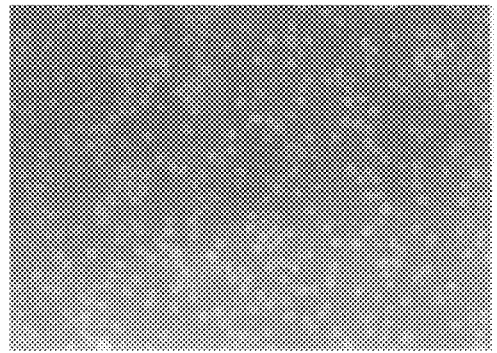

The ability of N-Ac-DEVD-N'-octyloxycarbonyl-R110 SEQ ID NO:5 to detect caspase activation in intact cells was tested using apoptotic HL-60 and Jurkat cells. These whole-cell assays were carried out in two stages: 1) induction of apoptosis; 2) incubation with the substrate. For HL-60 cells, apoptosis was induced by treatment with 10 µg/ml vinblastine for 4 hours. Control samples were treated with DMSO. For Jurkat cells, apoptosis was induced by treatment with 500 ng/ml agonistic antiFas antibody for 2 hours. Control samples were treated with PBS. Following apoptosis induction, the cells were incubated with 50 µM N-Ac-DEVD-N'-octyloxycarbonyl-R110 SEQ ID NO:5 in caspase assay buffer (40 mM PIPES, pH 7.4; 100 mM NaCl; 10% sucrose; 1 mM EDTA; 10 mM DTT). The cells were than transferred to a glass microslide and viewed by epifluorescent illumination on a Nikon inverted microscope. As show in FIG. 3A, vinblastine-treated HL-60 cells were intensely stained by N-Ac-DEVD-N'-octyloxycarbonyl R110 SEQ ID NO:5. DMSO-treated cells also showed some staining (FIG. 3B), although the intensity of the signal was significantly less than that of vinblastine-treated cells. HL-60 cells treated with 50 µM Ac-DEVD-CHO SEQ ID NO:5 during the assay stage (FIG. 3C) showed almost no fluorescent signal, indicating that the staining observed in vinblastine-treated cells is almost entirely due to caspase-mediated cleavage. Jurkat cells induced to undergo apoptosis by antiFas (FIG. 3D) also showed intense staining by N-Ac-DEVD-N'-octyloxycarbonyl R110 SEQ ID NO:5, while control cells showed only light staining (FIG. 3F). These experiments demonstrate that N-Ac-DEVD-N'-octyloxycarbonyl R110 SEQ ID NO:5 can be used to measure apoptosis in intact cells and that the signal obtained from N-Ac-DEVD-N'-octyloxycarbonyl-R110 SEQ ID NO:5 is caspase-dependent.

EXAMPLE 78

Figure 4:
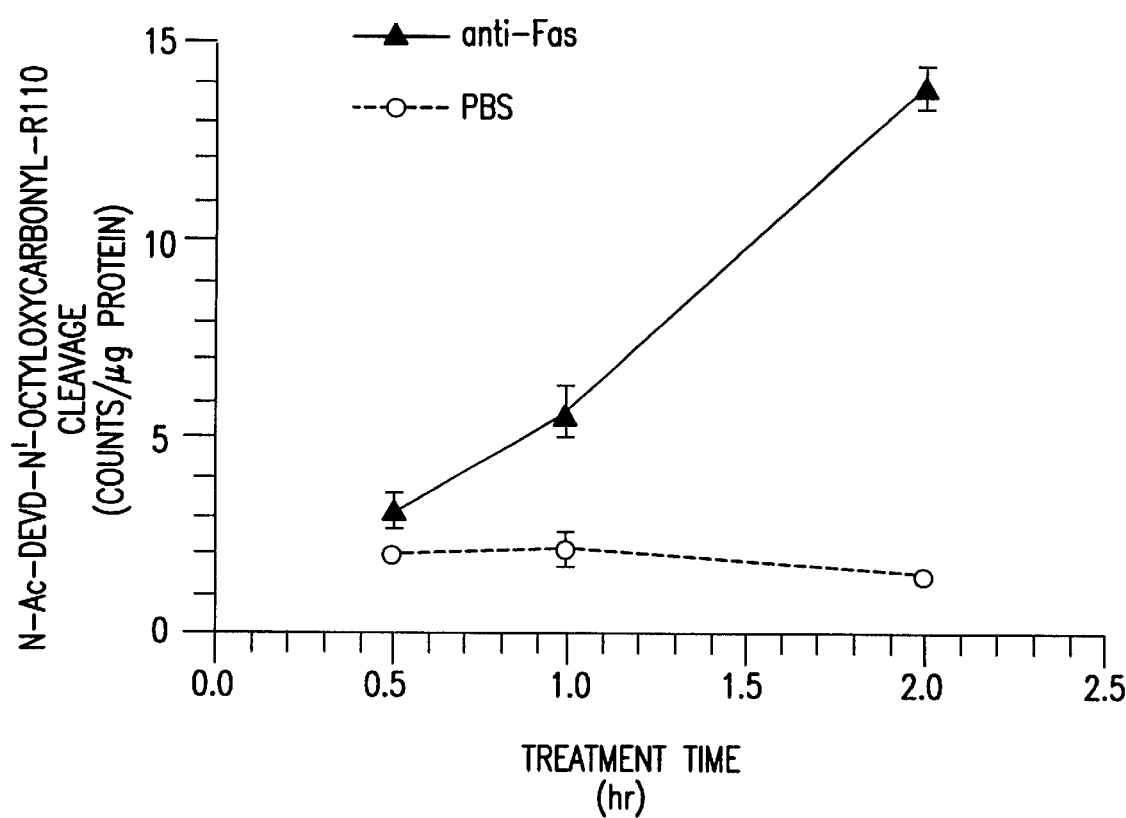
FIG. 4 depicts a graph showing the results of a cleavage assay of N-Ac-DEVD-N'-octyloxycarbonyl-R110 SEQ ID NO:5 by antiFas and PBS treated Jurkat cells.

Cleavage of the Caspase-3 Substrate, N-Ac-DEVD-N'-octyloxycarbonyl R110 SEQ ID NO:5, by Whole Apoptotic Jurkat Cells In order to quantitate the cleavage of N-Ac-DEVD-N'-octyloxycarbonyl-R110 SEQ ID NO:5 by whole cells, an assay was performed in which the fluorescent signal generated from this substrate by apoptotic Jurkat cells was measured in a spectrofluorometric plate reader. Jurkat cells were incubated for varying times in 96-well plates with 500 ng/ml antiFas antibody to induce apoptosis. Control cells were incubated with PBS. At the end of the treatment period, the cells were harvested, centrifuged in 1.5 ml tubes and resuspended in 25 µL of medium containing 1% FBS. 25 µL of caspase buffer containing 50 µM N-Ac-DEVD-N'-octyloxycarbonyl R110 SEQ ID NO:5 was added, and the cells were incubated for one hour. At the end of the incubation period, three 5 µL aliquots from each time point were placed in 96-well plates and the fluorescence was measured at excitation/emission wavelength of 485/530 nm. FIG. 4 shows that cells treated with PBS gave a small fluorescent signal which did not increase over the treatment times used. However, cells treated with antiFas gave a detectable fluorescent signal at about one hour after apoptosis induction, and the signal continued to increase up to the 2 hour timepoint, with a signal to background ratio of about 7. This experiment demonstrates that N-Ac-DEVD-N'-octyloxycarbonyl R110 SEQ ID NO:5 yields a robust signal in whole apoptotic cells and can therefore be used to quantitatively measure caspase-mediated apoptosis in a cell-based assay.

EXAMPLE 79

Cleavage of the Caspase-8 Substrate N-Ac-LEVD-N'-ethoxycarbonyl R110 SEQ ID NO: 9 by Recombinant Human Caspase-3, 6, 7, and 8

Figure 5:
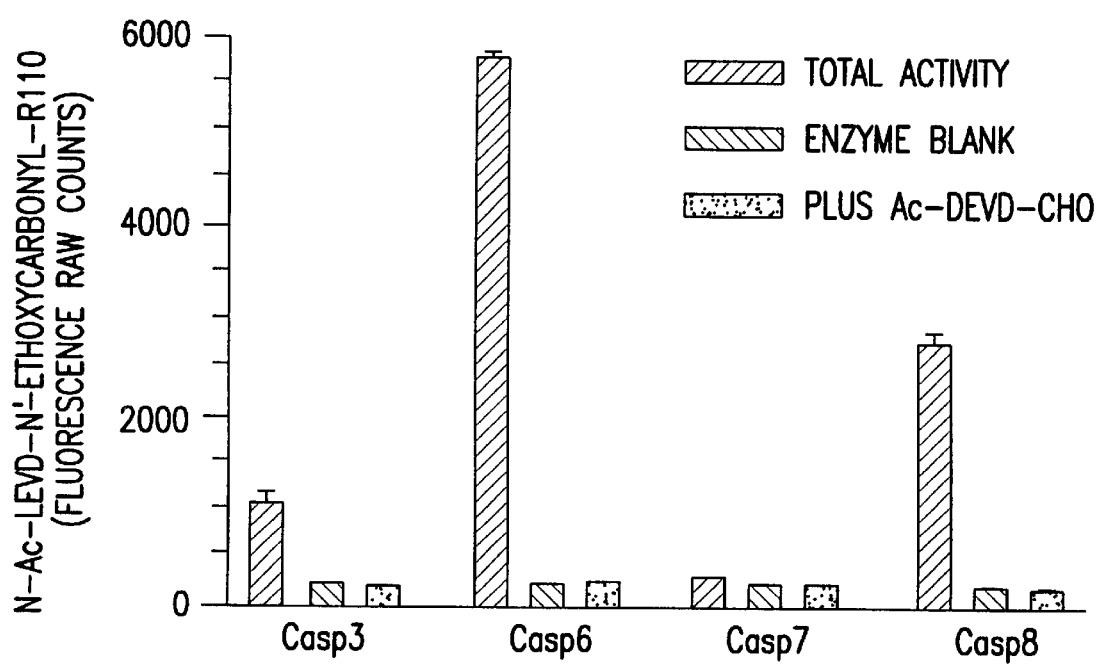
FIG. 5 depicts a bar graph showing the results of a cleavage assay of N-Ac-LEVD-N'-ethoxycarbonyl-R110 SEQ ID NO:5 by caspase-3, -6, -7 and -8.

N-Ac-LEVD-N'-ethoxycarbonyl R110 SEQ ID NO:9 was assayed by recombinant human caspase-3, 6, 7, and 8. The assays were carried out at 37° C. in 96-well plates in a 100 µL incubation containing recombinant human caspase, 10

μM of N-Ac-LEVD-N'-ethoxycarbonyl R110 SEQ ID NO:9, and caspase assay buffer (40 mM PIPES, pH 7.2; 100 mM NaCl; 10% sucrose; 0.1% CHAPS; 1 mM EDTA; 10 mM DTT). At the end of the incubation period, the fluorescence was determined on a Bio-Tek FL500 fluorescence microplate reader using excitation and emission wavelengths of 485 and 530 nm, respectively. In order to correct for the endogenous fluorescence of the uncleaved substrate, controls were run which consisted of samples containing 10 μM N-Ac-LEVD-N'-ethoxycarbonyl R110 SEQ ID NO:9 without enzyme ("enzyme blanks"). Additional controls included samples containing the caspase inhibitor Ac-DEVD-CHO SEQ ID NO:5. As shown in FIG. 5, caspase-6 and caspase-8 cleave N-Ac-LEVD-N'-ethoxycarbonyl R110 SEQ ID NO:9 to give an easily measured fluorescent signal (signal to background ratios of about 13 for caspase-6 to about 26 for caspase-8). Caspase-3 cleaved N-Ac-LEVD-N'-ethoxycarbonyl R110 SEQ ID NO:9 less efficiently, yielding a signal that was about 5-fold above the enzyme blank value. Caspase-7 gave virtually no signal. These experiments show that N-Ac-LEVD-N'-ethoxycarbonyl R110 SEQ ID NO:9 can be cleaved by members of the caspase-8 subfamily and that it can be used to report the activity of this type of caspase.

EXAMPLE 80

Figure 6:
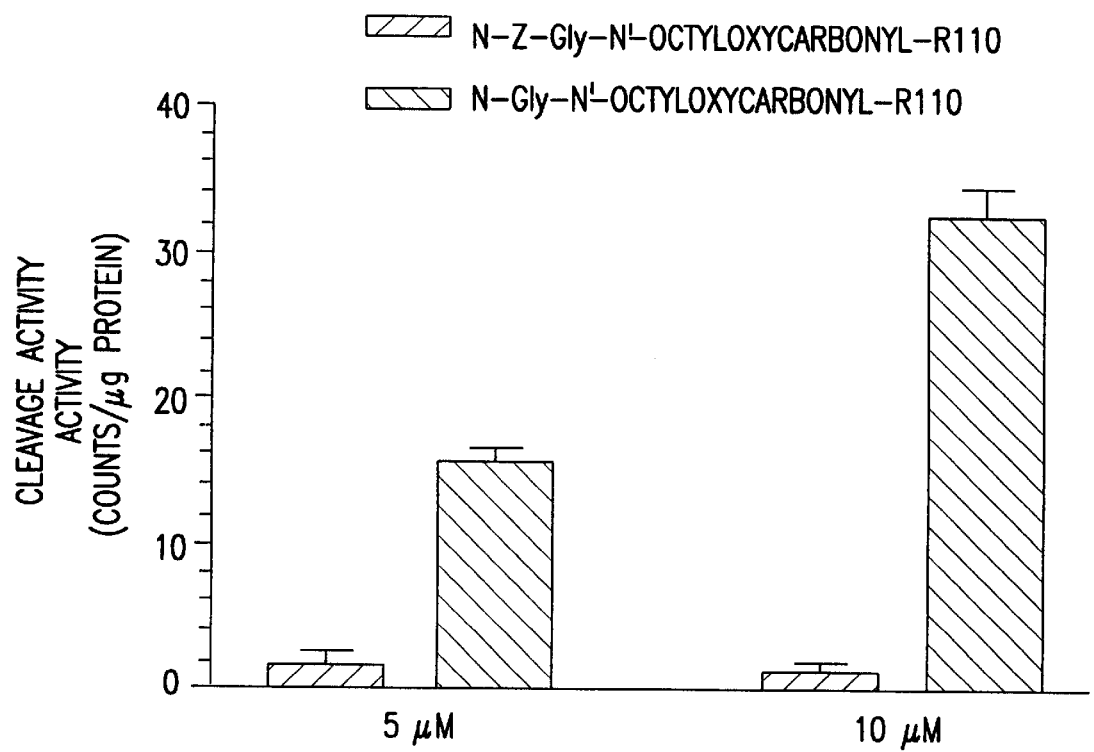
FIG. 6 depicts a bar graph with the results of a cleavage assay of N-Z-G-N'-octyloxycarbonyl-R110 and N-G-N'-octyloxycarbonyl-R110 by HL-60 cell lysates.

Cleavage of the Aminopeptidase Substrate N-G-N'-octyloxycarbonyl R110 by HL-60 Cell Lysates Aminopeptidases are present in many cells and sequentially remove unblocked amino acid residues from peptides, starting from the N-terminus. Peptides with blocked amino termini are not cleaved. HL-60 lysates were prepared by homogenizing HL-60 cells in caspase buffer, and the ability of these lysates to cleave N-Z-G-N'-Loctyloxycarbonyl R110 and N-G-N'-octyloxycarbonyl-R110 was tested in a microtiter plate assay. FIG. 6 shows that HL-60 cell lysates readily cleaved N-G-N'-octyloxycarbonyl R110, and the size of the signal was dependent on the concentration of substrate. By contrast, no signal was generated by HL-60 cell lysates from N-Z-G-N'-octyloxycarbonyl-R110.

EXAMPLE 81

Use of Fluorescence Assay in A screening for Drugs that Stimulate the Caspase Cascade.

Drugs that stimulate the caspase cascade in the absence of Fas ligand may be useful, for example, as anti-cancer chemotherapeutic agents. The assay described in Example 78 may be used to screen for drugs that stimulate the caspase cascade by carrying out the assay under similar conditions as in Example 78, except that a known or unknown compound with known or unknown anti-cancer or anti-tumor activity replaces the Fas ligand reagent.

EXAMPLE 82

Use of Fluorescence Assay in Screening for Drugs that Inhibit or Potentiate the Caspase Cascade Stimulated with Fas Ligand or Another Apoptosis Inducer.

Drugs that inhibit the caspase cascade may be useful in treating degenerative and other diseases caused by or associated with an inadequate activation of the caspase cascade. Drugs that potentiate the action of another caspase stimulator, such as e.g. Fas ligand or an anti-cancer drug or agent, may be suitable to treat cancers or tumors caused by or associated with an inappropriate function of the caspase cascade. The assays and reagents described in this invention may be used to screen for drugs that either inhibit or potentiate the caspase cascade in cells by performing the assay as described in Example 78 using Fas ligand or any other agent that stimulates the caspase cascade or other apoptosis pathway in the presence of a test substance that inhibits or potentiates or acts synergistically with the action of the first apoptosis or caspase cascade inducer.

EXAMPLE 83

Use of Fluorescence Assay in Testing Samples Cancer Cells from Patients for Chemosensitivity to Anti-cancer Drugs.

It is well known that the same cancer in different patients shows a great variability to treatment with anti-cancer drugs. Therefore it is very difficult to predict whether a cancer in a patient is treatable with a particular anti-cancer drug before treatment is begun. The fluorescence assays described in this invention permit chemosensitivity or drug resistance testing of cancer or tumor cells or tissue samples taken from individual cancer or tumor patients. To perform the chemosensitivity test, a fluorescence assay using a cancer cell or tissue sample taken from a patient may be conducted as described Example 78. Using this approach, different drugs with known or unknown chemotherapeutic activity can be tested for their capacity to stimulate the caspase cascade. The results from this assay provide information that can be used to design an optimal chemotherapeutic drug treatment regimen for the patient.

EXAMPLE 84

Figure 7A:
FIGS. 7A–B depict photographs of HL-60 cells treated with N-Z-G-N'-octyloxycarbonyl-R110 (A) and N-G-N'-octyloxycarbonyl-R110 (B).
Figure 7B:
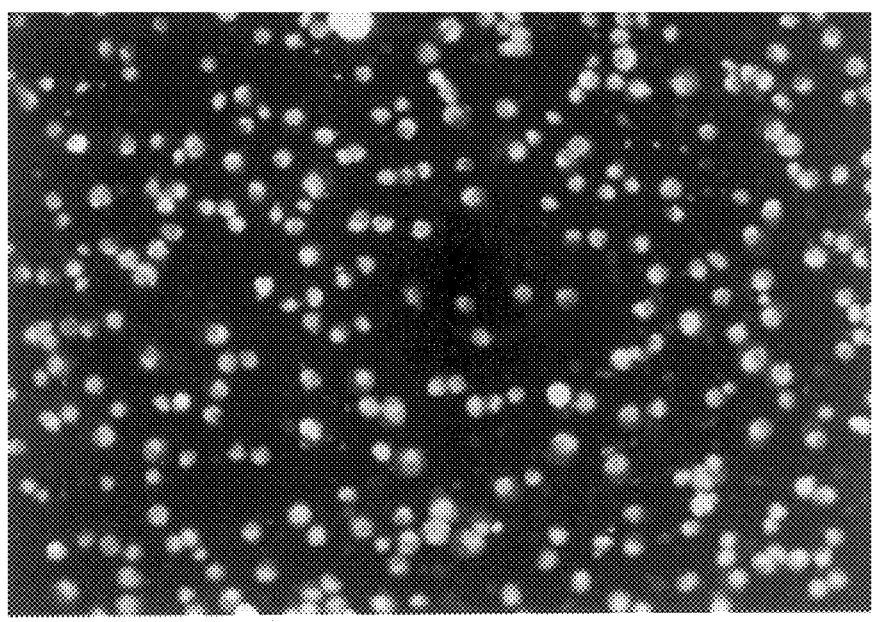

Uptake and Cleavage of the Aminopeptidase Substrate N-G-N'-octyloxycarbonyl-R110 by HL-60 Cells HL-60 cells were placed in 5 ml of Iscove's medium (without serum or phenol-red) containing 10 μM N-G-N'-octyloxycarbonyl-R110 or 10 μM N-Z-G-N-octyloxycarbonyl-R110. Three million HL-60 cells were incubated for 3 hours at 37° C. in a $CO_2$ incubator, recovered by centrifugation, and washed in 50 μL of ice-cold medium. The cells were re-centrifuged and the final pellet was resuspended in 50 μL of fresh medium. Aliquots of each cell suspension were placed in a microtiter 96-well plate and read on a Wallac 1420 microplate reader with excitation wavelength at 485 nm, emission wavelength at 525 nm. Aliquots of each cell suspension were also placed on microslides and viewed on a Nikon inverted microscope with epifluorescent illumination. As shown in table 6, only the cells incubated with 10 μM N-G-N'-octyloxycarbonyl-R110 showed signal. There was no signal from the cells incubated with 10 μM N-Z-G-N'-octyloxycarbonyl-R 110. Similarly, only the cells incubated with N-G-N'-octyloxycarbonyl-R110 showed fluorescence under microscope, and no fluorescence signal was observed from the cells incubated with N-Z-G-N'-octyloxycarbonyl-R110 (FIGS. 7A–B).

TABLE 6

Cleavage of N-G-N'-octyloxycarbonyl-R110 by HL-60 Cells

| Substrate | Counts/μg/protein |
|---|---|
| N-Z-G-N'-octyloxycarbonyl-R110 | 0 |
| N-G-N'-octyloxycarbonyl-R110 | 12.98 |

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A compound having the Formula VI:

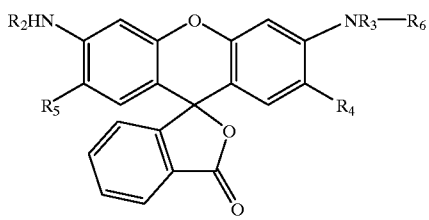

or a biologically acceptable salt of said compound, or a tautomer of said compound, or biologically acceptable salt of said tautomer, wherein $R_2$ and $R_3$ independently are hydrogen, methyl or ethyl;

$R_4$ and $R_5$ independently are hydrogen or methyl; and $R_6$ is a blocking group selected from the group consisting of $C_{1-12}$alkyloxycarbony, $CH_3(OCH_2CH_2)_qOCO-$, $CH_3(CH_2)_r(OCH_2CH_2)_sOCO-$, $C_{1-12}$(alkylthio)carbonyl, aryl($C_{1-12}$)alkoxycarbonyl, $H_2NCO-$, $(CH_3)_2NCO-$, $(CH_3CH_2)_2NCO-$, $(CH_3(CH_2)_v)(CH_3)NCO-$, $C_{1-12}$alkylsulfonyl, $C_{1-12}$haloalkylsulfonyl, aryl($C_{1-12}$)alkylsulfonyl, $Cl_3CCH_2OCO-$, unsubstituted benzoyl, benzylcarbonyl, phenylsulfonyl and tosyl; wherein q is 2–4, r is 0–5, s is 1–4, and v is 1–9.

2. The compound of claim 1, wherein $R_2$, $R_3$, $R_4$ and $R_5$ are hydrogen.

3. The compound of claim 1, wherein $R_2$ and $R_3$ are methyl; and $R_4$ and $R_5$ are hydrogen.

4. The compound of claim 1, wherein $R_2$ and $R_3$ are ethyl; and $R_4$ and $R_5$ are methyl.

5. The compound of claim 1, wherein said blocking group is a $C_{1-12}$alkyloxycarbonyl group.

6. The compound of claim 5, wherein said $C_{1-12}$alkyloxycarbonyl group is selected from the group consisting of methoxycarbonyl, ethoxycarbonyl, butoxycarbonyl, hexyloxycarbonyl, octyloxycarbonyl, decyloxycarbonyl and dodecyloxycarbonyl.

7. The compound of claim 1, wherein said blocking group is $CH_3(OCH_2CH_2)_qOCO-$.

8. The compound of claim 1, wherein said blocking group is $CH_3(CH_2)_r(OCH_2CH_2)_sOCO-$.

9. The compound of claim 1, wherein said blocking group is a $C_{1-12}$(alkylthio)carbonyl group.

10. The compound of claim 9, wherein said $C_{1-12}$(alkylthio)carbonyl group is an selected from the group consisting of (methylthio)carbonyl, (ethylthio)carbony, (butylthio)carbonyl, (hexylthio)carbonyl, (octylthio)carbonyl, (decylthio)carbonyl and (dodecylthio)carbonyl.

11. The compound of claim 1, wherein said blocking group is an aryl($C_{1-12}$)alkoxycarbonyl group.

12. The compound of claim 11, wherein said aryl($C_{1-2}$) alkoxycarbonyl group benzyloxycarbonyl or phenethyloxycarbonyl.

13. The compound of claim 1, wherein said blocking group is $H_2NCO$—, $(CH_3)_2NCO$— or $(CH_3CH_2)_2NCO$—.

14. The compound of claim 13, wherein said blocking group is $(CH_3CH_2)_2NCO$—.

15. The compound of claim 1, wherein said blocking group $(CH_3(CH_2)_v)(CH_3)NCO$—, and v is 1–9.

16. The compound of claim 15, wherein v is 5, 7 or 9.

17. The compound of claim 1, wherein said blocking group is a $C_{1-12}$alkylsulfonyl group.

18. The compound of claim 17, wherein said $C_{1-12}$alkylsulfonyl group is selected from the group consisting of methanesulfonyl, ethanesulfonyl, hexanesulfonyl, octanesulfon, decanesulfonyl and dodecanesulfonyl.

19. The compound of claim 1, wherein said blocking group is a haloalkylsulfonyl group.

20. The compound of claim 16, wherein said haloalkylsulfonyl group is trifluoromethanesulfonyl.

21. The compound of claim 1, wherein said blocking group is an aryl($C_{1-12}$)alkylsulfonyl group.

22. The compound of claim 21, wherein said aryl($C_{1-12}$) alkylsulfonyl group is benzylsulfonyl.

23. The compound of claim 1, wherein said blocking group is $Cl_3CH_2OCO$—.

24. The compound of claim 1, wherein said blocking group is unsubstituted phenylcarbonyl or benzylcarbonyl.

25. The compound of claim 1, wherein said blocking group is phenylsulfonyl or tosyl.

26. A compound having the Formula VI:

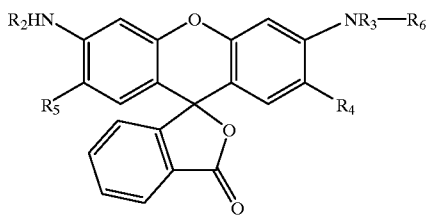

or a biologically acceptable salt of said compound, or a tautomer of said compound, or biologically acceptable salt of said tautomer, wherein $R_2$ and $R_3$ independently are hydrogen, methyl or ethyl;

$R_4$ and $R_5$ independently are hydrogen or methyl; and $R_6$ is a $C_{2-8}$ alkanoyl group.

27. The compound of claim 26, wherein said $C_{2-8}$ alkanoyl group is acetyl, hexanoyl or octanoyl.

28. A compound, wherein said compound is N-acetyl-Rhodamine 110, N-hexanoyl-Rhodamine 110 or N-octanoyl-Rhodamine 110.

29. A compound having the Formula VI:

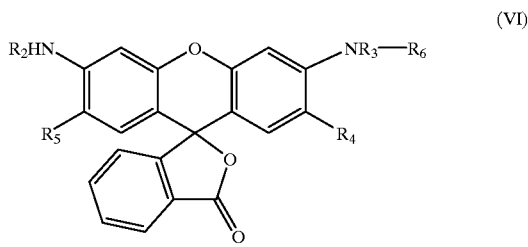

or a biologically acceptable salt of said compound, or a tautomer of said compound, or a biologically acceptable salt of said tautomer, wherein:

$R_2$ is hydrogen;

$R_3$ is hydrogen, methyl, or ethyl;

$R_4$ and $R_5$ independently are hydrogen or methyl; and $R_6$ is a $C_{9-12}$alkanoyl group.

30. A compound having the Formula VI:

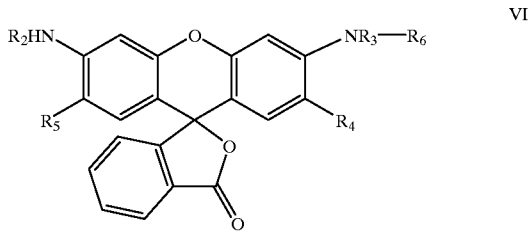

or a biologically acceptable salt of said compound, or a tautomer of said compound, or a biologically acceptable salt of said tautomer, wherein $R_2$ and $R_3$ independently are hydrogen, methyl or ethyl;

$R_4$ and $R_5$ independently are hydrogen or methyl; and $R_6$ is HCO—.

31. The compound of claim 30, wherein said compound is N-formyl-Rhodamine 110.

32. A compound selected from the group consisting of N-methoxycarbonyl-Rhodamine 110, N-ethoxycarbonyl-Rhodamine 110, N-hexyloxycarbonyl-Rhodamine 110, N-octyloxycarbonyl-Rhodamine 110, N-decyloxycarbonyl-Rhodamine 110, and N-dodecyloxycarbonyl-Rhodamine 110.

33. A compound selected from the group consisting of N-dimethylcarbamyl-Rhodamine 110, N-(N-methyl-N-hexylcarbamyl)-Rhodamine 110, N-methanesulfonyl-Rhodamine 110, N-(ethylthio)carbonyl-Rhodamine 110, N-(hexylthio)carbonyl-Rhodamine 110, N-(octylthio)carbonyl-Rhodamine 110, N-(2,5,8-trioxadecyloxycarbonyl)-Rhodamine 110 and N-(2-butoxyethoxycarbonyl)-Rhodamine 110.

34. The compound of claim 29, wherein $R_6$ is a $C_{9-10}$ alkanoyl group.

35. The compound of claim 34, wherein said $C_{9-10}$ alkanoyl group is decanoyl.

36. The compound of claim 35, wherein said compound is N-decanoyl-Rhodamine 110.

37. The compound of claim 34, wherein $R_3$ is methyl or ethyl.

38. The compound of claim 29, wherein $R_6$ is a $C_{11-12}$ alkanoyl group.

39. The compound of claim 38, wherein said $C_{11-12}$ alkanoyl group is dodecanoyl.

40. The compound of claim 39, wherein said compound is N-dodecanoyl-Rhodamine 110.

41. The compound of claim 38, wherein $R_3$ is methyl or ethyl.

* * * * *

```
                        SEQUENCE LISTING

<160> NUMBER OF SEQ ID NOS: 142

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 1

Trp Glu His Asp
  1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 2

Tyr Val Ala Asp
  1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 3

Leu Glu His Asp
  1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 4

Asp Glu Thr Asp
  1

<210> SEQ ID NO 5
<211> LENGTH: 4
<212> TYPE: PRT
<213> ORGANISM: Artificial Sequence
<220> FEATURE:
```

```
<223> OTHER INFORMATION: Description of Artificial Sequence:Synthetic
      Peptide

<400> SEQUENCE: 5

Asp Glu Val Asp
 1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 6

Asp Glu His Asp
 1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 7

Val Glu His Asp
 1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 8

Leu Glu Thr Asp
 1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 9

Leu Glu Val Asp
 1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 10

Ser His Val Asp
 1
```

```
<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 11

Asp Glu Leu Asp
  1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 12

Asp Gly Pro Asp
  1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 13

Asp Glu Pro Asp
  1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 14

Asp Gly Thr Asp
  1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 15

Asp Leu Asn Asp
  1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide
```

-continued

```
<400> SEQUENCE: 16

Asp Glu Glu Asp
  1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 17

Asp Ser Leu Asp
  1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 18

Asp Val Pro Asp
  1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 19

Asp Glu Ala Asp
  1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 20

Asp Ser Tyr Asp
  1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 21

Glu Leu Pro Asp
  1

<210> SEQ ID NO 22
<211> LENGTH: 4
<212> TYPE: PRT
```

```
<213> ORGANISM: Artificial Sequence
<220> FEATURE:
<223> OTHER INFORMATION: Description of Artificial Sequence:Synthetic
      Peptide

<400> SEQUENCE: 22

Val Glu Asp Asp
  1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 23

Ile Glu Pro Asp
  1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 24

Ile Glu Thr Asp
  1

<210> SEQ ID NO 25
<211> LENGTH: 4
<212> TYPE: PRT
<213> ORGANISM: Artificial Sequence
<220> FEATURE:
<221> NAME/KEY: UNSURE
<222> LOCATION: (1)
<223> OTHER INFORMATION: Amino Acid may be Tryptophan or Leucine
<220> FEATURE:
<223> OTHER INFORMATION: Description of Artificial Sequence:Synthetic
      Peptide

<400> SEQUENCE: 25

Xaa Glu His Asp
  1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 26

Val Glu Ile Asp
  1

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide
```

-continued

```
<400> SEQUENCE: 27

Val Glu Pro Asp
  1

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 28

Ser Gln Asn Tyr Pro Ile Val
  1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 29

Ala Arg Val Leu Ala Glu Ala
  1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 30

Ala Thr Ile Met Met Gln Arg
  1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 31

Arg Gln Ala Asn Phe Leu Gly
  1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 32

Pro Gly Asn Phe Leu Gln Ser
  1               5

<210> SEQ ID NO 33
<211> LENGTH: 7
<212> TYPE: PRT
```

```
<213> ORGANISM: Artificial Sequence
<220> FEATURE:
<223> OTHER INFORMATION: Description of Artificial Sequence:Synthetic
      Peptide

<400> SEQUENCE: 33

Ser Phe Ser Phe Pro Gln Ile
  1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 34

Thr Leu Asn Phe Pro Ile Ser
  1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 35

Ala Glu Thr Phe Tyr Val Asp
  1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 36

Arg Lys Val Leu Phe Leu Asp
  1               5

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 37

Arg Gly Phe Pro
  1

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 38

Ser Gln Asn Tyr Pro Val Val
  1               5
```

```
<210> SEQ ID NO 39
<211> LENGTH: 14
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 39

Asp Arg Val Tyr Ile His Pro Phe His Leu Leu Glu Glu Ser
 1               5                  10

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 40

Leu Glu Glu Ser
 1

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 41

Ser Gln Asn Tyr Pro Ile Val Gln
 1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 42

Ser Gln Asn Leu Phe Leu Asp Gly
 1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 43

Arg Lys Ile Leu Phe Leu Asp Gly
 1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence:Synthetic
      Peptide
```

```
<400> SEQUENCE: 44

Lys Ala Arg Val Leu Phe Glu Ala Met
  1               5

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 45

Ser Gln Asn Tyr
  1

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 46

Pro Ile Val Gln
  1

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 47

Lys Ala Arg Val Leu
  1               5

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 48

Ala Arg Val Leu
  1

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 49

Phe Glu Ala Met
  1

<210> SEQ ID NO 50
<211> LENGTH: 4
<212> TYPE: PRT
```

```
<213> ORGANISM: Artificial Sequence
<220> FEATURE:
<223> OTHER INFORMATION: Description of Artificial Sequence:Synthetic
      Peptide

<400> SEQUENCE: 50

Pro Phe His Leu
  1

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 51

Gln Asn Leu Phe
  1

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 52

Arg Lys Ile Leu Phe
  1               5

<210> SEQ ID NO 53
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 53

Lys Ile Leu Phe
  1

<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 54

Ser Leu Asn Phe
  1

<210> SEQ ID NO 55
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 55

Leu Arg Gly Gly
  1
```

```
<210> SEQ ID NO 56
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 56

Met Arg Gly Gly
 1

<210> SEQ ID NO 57
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 57

Ile Arg Gly Gly
 1

<210> SEQ ID NO 58
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 58

Leu Val Gly Gly
 1

<210> SEQ ID NO 59
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 59

Met Val Gly Gly
 1

<210> SEQ ID NO 60
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 60

Ile Val Gly Gly
 1

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence:Synthetic
      Peptide
```

```
<400> SEQUENCE: 61

Leu Val Leu Ala Ser Ser Ser Phe
 1               5

<210> SEQ ID NO 62
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 62

Leu Val Leu Ala
 1

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 63

Arg Gly Val Val Asn Ala Ser Ser Arg Leu Ala
 1               5                  10

<210> SEQ ID NO 64
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 64

Val Val Asn Ala
 1

<210> SEQ ID NO 65
<211> LENGTH: 4
<212> TYPE: PRT
<213> ORGANISM: Artificial Sequence
<220> FEATURE:
<221> NAME/KEY: SITE
<222> LOCATION: (1)..(2)
<223> OTHER INFORMATION: t-butylglycine
<220> FEATURE:
<223> OTHER INFORMATION: Description of Artificial Sequence:Synthetic
      Peptide

<400> SEQUENCE: 65

Gly Gly Asn Ala
 1

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 66

Asp Asp Ile Val Pro Cys Ser Met Ser Tyr
 1               5                  10
```

```
<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 67

Asp Asp Ile Val Pro Cys
 1               5

<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 68

Asp Ile Val Pro Cys
 1               5

<210> SEQ ID NO 69
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 69

Ile Val Pro Cys
 1

<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 70

Ser Met Ser Tyr
 1

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 71

Trp Glu His Asp Gly
 1               5

<210> SEQ ID NO 72
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide
```

```
<400> SEQUENCE: 72

Tyr Val Ala Asp Gly
  1               5

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 73

Leu Glu His Asp Gly
  1               5

<210> SEQ ID NO 74
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 74

Leu Glu Val Asp Gly
  1               5

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 75

Asp Glu Thr Asp Gly
  1               5

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 76

Asp Glu Val Asp Gly
  1               5

<210> SEQ ID NO 77
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 77

Leu Glu Thr Asp Gly
  1               5

<210> SEQ ID NO 78
<211> LENGTH: 5
<212> TYPE: PRT
```

```
<213> ORGANISM: Artificial Sequence
<220> FEATURE:
<223> OTHER INFORMATION: Description of Artificial Sequence:Synthetic
      Peptide

<400> SEQUENCE: 78

Asp Glu His Asp Gly
 1               5

<210> SEQ ID NO 79
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 79

Trp Glu His Asp Gly Gly
 1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 80

Ser Leu Asn Phe Pro Ile Val
 1               5

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 81

Ser Leu Asn Phe Pro Ile
 1               5

<210> SEQ ID NO 82
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 82

Ser Leu Asn Phe Pro
 1               5

<210> SEQ ID NO 83
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 83

Leu Asn Phe Pro Ile Val
 1               5
```

```
<210> SEQ ID NO 84
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 84

Leu Asn Phe Pro Ile
 1               5

<210> SEQ ID NO 85
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 85

Leu Asn Phe Pro
 1

<210> SEQ ID NO 86
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 86

Arg Gln Ala Asn Phe Leu
 1               5

<210> SEQ ID NO 87
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 87

Arg Gln Ala Asn Phe
 1               5

<210> SEQ ID NO 88
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 88

Arg Lys Val Leu Phe Leu
 1               5

<210> SEQ ID NO 89
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide
```

```
<400> SEQUENCE: 89

Arg Lys Val Leu Phe
  1               5

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 90

Ala Arg Val Leu Phe Leu Gly
  1               5

<210> SEQ ID NO 91
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 91

Ala Arg Val Leu Phe Leu
  1               5

<210> SEQ ID NO 92
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 92

Ala Arg Val Leu Phe
  1               5

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 93

Ser Gln Asn Tyr Phe Leu Gly
  1               5

<210> SEQ ID NO 94
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 94

Ser Gln Asn Tyr Phe Leu
  1               5

<210> SEQ ID NO 95
<211> LENGTH: 5
<212> TYPE: PRT
```

```
<213> ORGANISM: Artificial Sequence
<220> FEATURE:
<223> OTHER INFORMATION: Description of Artificial Sequence:Synthetic
      Peptide

<400> SEQUENCE: 95

Ser Gln Asn Tyr Phe
 1               5

<210> SEQ ID NO 96
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 96

Met Arg Gly Gly Gly
 1               5

<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 97

Ile Arg Gly Gly Gly
 1               5

<210> SEQ ID NO 98
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 98

Leu Val Gly Gly Gly
 1               5

<210> SEQ ID NO 99
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 99

Met Val Gly Gly Gly
 1               5

<210> SEQ ID NO 100
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 100

Ile Val Gly Gly Gly
 1               5
```

```
<210> SEQ ID NO 101
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 101

Leu Arg Gly Gly Gly
  1               5

<210> SEQ ID NO 102
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 102

Leu Arg Gly Gly Ala
  1               5

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 103

Leu Val Leu Ala Ser Ser Ser
  1               5

<210> SEQ ID NO 104
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 104

Leu Val Leu Ala Ser Ser
  1               5

<210> SEQ ID NO 105
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 105

Leu Val Leu Ala Ser
  1               5

<210> SEQ ID NO 106
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide
```

```
<400> SEQUENCE: 106

Val Val Asn Ala Ser Ser
 1               5

<210> SEQ ID NO 107
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 107

Val Val Asn Ala Ser
 1               5

<210> SEQ ID NO 108
<211> LENGTH: 6
<212> TYPE: PRT
<213> ORGANISM: Artificial Sequence
<220> FEATURE:
<221> NAME/KEY: SITE
<222> LOCATION: (1)..(2)
<223> OTHER INFORMATION: t-butylglycine
<220> FEATURE:
<223> OTHER INFORMATION: Description of Artificial Sequence:Synthetic
      Peptide

<400> SEQUENCE: 108

Gly Gly Asn Ala Ser Ser
 1               5

<210> SEQ ID NO 109
<211> LENGTH: 5
<212> TYPE: PRT
<213> ORGANISM: Artificial Sequence
<220> FEATURE:
<221> NAME/KEY: SITE
<222> LOCATION: (1)..(2)
<223> OTHER INFORMATION: t-butylglycine
<220> FEATURE:
<223> OTHER INFORMATION: Description of Artificial Sequence:Synthetic
      Peptide

<400> SEQUENCE: 109

Gly Gly Asn Ala Ser
 1               5

<210> SEQ ID NO 110
<211> LENGTH: 4
<212> TYPE: PRT
<213> ORGANISM: Artificial Sequence
<220> FEATURE:
<221> NAME/KEY: SITE
<222> LOCATION: (1)..(2)
<223> OTHER INFORMATION: t-butylglycine
<220> FEATURE:
<223> OTHER INFORMATION: Description of Artificial Sequence:Synthetic
      Peptide

<400> SEQUENCE: 110

Gly Gly Asn Ala
 1

<210> SEQ ID NO 111
<211> LENGTH: 10
<212> TYPE: PRT
<213> ORGANISM: Artificial Sequence
<220> FEATURE:
```

```
<223> OTHER INFORMATION: Description of Artificial Sequence:Synthetic
      Peptide

<400> SEQUENCE: 111

Asp Asp Ile Val Pro Cys Ser Met Ser Thr
 1               5                  10

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 112

Asp Ile Val Pro Cys Ser Met Ser Thr
 1               5

<210> SEQ ID NO 113
<211> LENGTH: 8
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 113

Ile Val Pro Cys Ser Met Ser Thr
 1               5

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 114

Ile Val Pro Cys Ser Met Ser
 1               5

<210> SEQ ID NO 115
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 115

Ile Val Pro Cys Ser Met
 1               5

<210> SEQ ID NO 116
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 116

Ile Val Pro Cys Ser
 1               5
```

```
<210> SEQ ID NO 117
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 117

Ser Gln Asn Tyr Pro Ile
 1               5

<210> SEQ ID NO 118
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 118

Ala Arg Val Leu Ala Glu
 1               5

<210> SEQ ID NO 119
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 119

Ala Thr Ile Met Met Gln
 1               5

<210> SEQ ID NO 120
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 120

Arg Gln Ala Asn Phe Leu
 1               5

<210> SEQ ID NO 121
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 121

Pro Gly Asn Phe Leu Gln
 1               5

<210> SEQ ID NO 122
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide
```

```
<400> SEQUENCE: 122

Ser Phe Ser Phe Pro Gln
 1               5

<210> SEQ ID NO 123
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 123

Thr Leu Asn Phe Pro Ile
 1               5

<210> SEQ ID NO 124
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 124

Ala Glu Thr Phe Tyr Val
 1               5

<210> SEQ ID NO 125
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 125

Arg Lys Val Leu Phe Leu
 1               5

<210> SEQ ID NO 126
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 126

Ser Gln Asn Tyr Pro
 1               5

<210> SEQ ID NO 127
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 127

Ala Arg Val Leu Ala
 1               5

<210> SEQ ID NO 128
<211> LENGTH: 5
<212> TYPE: PRT
```

```
<213> ORGANISM: Artificial Sequence
<220> FEATURE:
<223> OTHER INFORMATION: Description of Artificial Sequence:Synthetic
      Peptide

<400> SEQUENCE: 128

Ala Thr Ile Met Met
 1               5

<210> SEQ ID NO 129
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 129

Arg Gln Ala Asn Phe
 1               5

<210> SEQ ID NO 130
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 130

Pro Gly Asn Phe Leu
 1               5

<210> SEQ ID NO 131
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 131

Ser Phe Ser Phe Pro
 1               5

<210> SEQ ID NO 132
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 132

Thr Leu Asn Phe Pro
 1               5

<210> SEQ ID NO 133
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 133

Ala Glu Thr Phe Tyr
 1               5
```

-continued

```
<210> SEQ ID NO 134
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 134

Arg Lys Val Leu Phe
 1               5

<210> SEQ ID NO 135
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 135

Met Arg Gly Gly Ala
 1               5

<210> SEQ ID NO 136
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 136

Ile Arg Gly Gly Ala
 1               5

<210> SEQ ID NO 137
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 137

Leu Val Gly Gly Ala
 1               5

<210> SEQ ID NO 138
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 138

Met Val Gly Gly Ala
 1               5

<210> SEQ ID NO 139
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide
```

```
-continued

<400> SEQUENCE: 139

Ile Val Gly Gly Ala
1               5

<210> SEQ ID NO 140
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 140

Ser Gln Asn Leu Phe
1               5

<210> SEQ ID NO 141
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 141

Thr Ile Asn Phe Gln Arg
1               5

<210> SEQ ID NO 142
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 142

Tyr Val Ala Asp Gly Gly
1               5
```